United States Patent
Katz et al.

(10) Patent No.: US 8,518,911 B2
(45) Date of Patent: Aug. 27, 2013

(54) PYRAZOLO[1,5-A]PYRIDINES AS MARK INHIBITORS

(75) Inventors: Jason D. Katz, Newton Highlands, MA (US); Sandra L. Knowles, Cambridge, MA (US); James P. Jewell, Sandwich, MA (US); David L. Sloman, Boston, MA (US); Matthew G. Stanton, Marlton, NJ (US); Njamkou Noucti, Somerville, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 288 days.

(21) Appl. No.: 13/057,510

(22) PCT Filed: Jul. 27, 2009

(86) PCT No.: PCT/US2009/051785
§ 371 (c)(1),
(2), (4) Date: Apr. 26, 2011

(87) PCT Pub. No.: WO2010/017046
PCT Pub. Date: Feb. 11, 2010

(65) Prior Publication Data
US 2011/0195933 A1    Aug. 11, 2011

Related U.S. Application Data

(60) Provisional application No. 61/137,935, filed on Aug. 5, 2008.

(51) Int. Cl.
A61K 31/675    (2006.01)
A61K 31/437    (2006.01)
A61K 31/496    (2006.01)
A61K 31/397    (2006.01)

(52) U.S. Cl.
USPC ..... 514/80; 514/300; 514/233.2; 514/253.04; 514/278; 514/221; 546/121; 546/18; 546/21; 544/362; 544/127; 540/569

(58) Field of Classification Search
USPC ................. 514/80, 300, 253.04, 233.2, 278, 514/210.21, 221; 546/121, 18, 21; 544/362, 544/127; 540/569
See application file for complete search history.

(56) References Cited

U.S. PATENT DOCUMENTS

| 7,151,109 B2 | 12/2006 | Fu |
| 2010/0305091 A1 | 12/2010 | Stanton et al. |

FOREIGN PATENT DOCUMENTS

| EP | 497258 | 1/1991 |
| EP | 556080 | 8/1993 |
| WO | 03078435 | 9/2003 |
| WO | 2004026871 | 4/2004 |
| WO | 2004050659 | 6/2004 |
| WO | 2004082638 | 9/2004 |
| WO | 2007085873 | 8/2007 |
| WO | 2007087283 | 8/2007 |
| WO | 2008078091 | 7/2008 |
| WO | 2008078100 | 7/2008 |

OTHER PUBLICATIONS

Panneerselvam et al., Crystal structure of the catalytic and ubiquitin-associated domains of the protein kinase MARK2/PAR-1 from *Rattus norvegieus* (2006), pp. 1-107.

*Primary Examiner* — Niloofar Rahmani
(74) *Attorney, Agent, or Firm* — Susan L. Hess; Raynard Yuro; Gerard M. Devlin

(57) ABSTRACT

The invention encompasses pyrazolo[1,5-a]pyridine derivatives which selectively inhibit microtubule affinity regulating kinase (MARK) and are therefore useful for the treatment or prevention of Alzheimer's disease. Pharmaceutical compositions and methods of use are also included.

19 Claims, No Drawings

PYRAZOLO[1,5-A]PYRIDINES AS MARK INHIBITORS

BACKGROUND OF THE INVENTION

Alzheimer's disease (AD) is the most common cause of dementia in the elderly and is characterised by a decline in cognitive function, that progresses slowly and results in symptoms such as memory loss and disorientation. Death occurs, on average, 9 years after diagnosis. The incidence of AD increases with age, so that while about 5% of people over the age of 70 are sufferers, this figure increases to 20% of those over 80 years old.

Existing treatments exclusively target the primary symptoms of AD. Diseased neurons may release insufficient or excessive amounts of particular neurotransmitters, and so current drugs are aimed at increasing neurotransmitter levels or at reducing the stimulation of nerve cells by neurotransmitters. Although these drugs provide some improvement in the symptoms of AD, they fail to address the underlying cause of the disease.

The classic clinical and neuropathological features of AD consist of senile or neuritic plaques and tangled bundles of fibers (neurofibrillary tangles) [Verdile, G., et al, Pharm. Res. 50:397-409 (2004)]. In addition, there is a severe loss of neurons in the hippocampus and the cerebral cortex. Neuritic plaques are extracellular lesions, consisting mainly of deposits of β-amyloid peptide (Aβ), surrounded by dystrophic (swollen, damaged and degenerating) neurites and glial cells activated by inflammatory processes. In contrast, neurofibrillary tangles (NFTs) are intracellular clusters composed of a hyperphosphorylated form of the protein tau, which are found extensively in the brain (e.g. mainly in cortex and hippocampus in AD). Tau is a soluble cytoplasmic protein which has a role in microtubule stabilisation. Excessive phosphorylation of this protein renders it insoluble and leads to its aggregation into paired helical filaments, which in turn form NFTs.

The amyloid cascade hypothesis proposes that abnormal accumulation of Aβ peptides, particularly Aβ42, initiates a cascade of events leading to the classical symptoms of AD and ultimately, to the death of the patient. There is strong evidence [e.g. Rapoport, M., et al (2002) Proc. Natl. Acad. Sci. USA 99:6364-6369] that dysregulation of tau function is a key step in the cascade of Alzheimer's disease pathology leading ultimately to neuronal death. Furthermore, tau mutations and NFTs are found in other dementias in which Aβ pathology is absent, such as frontotemporal dementia, Pick's disease and parkinsonism linked to chromosome 17 (FTDP-17) [Mizutani, T. (1999) Rinsho Shikeigaku 39: 1262-1263]. Also, in AD the frequency of NFTs correlates to the degree of dementia better than that of senile plaques [Arriagada, P. V., et al (1992) Neurology 42:631-639], while significant numbers of amyloid plaques are often found in the brains of non-demented elderly people, suggesting that amyloid pathology on its own is not sufficient to cause dementia. For these reasons, normalisation of tau function (in particular prevention of hyperphosphorylation) is seen as a desirable therapeutic goal for the treatment of AD and other dementing conditions.

Tau is a 352-441 amino acid protein encoded by the Mapt (Microtubule-associated protein tau) gene which is widely expressed in the central nervous system (CNS) with localisation primarily in axons [Binder et al *J. Cell Biol.* 1985, 101(4), 1371-1378]. The major function of tau is regulation of the stability of microtubules (MTs), intracellular structural components comprised of tubulin dimers which are integral in regulating many essential cellular processes such as axonal transport and elongation as well as generation of cell polarity and shape. Tau binding to tubulin is a key factor in determining the rates of polymerisation/depolymerisation (termed dynamic instability) of MTs, and tau is therefore key to the regulation of many essential cellular processes [see, for example, Butner, K. A., Kirschner, M. W. (1991) *J. Cell. Biol.* 115: 717-730].

Tau is a basic protein with numerous serine and threonine residues, many of which are susceptible to phosphorylation. While normal tau has two to three phosphorylated amino acid residues, hyperphosphorylated tau found in AD and other tauopathies typically has eight or nine phosphorylated residues. A variety of kinases promote phosphorylation of these sites, including proline-directed kinases such as glycogen synthase kinase 3β (GSK3β) and cyclin dependent kinase 5 (cdk5), and non-proline-directed kinases such as protein kinase A (PKA) and calmodulin (CaM) kinase II, which phosphorylate tau at Lys-(Ile/Cys)-Gly-Ser sequences, also known as KXGS motifs. One KXGS motif is found in each of the MT binding repeats. Phosphorylation at these sites is important for the regulation of tau-MT binding and while the degree of phosphorylation is normally low, it has been shown to be increased in brain tissue from AD patients, Phosphorylation of one particular residue within the KXGS motifs, Ser-262 has been shown to be elevated in tau protein extracted from the NFTs in AD [Hasegawa, M. et al (1992) *J. Biol. Chem.* 267:17047-17054] and phosphorylation at this site also appears to dramatically reduce MT binding [Biernat, J. et al. (1993) *Neuron* 11: 153-163]. Nishimura et al. [*Cell* 116: 671-682 (2004)] demonstrated that overexpression of the kinase PAR-1 in *Drosophila* led to enhanced tau-mediated toxicity and an increase in the phosphorylation of tau on Ser-262, Ser-356, and other amino acid residues, including sites phosphorylated by GSK3β and Cdk5. Their findings suggest that PAR-1 kinase acts as a master kinase during the process of tau hyperphosphorylation, with the phosphorylation of the Ser-262 and Ser-356 sites being a prerequisite for the subsequent phosphorylation at downstream sites by other kinases.

The mammalian ortholog of PAR-1 is microtubule affinity-regulating kinase (MARK). There are four MARK isoforms and these form part of the AMP-dependent protein kinase (AMPK) family. Like PAR-1, MARK is thought to phosphorylate tau, perhaps in response to an external insult, such as the disruption of $Ca^{2+}$ homeostasis caused by Aβ, priming it for further phosphorylation events. It is not clear whether the phosphorylation of tau by MARK leads directly to its detachment from MTs or the subsequent phosphorylation events cause detachment. The resulting unbound, hyperphosphorylated tau is delocalised to the somatodendritic compartment and is then cleaved by caspases to form fragments prone to aggregation [Drewes, G. (2004). *Trends Biochem. Sci* 29:548-555; Gamblin, T. C., et al, (2003) *Proc. Natl. Acad. Sci. U.S.A.* 100:10032-10037]. These aggregates can grow into filaments, which are potentially toxic, eventually forming the NFTs found in AD.

For these reasons, it is proposed that MARK inhibitors will enable the prevention or amelioration of neurodegeneration in AD and other tauopathies.

This invention relates to methods and materials for the treatment or prevention of neurodegenerative diseases such as Alzheimer's disease. In particular, there is disclosed a particular class of pyrazolo[1,5-a]pyridine derivatives which selectively inhibit microtubule affinity regulating kinase (MARK).

SUMMARY OF THE INVENTION

The invention encompasses pyrazolo[1,5-a]pyridine derivatives which selectively inhibit microtubule affinity regulating kinase (MARK) and are therefore useful for the treatment or prevention of Alzheimer's disease. Pharmaceutical compositions and methods of use are also included.

DETAILED DESCRIPTION OF THE INVENTION

The invention encompasses a compound of formula I:

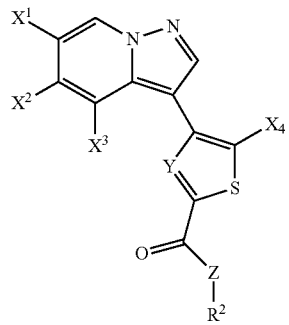

I or a pharmaceutically acceptable salt or hydrate thereof; wherein:

Z is —N($R^1$)— or —O—;

$X^1$ is selected from the group consisting of: H, halogen, $C_{1-6}$alkyl, $C_{2-6}$alkenyl, $C_{3-6}$cycloalkyl, $CF_3$, methoxy, CN, $CON(R^3)_2$, (trimethylsilyl)ethynyl, phenyl and a monocyclic or bicyclic ring system comprising up to 10 ring atoms, of which 1-3 are selected from N, O and S and the remainder are C, said phenyl and ring system bearing 0-3 substituents independently selected from halogen and $C_{1-4}$alkyl, optionally substituted with up to 3 halogen atoms;

$X^2$ is selected from the group consisting of: H, halogen, $C_{1-6}$alkyl, $C_{2-6}$alkenyl, $C_{3-6}$cycloalkyl, $CF_3$, methoxy, CN, $CON(R^3)_2$, (trimethylsilyl)ethynyl, and phenyl bearing 0 to 5 halogen substituents;

$X^3$ is selected from the group consisting of: H, $OR^3$, N($R^3)_2$, $C_{1-6}$alkyl, $C_{2-6}$alkenyl, $C_{3-6}$cycloalkyl, $CF_3$, methoxy, CN, $CON(R^3)_2$, (trimethylsilyl)ethynyl, and halogen;

$X^4$ is selected from the group consisting of: H, halogen, $C_{3-6}$cycloalkyl, $C_{1-6}$alkyl, $C_{2-6}$alkenyl, $C_{2-6}$alkynyl, $C_{3-6}$cycloalkenyl, CN, nitro and $N(R^3)_2$; said $C_{1-6}$alkyl optionally substituted with up to 3 halogen atoms and said $C_{2-6}$alkenyl and $C_{2-6}$alkynyl optionally substituted with up to 3 $R^5$ groups Y is selected from the group consisting of: N and CH;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:
(i) H;
(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and
(iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 4 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and —P(O)—$(OR^3)_2$; where "aryl" refers to phenyl or 5- or 6-membered heteroaryl, either of which phenyl or heteroaryl is optionally fused to a 5- or 6-membered carbocycle or heterocycle, "Het" refers to a nonaromatic or partially aromatic mono- or bicyclic heterocyclic system of up to 10 ring atoms and $C_{3-10}$cycloalkyl and the cyclic portion of $C_{3-10}$cycloalkyl$C_{1-4}$alkyl may be fused with phenyl or a 5- or 6-membered heteroaryl;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each $R^3$ independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^3$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^3$ groups attached to the same atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino;

$R^4$ has the same definition as $R^3$ except that $R^4$ is not H; and $R^5$ is selected from the group consisting of: phenyl, hydroxy, $C_{3-6}$cycloalkyl, and methoxy.

In an embodiment the invention encompasses a genus of compounds of formula I, or a pharmaceutically acceptable salt or hydrate thereof; wherein:

Z is —N($R^1$)—;

$X^1$ is selected from the group consisting of: H, halogen, phenyl, and a monocyclic or bicyclic ring system comprising up to 10 ring atoms, of which 1-3 are selected from N, O and S and the remainder are C, said phenyl and ring system bearing 0-3 substituents independently selected from halogen and $C_{1-4}$alkyl, optionally substituted with up to 3 halogen atoms;

$X^2$ is selected from the group consisting of: H, halogen and phenyl bearing 0 to 5 halogen substituents;

$X^3$ is selected from the group consisting of: H, $OR^3$, N($R^3)_2$, $C_{1-6}$alkyl and halogen;

$X^4$ is selected from the group consisting of: H, halogen, $C_{3-6}$cycloalkyl and $C_{1-6}$alkyl, optionally substituted with up to 3 halogen atoms;

Y is selected from the group consisting of: N and CH;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:
(i) H;
(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and
(iii) $C_{3-10}$cycloalkyl, $C_{3-10}$cycloalkyl$C_{1-4}$ alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicycle heterocyclic system of up to 10 ring atoms;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each R3 independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^3$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^3$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and $R^4$ has the same definition as $R^3$ except that $R^4$ is not H.

Within the genus, the invention encompasses a first sub-genus of compounds of Formula I wherein Y is CH.

Also within the genus, the invention encompasses a second sub-genus of compounds of Formula I wherein Y is N.

Also within the genus, the invention encompasses a third sub-genus of compounds of Formula I wherein $X^1$ is phenyl bearing 0 to 3 halogen substituents.

Also within the genus, the invention encompasses a fourth sub-genus of compounds of Formula I wherein $X^1$ is H.

Also within the genus, the invention encompasses a fifth sub-genus of compounds of Formula I wherein $X^1$ is halogen.

Also within the genus, the invention encompasses a sixth sub-genus of compounds of Formula I wherein $X^1$ is 1-methyl-1H-pyrazol-4-yl.

Also within the genus, the invention encompasses a seventh sub-genus of compounds of Formula I wherein $X^3$ is H or methoxy.

Also within the genus, the invention encompasses an eighth sub-genus of compounds of Formula I wherein $X^4$ is H, halogen or methyl.

Also within the genus, the invention encompasses a ninth sub-genus of compounds of Formula I wherein $R^1$ is H.

Also within the genus, the invention encompasses a tenth sub-genus of compounds of Formula I wherein $R^2$ is $C_{3-10}$cycloalkyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

Within the tenth sub-genus, the invention encompasses a class of compounds of Formula I wherein $R^2$ is cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

Also within the genus, the invention encompasses an eleventh sub-genus of compounds of Formula I wherein $R^2$ is $C_{1-8}$alkyl, which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents.

Also within the genus, the invention encompasses a twelfth sub-genus of compounds of Formula I wherein:

$X^1$ is selected from the group consisting of: H, halogen, phenyl bearing 0 to 3 halogen substituents and 1-methyl-1H-pyrazol-4-yl;

$X^2$ is selected from the group consisting of: H, halogen and phenyl bearing 0 to 5 halogen substituents;

$X^3$ is H or methoxy;

$X^4$ is H, halogen or methyl;

$R^1$ is H; and $R^2$ is selected from the group consisting of:

(i) $C_{1-8}$alkyl, which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and (ii) cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

The invention also encompasses a compound selected from the group consisting of:

N-[(1R,6R)-6-amino-2,2-difluorocyclohexyl]-5-chloro-4-[6-fluorophenyl)pyrazolo[1,5-a]pyridin-3-yl]-1,3-thiazole-2-carboxamide;

N-[(1R,6R)-6-amino-2,2-difluorocyclohexyl]-5-chloropyrazolo{1,5-a]pyridine-3-yl-1,3-thiazole-2-carboxamide;

N-(2-amino-3,3,3-trifluoro-1-phenylpropyl)-5-chloro-4-pyrazolo[1,5-a]pyridin-3-yl-1,3-thiazole-2-carboxamide;

N-[(1R,2R)-2-amino-1,2-diphenylethyl)-5-chloro-4-pyrazolo[1,5-a]pyridin-3-yl-1,3-thiazole-2-carboxamide;

5-chloro-4-pyrazolo[1,5-a]pyridin-3-yl-1,3-N-(2,2,2-trifluoroethyl)-1,3-thiazole-2-carboxamide;

N-[2-amino-1-phenylethyl)-5-chloro-4-pyrazolo[1,5-a]pyridin-3-yl-1,3-thiazole-2-carboxamide;

N-[(1R,6S)-6-amino-2,2-difluorocyclohexyl]-5-chloro-4-pyrazolo[1,5-a]pyridin-3-yl-1,3-thiazole-2-carboxamide;

N-[(1R,6R)-6-amino-2,2-difluorocyclohexyl]-5-bromo-4-pyrazolo[1,5-a]pyridin-3-yl-1,3-thiazole-2-carboxamide;

N-[(1R,6R)-6-amino-2,2-difluorocyclohexyl]-5-chloro-4-fluoropyrazolo{1,5-a]pyridine-3-yl-1,3-thiazole-2-carboxamide;

N-[(1R,6S)-6-amino-2,2-difluorocyclohexyl]-5-chloro-4-fluoropyrazolo{1,5-a]pyridine-3-yl-1,3-thiazole-2-carboxamide;

N-[(1R,6R)-6-amino-2,2-difluorocyclohexyl]-5-methylpyrazolo{1,5-a]pyridine-3-yl-1,3-thiazole-2-carboxamide;

N-[(1R,6R)-6-amino-2,2-difluorocyclohexyl]-4-(4-fluoropyrazolo[1,5-a]pyridin-3-yl)-5-methyl-1,3-thiazole-2-carboxamide;

N-[(1R,6R)-6-amino-2,2-difluorocyclohexyl]-4-(6-chloropyrazolo[1,5-a]pyridin-3-yl)-5-methyl-1,3-thiazole-2-carboxamide;

N-[(1R,6R)-6-amino-2,2-difluorocyclohexyl]-4-(6-bromopyrazolo[1,5-a]pyridin-3-yl)-5-methyl-1,3-thiazole-2-carboxamide;

N-[(1R,2R)-2-amino-1,2-diphenylethyl]-5-methyl-4-pyrazolo[1,5-a]pyridin-3-yl]-1,3-thiazole-2-carboxamide;

N-[(cis)-2-aminocyclohexyl]-5-methyl-4-pyrazolo[1,5-a]pyridin-3-yl]-1,3-thiazole-2-carboxamide;

N-[(cis)-2-aminocyclohexyl]-5-methyl-4-[6-(1-methyl-1H-pyrazol-4-yl)pyrazolo[1,5-a]pyridin-3-yl]-1,3-thiazole-2-carboxamide;

N-(2-amino-1-phenylethyl)-5-methyl-4-[6-(1-methyl-1H-pyrazol-4-yl)pyrazolo[1,5-a]pyridin-3-yl]-1,3-thiazole-2-carboxamide;

N-[(1S,2S)-2-amino-1,2-diphenyl]-5-methyl-4-[6-(1-methyl-1H-pyrazol-4-yl)pyrazolo[1,5-a]pyridin-3-yl]-1,3-thiazole-2-carboxamide;

N-[(1R,6R)-6-amino-2,2-difluorocyclohexyl]-5-methyl-4-[6-(1-methyl-1H-pyrazol-4-yl)pyrazolo[1,5-a]pyridin-3-yl]-1,3-thiazole-2-carboxamide;

N-[(1S)-2-hydroxy-1-phenyl ethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(2-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(3-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(3-chloro-5-fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(4-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(3-fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(1S)-1-(4-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;

N-[(cis)-2-aminocyclohexyl]-4-(4-methoxy-6-[phenylpyrazolo{1,5-a]pyridine-3-yl)-2-thiophenecarboxamide;

N-[(1R,6R)-6-amino-2,2-difluorocyclohexyl]-4-methoxy-6-phenylpyrazolo[1,5-a]pyridin-3-yl]-2-thiophenecarboxamide;

4-(4-methoxy-6-(1-methyl-1H-pyrazol-4-yl)pyrazolo[1,5-a]pyridin-3-yl]-2-thiophenecarboxamide;

N-[(1S)-2-hydroxy-1-phenylethyl]-4-methoxy-6-phenylpyrazolo[1,5-a]pyridin-3-yl]-2-thiophenecarboxamide;

N-[(1S)-2-hydroxy-1-phenylethyl]-4-methoxy-6-(1-methyl-1H-pyrazol-4-yl)pyrazolo[1,5-a]pyridin-3-yl]-2-thiophenecarboxamide;

N-[(1R,6R)-6-amino-2,2-difluorocyclohexyl]-4-[6-fluorophenyl)pyrazolo[1,5-a]pyridin-3-yl]-5-methyl-2-thiophenecarboxamide;

N-(3-amino-4,4,4-trifluorobutyl)-4-(4-methoxy-6-phenylpyrazolo[1,5-a]pyridin-3-yl]-2-thiophenecarboxamide;

N-[(cis)-2-aminocyclohexyl]-4-pyrazolo[1,5-a]pyridin-3-yl]-2-thiophenecarboxamide; and N-[(1R,6R)-6-amino-2,2-difluorocyclohexyl]-5-chloro-4-pyrazolo[1,5-a]pyridin-3-yl-2-thiophenecarboxamide;

or a pharmaceutically acceptable salt of any of the foregoing compounds.

The invention also encompasses a compound selected from the following group:

{4-[(5-Chloro-4-pyrazolo[1,5-a]pyridin-3-yl-1,3-thiazol-2-yl)carbonyl]piperazin-2-yl}methanol;

3-(5-Chloro-2-{[2-(difluoromethyl)piperazin-1-yl]carbonyl}-1,3-thiazol-4-yl)pyrazolo[1,5-a]pyridine;

{4-[(5-Chloro-4-pyrazolo[1,5-a]pyridin-3-yl-1,3-thiazol-2-yl)carbonyl]morpholin-3-yl}methanol;

5-Chloro-N-(4-hydroxy-1,1-dioxidotetrahydro-3-thienyl)-4-pyrazolo[1,5-a]pyridin-3-yl-1,3-thiazole-2-carboxamide;

3-(5-Chloro-2-[2-(trifluoromethyl)piperazin-1-yl]carbonyl-1,3-thiazol-4-yl)pyrazolo[1,5-a]pyridine;

(3R,4R)-1-[(5-Chloro-4-pyrazolo[1,5-a]pyridin-3-yl-1,3-thiazol-2-yl)carbonyl]-3-fluoropiperidin-4-amine;

(3S,4R)-1-[(5-Chloro-4-pyrazolo[1,5-a]pyridin-3-yl-1,3-thiazol-2-yl)carbonyl]-3-fluoropiperidin-4-amine;

N-[(3R,4R)-4-amino-1-benzylpyrrolidin-3-yl]-5-chloro-4-pyrazolo[1,5-a]pyridin-3-yl-1,3-thiazole-2-carboxamide;

2-[(5-Chloro-4-pyrazolo[1,5-a]pyridin-3-yl-1,3-thiazol-2-yl)carbonyl]-2,3-dihydro-1H-spiro[isoquinoline-4,4'-piperidine];

5-Chloro-N-[(4-phenylpiperidin-4-yl)methyl]-4-pyrazolo[1,5-a]pyridin-3-yl-1,3-thiazole-2-carboxamide;

5-Chloro-N-(2,3-dihydrospiro[indene-1,4'-piperidin]-3-yl)-4-pyrazolo[1,5-a]pyridin-3-yl-1,3-thiazole-2-carboxamide;

5-Chloro-N-[(3S)-1-methylpyrrolidin-3-yl]-4-pyrazolo[1,5-a]pyridin-3-yl-1,3-thiazole-2-carboxamide;

5-Chloro-4-pyrazolo[1,5-a]pyridin-3-yl-N-(1,2,3,4-tetrahydroisoquinolin-1-ylmethyl)-1,3-thiazole-2-carboxamide;

{3-Amino-1-[(5-chloro-4-pyrazolo[1,5-a]pyridin-3-yl-1,3-thiazol-2-yl)carbonyl]pyrrolidin-3-yl}methanol;

5-Chloro-N-piperidin-3-yl-4-pyrazolo[1,5-a]pyridin-3-yl-1,3-thiazole-2-carboxamide;

1-[(5-Chloro-4-pyrazolo[1,5-a]pyridin-3-yl-1,3-thiazol-2-yl)carbonyl]pyrrolidin-3-amine;

3-[5-Chloro-2-(piperazin-1-ylcarbonyl)-1,3-thiazol-4-yl]pyrazolo[1,5-a]pyridine;

N-(2-Aminoethyl)-5-chloro-N-methyl-4-pyrazolo[1,5-a]pyridin-3-yl-1,3-thiazole-2-carboxamide;

N-(2-Aminoethyl)-5-chloro-N-ethyl-4-pyrazolo[1,5-a]pyridin-3-yl-1,3-thiazole-2-carboxamide;

1-[(5-Chloro-4-pyrazolo[1,5-a]pyridin-3-yl-1,3-thiazol-2-yl)carbonyl]-N-methylpyrrolidin-3-amine;

3-{5-Chloro-2-[(2-methylpiperazin-1-yl)carbonyl]-1,3-thiazol-4-yl}pyrazolo[1,5-a]pyridine;

N-[(1-Aminocyclopentyl)methyl]-5-chloro-4-pyrazolo[1,5-a]pyridin-3-yl-1,3-thiazole-2-carboxamide;

N-[(1-Aminocyclohexyl)methyl]-5-chloro-4-pyrazolo[1,5-a]pyridin-3-thiazole-2-carboxamide;

1-[(5-Chloro-4-pyrazolo-[1,5-a]pyridin-3-yl-1,3-thiazol-2-yl)carbonyl]-1,2,3,4-tetrahydroquinolin-3-amine;

N-(2-Amino-2-phenylethyl)-5-chloro-4-pyrazolo[1,5-a]pyridin-3-yl-1,3-thiazole-2-carboxamide;

N-(2-Aminoethyl)-5-chloro-4-pyrazolo[1,5-a]pyridin-3-yl-1,3-thiazole-2-carboxamide;

5-Chloro-4-pyrazolo[1,5-a]pyridin-3-yl-N-pyrrolidin-3-yl-1,3-thiazole-2-carboxamide;

3-{5-Chloro-2-[(3-methylpiperazin-1-yl)carbonyl]-1,3-thiazol-4-yl}pyrazolo[1,5-a]pyridine;

N-(3-Aminocyclohexyl)-5-chloro-4-pyrazolo[1,5-a]pyridin-3,3-thiazole-2-carboxamide;

3-{5-Chloro-2-[(3-methylpiperazin-1-yl)carbonyl]-1,3-thiazol-4-yl}pyrazolo[1,5-a]pyridine;

N-(3-Aminocyclohexyl)-5-chloro-4-pyrazolo[1,5-a]pyridin-3-yl-1,3-thiazole-2-carboxamide;

1-{1-[(5-Chloro-4-pyrazolo[1,5-a]pyridin-3-yl-1,3-thiazol-2-yl)carbonyl]-4-phenylpiperidin-4-yl}methanamine;

N-(4-Amino-1,1-dioxidotetrahydro-3-thienyl)-5-chloro-4-pyrazolo[1,5-a]pyridin-3-yl-1,3-thiazole-2-carboxamide;

N-(2-Amino-2-methylpropyl)-5-chloro-4-pyrazolo[1,5-a]pyridin-3-yl-1,3-thiazole-2-carboxamide;

5-Chloro-N-(2-oxopiperidin-3-yl)-4-pyrazolo[1,5-a]pyridin-3-yl-1,3-thiazole-2-carboxamide;

N-[(1S,2R)-2-aminocyclopentyl]-5-chloro-4-pyrazolo[1,5-a]pyridin-3-yl-1,3-thiazole-2-carboxamide;

N-[(1-aminocycloheptyl)methyl]-5-chloro-4-pyrazolo[1,5-a]pyridin-3-yl-1,3-thiazole-2-carboxamide;

N-[(1R,6S)-6-Amino-2,2-difluorocyclohexyl]-5-chloro-4-pyrazolo[1,5-a]pyridin-3-yl-1,3-thiazole-2-carboxamide;

5-Chloro-N-(1-methyl-2-oxopyrrolidin-3-yl)-4-pyrazolo[1,5-a]pyridin-3-yl-1,3-thiazole-2-carboxamide;

5-Chloro-N-(3,3-difluorocyclopentyl)-4-pyrazolo[1,5-a]pyridin-3-yl-1,3-thiazole-2-carboxamide;

N-(2-Azetidin-1-yl-3,3,3-trifluoropropyl)-5-chloro-4-pyrazolo[1,5-a]pyridin-3-yl-1,3-thiazole-2-carboxamide;

3-[5-Chloro-2-(morpholin-4-ylcarbonyl)-1,3-thiazol-4-yl]pyrazolo[1,5-a]pyridine;

3-{5-Chloro-2-[(2,6-dimethylmorpholin-4-yl)carbonyl]-1,3-thiazol-4-yl}pyrazolo[1,5-a]pyridine;
3-{5-Chloro-2-[(4-methylpiperazin-1-yl)carbonyl]-1,3-thiazol-4-yl}pyrazolo[1,5-a]pyridine;
5-Chloro-N-(2-morpholin-4-ylethyl)-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]piperidin-4-ol;
1-[(5-Chloro-4-pyrazolo[1,5-a]pyridin-3-yl-1,3-thiazol-2-yl)carbonyl]-N,N-dimethylpiperidin-4-amine;
5-Chloro-N-[1-(hydroxymethyl)-2-methylpropyl]-4-pyrazolo[1,5-a]pyridin-3-yl-1,3-thiazole-2-carboxamide;
Diethyl {1-[(5-chloro-4-pyrazolo[1,5-a]pyridin-3-yl-1,3-thiazol-2-yl)carbonyl]piperidin-4-yl}phosphonate;
5-Chloro-N-(2-hydroxycyclopentyl)-4-pyrazolo[1,5-a]pyridin-3-yl-1,3-thiazole-2-carboxamide;
5-Chloro-N-(2,3-dihydroxypropyl)-N-methyl-4-pyrazolo[1,5-a]pyridin-3-yl-1,3-thiazole-2-carboxamide;
5-Chloro-N-(2-hydroxy-2-methylpropyl)-4-pyrazolo[1,5]pyridin-3-yl-1,3-thiazole-2-carboxamide;
1-[(5-Chloro-4-pyrazolo[1,5-a]pyridin-3-yl-1,3-thiazol-2-yl)carbonyl]-N,N-dimethylpiperidin-3-amine;
5-Chloro-N-(2-oxopyrrolidin-3-yl)-4-pyrazolo[1,5-a]pyridin-3-yl-1,3-thiazole-2-carboxamide;
5-Chloro-N-[(3R)-1-isopropylpyrrolidin-3-yl]-4-pyrazolo[1,5-a]pyridin-3-yl-1,3-thiazole-2-carboxamide;
5-Chloro-N-[(3S)-1-isopropylpyrrolidin-3-yl]-4-pyrazolo[1,5-a]pyridin-3-yl-1,3-thiazole-2-carboxamide;
5-Chloro-N-[2-(dimethylamino)-3,3,3-trifluoropropyl]-4-pyrazolo[1,5-d]pyridin-3-yl-1,3-thiazole-2-carboxamide;
5-Chloro-4-pyrazolo[1,5-a]pyridin-3-yl-N-[3,3,3-trifluoro-2-(3-fluoroazetidin-1-yl)propyl]-1,3-thiazole-2-carboxamide;
5-Chloro-N-(4-hydroxy-1,1-dioxidotetrahydro-3-thienyl)-4-pyrazolo[1,5-a]pyridin-3-yl-1,3-thiazole-2-carboxamide;
(2S)-2-Anilino-2-phenylethyl 5-chloro-4-pyrazolo[1,5-a]pyridin-3-yl-1,3-thiazole-2-carboxylate;
(2S)-2-Anilinopropyl 5-chloro-4-pyrazolo[1,5-a]pyridin-3-yl-1,3-thiazole-2-carboxylate;
5-Chloro-N-[(1S)-2-hydroxy-1-methylethyl]-N-phenyl-4-pyrazolo[1,5-a]pyridin-3-yl-1,3-thiazole-2-carboxamide;
5-Chloro-N-phenyl-4-pyrazolo[1,5-a]pyridin-3-yl-N-(2,2,2-trifluoroethyl)-1,3-thiazole-2-carboxamide;
5-Chloro-N-isopropyl-4-pyrazolo[1,5-a]pyridin-3-yl-1,3-thiazole-2-carboxamide;
5-Chloro-N-ethyl-N-methyl-4-pyrazolo[1,5-a]pyridin-3-yl-1,3-thiazole-2-carboxamide;
5-Chloro-N-(2-hydroxyethyl)-4-pyrazolo[1,5-a]pyridin-3-yl-1,3-thiazole-2-carboxamide;
5-Chloro-N-ethyl-4-pyrazolo[1,5-a]pyridin-3-yl-1,3-thiazole-2-carboxamide;
5-Chloro-N-(2-methoxyethyl)-4-pyrazolo[1,5-a]pyridin-3-yl-1,3-thiazole-2-carboxamide;
3-[5-Chloro-2-(piperidin-1-ylcarbonyl)-1,3-thiazol-4-yl]pyrazolo[1,5-a]pyridine;
5-Chloro-4-pyrazolo[1,5-a]pyridin-3-yl-N-pyridin-3-yl-1,3-thiazole-2-carboxamide;
5-Chloro-N-cyclohexyl-4-pyrazolo[1,5-a]pyridin-3-yl-1,3-thiazole-2-carboxamide;
N-Benzyl-5-chloro-4-pyrazolo[1,5-a]pyridin-3-yl-1,3-thiazole-2-carboxamide;
5-Chloro-4-pyrazolo[1,5-a]pyridin-3-yl-N-(pyridin-3-ylmethyl)-1,3-thiazole-2-carboxamide;
5-Chloro-4-pyrazolo[1,5-a]pyridin-3-yl-N-(2-thienylmethyl)-1,3-thiazole-2-carboxamide;
5-Chloro-4-pyrazolo[1,5-a]pyridin-3-yl-N-(2-pyrrolidin-1-ylethyl)-1,3-thiazole-2-carboxamide;
5-Chloro-1-(2,6-dimethylphenyl)-4-pyrazolo[1,5-a]pyridin-3-yl-1,3-thiazole-2-carboxamide;
3-{2-[(4-Acetylpiperazin-1-yl)carbonyl]-5-chloro-1,3-thiazol-4-yl}pyrazolo[1,5-a]pyridine;
5-Chloro-N-(3-phenylpropyl)-4-pyrazolo[1,5-a]pyridin-3-yl-1,3-thiazole-2-carboxamide;
5-Chloro-N-(3-chlorobenzyl)-4-pyrazolo[1,5-a]pyridin-3-yl-1,3-thiazole-2-carboxamide;
5-Chloro-4-pyrazolo[1,5-a]pyridin-3-yl-N-quinolin-7-yl-1,3-thiazole-2-carboxamide;
5-Chloro-4-pyrazolo[1,5-a]pyridin-3-yl-N-[4-(trifluoromethyl)benzyl]-1,3-thiazole-2-carboxamide;
3-{2-[(4-Benzylpiperidin-1-yl)carbonyl]-5-chloro-1,3-thiazol-4-yl}pyrazolo[1,5-a]pyridine;
3-(5-Chloro-2-{[4-(3-methoxyphenyl)piperazin-1-yl]carbonyl}-1,3-thiazol-4-yl)pyrazolo[1,5-a]pyridine;
5-Chloro-N-ethyl-N-phenyl-4-pyrazolo[1,5-a]pyridin-3-yl-1,3-thiazole-2-carboxamide;
5-Chloro-N-isopropyl-N-phenyl-4-pyrazolo[1,5-a]pyridin-3-yl-1,3-thiazole-2-carboxamide;
N-(2-Anilinocyclohexyl)-5-chloro-4-pyrazolo[1,5-a]pyridin-3-yl-1,3-thiazole-2-carboxamide;
5-Chloro-N-methyl-N-(3-methylphenyl)-4-pyrazolo[1,5-a]pyridin-3-yl-1,3-thiazole-2-carboxamide;
3-(5-Chloro-2-{[3-(methylsulfonyl)pyrrolidin-1-yl]carbonyl}-1,3-thiazol-4-yl)pyrazolo[1,5-a]pyridine;
N-[(1R)-1-(Aminomethyl)-2,2,2-trifluoroethyl]-5-chloro-4-pyrazolo[1,5-a]pyridin-3-yl-1,3-thiazole-2-carboxamide;
N-(2-Aminoethoxy)-5-chloro-4-pyrazolo[1,5-a]pyridin-3-yl-1,3-thiazole-2-carboxamide;
N-[(1S)-1-(Aminomethyl)-2,2,2-trifluoroethyl]-5-chloro-4-pyrazolo[1,5-a]pyridin-3-yl-1,3-thiazole-2-carboxamide;
5-Chloro-N-(2-hydroxyethoxy)-4-pyrazolo[1,5-a]pyridin-3-yl-1,3-thiazole-2-carboxamide;
N-(2-Anilinocyclohexyl)-5-chloro-4-pyrazolo[1,5-a]pyridin-3-yl-1,3-thiazole-2-carboxamide;
5-Chloro-N-(2,4-difluorophenyl)-N-methyl-4-pyrazolo[1,5-a]pyridin-3-yl-1,3-thiazole-2-carboxamide;
5-Chloro-N-(2,5-difluorophenyl)-N-methyl-4-pyrazolo[1,5-a]pyridin-3-yl-1,3-thiazole-2-carboxamide;
5-Chloro-N-(2,3-difluorophenyl)-N-methyl-4-pyrazolo[1,5-a]pyridin-3-yl-1,3-thiazole-2-carboxamide;
5-Chloro-N-(4-chlorophenyl)-N-methyl-4-pyrazolo[1,5-a]pyridin-3-yl-1,3-thiazole-2-carboxamide;
N-(3-Aminophenyl)-5-chloro-N-methyl-4-pyrazolo[1,5-a]pyridin-3-yl-1,3-thiazole-2-carboxamide;
5-Chloro-N-methyl-N-(4-methylphenyl)-4-pyrazolo[1,5-a]pyridin-3-yl-1,3-thiazole-2-carboxamide;
5-Chloro-N-methyl-4-pyrazolo[1,5-a]pyridin-3-yl-N-pyridin-2-yl-1,3-thiazole-2-carboxamide;
5-Chloro-N-(2,6-difluorophenyl)-N-methyl-4-pyrazolo[1,5-a]pyridin-3-yl-1,3-thiazole-2-carboxamide;
5-Chloro-N-methyl-N-(3-methylphenyl)-4-pyrazolo[1,5-a]pyridin-3-yl-1,3-thiazole-2-carboxamide;
5-Chloro-4-pyrazolo[1,5-a]pyridin-3-yl-N-(2,2,2-trifluoroethyl)-1,3-thiazole-2-carboxamide;
5-Chloro-N-(3-hydroxyphenyl)-N-methyl-4-pyrazolo[1,5-a]pyridin-3-yl-1,3-thiazole-2-carboxamide;
N-[(1R,6R)-2-Aminocyclohexyl]-5-chloro-4-[(6-trifluoromethyl)pyrazolo[1,5-a]pyridin-3-yl]-1,3-thiazole-2-carboxamide;
5-Chloro-N-(2-chlorophenyl)-N-methyl-4-pyrazolo[1,5-a]pyridin-3-yl-1,3-thiazole-2-carboxamide;
5-Chloro-N-methyl-N-(2-methylphenyl)-4-pyrazolo[1,5-a]pyridin-3-yl-1,3-thiazole-2-carboxamide;
5-Chloro-N-(4-fluorophenyl)-N-methyl-4-pyrazolo[1,5-a]pyridin-3-yl-1,3-thiazole-2-carboxamide;

5-Chloro-N-(3-chlorophenyl)-N-methyl-4-pyrazolo[1,5-a]pyridin-3-yl-1,3-thiazole-2-carboxamide;
5-Chloro-N-(3-fluorophenyl)-N-methyl-4-pyrazolo[1,5-a]pyridin-3-yl-1,3-thiazole-2-carboxamide;
N-[(1S,6S)-2-Aminocyclohexyl]-5-chloro-4-[(6-trifluoromethyl)pyrazolo[1,5-a]pyridin-3-yl]-1,3-thiazole-2-carboxamide;
5-Chloro-N-(2-chlorophenyl)-N-methyl-4-pyrazolo[1,5-a]pyridin-3-yl-1,3-thiazole-2-carboxamide;
{4-[(5-Chloro-4-pyrazolo[1,5-a]pyridin-3-yl-1,3-thiazol-2-yl)carbonyl]morpholin-2-yl}methanol;
1-[(5-Chloro-4-pyrazolo[1,5-a]pyridin-3-yl-1,3-thiazol-2-yl)carbonyl]-2,3,4,5-tetrahydro-1H-1,4-benzodiazepine;
5-Chloro-N-(3-fluorophenyl)-N-methyl-4-pyrazolo[1,5-a]pyridin-3-yl-1,3-thiazole-2-carboxamide;
N-[1-(Aminomethyl)-6-fluoro-2,3-dihydro-1H-inden-1-yl]-5-chloro-4-pyrazolo[1,5-a]pyridin-3-yl-1,3-thiazole-2-carboxamide;
5-Chloro-N-methyl-N-phenyl-4-pyrazolo[1,5-a]pyridin-3-yl-1,3-thiazole-2-carboxamide;
N-[(1R,6S)-6-amino-2,2-difluorocyclohexyl]-4-pyrazolo[1,5-a]pyridin-3-yl-1,3-thiazole-2-carboxamide;
3-[2-(Piperidin-1-ylcarbonyl)-1,3-thiazol-4-yl]pyrazolo[1,5-a]pyridine;
N-[1-(Aminomethyl)-5-fluoro-2,3-dihydro-1H-inden-1-yl]-5-chloro-4-pyrazolo[1,5-a]pyridin-3-yl-1,3-thiazole-2-carboxamide;
N-[1-(Aminomethyl)-4-fluoro-2,3-dihydro-1H-inden-1-yl]-5-chloro-4-pyrazolo[1,5-a]pyridin-3-yl-1,3-thiazole-2-carboxamide;
N-[1-(Aminomethyl)-2,3-dihydro-1H-inden-1-yl]-5-chloro-4-pyrazolo[1,5-a]pyridin-3-yl-1,3-thiazole-2-carboxamide;
N-(2-Amino-3,3,3-trifluoro-1-phenylpropyl)-5-chloro-4-pyrazolo[1,5-a]pyridin-3-yl-1,3-thiazole-2-carboxamide;
N-(2-Amino-3,3,3-trifluoro-1-phenylpropyl)-5-chloro-4-pyrazolo[1,5-a]pyridin-3-yl-1,3-thiazole-2-carboxamide;
N-[(1S)-1-(Aminomethyl)-2,2,2-trifluoro-1-methylethyl]-5-chloro-4-pyrazolo[1,5-a]pyridin-3-yl-1,3-thiazole-2-carboxamide;
5-Chloro-N-(2-fluorophenyl)-N-methyl-4-pyrazolo[1,5-a]pyridin-3-yl-1,3-thiazole-2-carboxamide;
N-[(1R,2S)-2-amino-6,6-difluoro-2-methylcyclohexyl]-5-chloro-4-(pyrazolo[1,5]pyridin-3-yl)-1,3-thiazole-2-carboxamide;
5-Chloro-N-[(1R,6S)-2,2-difluoro-6-hydroxycyclohexyl]-4-(pyrazolo[1,5-a]pyridin-3-yl)-1,3-thiazole-2-carboxamide;
N-[(1R,6S)-6-Amino-2,2-difluorocyclohexyl]-5-chloro-4-(6-iodopyrazolo[1,5-a]pyridin-3-yl)-1,3-thiazole-2-carboxamide;
N-[(1R,6S)-6-Amino-2,2-difluorocyclohexyl]-4-(6-bromopyrazolo[1,5-a]pyridin-3-yl)-5-chloro-1,3-thiazole-2-carboxamide;
N-[(1R,6S)-6-Amino-2,2-difluorocyclohexyl]-5-chloro-4-[5-(trifluoromethyl)pyrazolo[1,5-a]pyridin-3-yl]-1,3-thiazole-2-carboxamide;
N-[(1R,6S)-6-Amino-2,2-difluorocyclohexyl]-5-chloro-4-[(6-trifluoromethyl)pyrazolo[1,5-a]pyridin-3-yl]-1,3-thiazole-2-carboxamide;
N-[(1R,6S)-6-Amino-2,2-difluorocyclohexyl]-5-chloro-4-(6-methoxypyrazolo[1,5-a]pyridin-3-yl)-1,3-thiazole-2-carboxamide;
N-[(1R,6S)-6-Amino-2,2-difluorocyclohexyl]-5-chloro-4-(6-ethylpyrazolo[1,5-a]pyridin-3-yl)-1,3-thiazole-2-carboxamide;
N-[(1R,6S)-6-Amino-2,2-difluorocyclohexyl]-5-chloro-4-(5-cyanopyrazolo[1,5-a]pyridin-3-yl)-1,3-thiazole-2-carboxamide;
3-[2-({[(1R,6S)-6-Amino-2,2-difluorocyclohexyl]amino}carbonyl)-5-chloro-1,3-thiazol-4-yl]pyrazolo[1,5-a]pyridine-5-carboxamide;
N-[(1R,6S)-6-amino-2,2-difluorocyclohexyl]-5-chloro-4-(6-fluoropyrazolo[1,5-a]pyridin-3-yl)-1,3-thiazole-2-carboxamide;
N-[(1R,6S)-6-amino-2,2-difluorocyclohexyl]-5-chloro-4-(5-chloropyrazolo[1,5-a]pyridin-3-yl)-1,3-thiazole-2-carboxamide;
N-[(1R,6S)-6-Amino-2,2-difluorocyclohexyl]-5-chloro-4-(5-methylpyrazolo[1,5-a]pyridin-3-yl)-1,3-thiazole-2-carboxamide;
N-[(1R,6S)-6-Amino-2,2-difluorocyclohexyl]-5-chloro-4-(5-chloro-6-fluoropyrazolo[1,5-a]pyridin-3-yl)-1,3-thiazole-2-carboxamide;
N-[(1R,6S)-6-Amino-2,2-difluorocyclohexyl]-4-(6-ethylpyrazolo[1,5-a]pyridin-3-yl)-1,3-thiazole-2-carboxamide;
N-[(1R,6S)-6-Amino-2,2-difluorocyclohexyl]-4-(5-chloro-6-fluoropyrazolo[1,5-a]pyridin-3-yl)-1,3-thiazole-2-carboxamide;
N-[(1R,6S)-6-Amino-2,2-difluorocyclohexyl]-4-(6-methoxypyrazolo[1,5-a]pyridin-3-yl)-1,3-thiazole-2-carboxamide;
N-[(1R,6S)-6-Amino-2,2-difluorocyclohexyl]-4-(5-cyanopyrazolo[1,5-a]pyridin-3-yl)-1,3-thiazole-2-carboxamide;
N-[(1R,6S)-6-Amino-2,2-difluorocyclohexyl]-4-(6-iodopyrazolo[1,5-a]pyridin-3-yl)-1,3-thiazole-2-carboxamide;
N-[(1R,6S)-6-Amino-2,2-difluorocyclohexyl]-4-(6-isopropenylpyrazolo[1,5-a]pyridin-3-yl)-1,3-thiazole-2-carboxamide;
N-[(1R,6S)-6-Amino-2,2-difluorocyclohexyl]-4-(5-chloropyrazolo[1,5-a]pyridin-3-yl)-1,3-thiazole-2-carboxamide;
N-[(1R,6S)-6-Amino-2,2-difluorocyclohexyl]-4-(6-cyanopyrazolo[1,5-a]pyridin-3-yl)-1,3-thiazole-2-carboxamide;
N-[(1R,6S)-6-Amino-2,2-difluorocyclohexyl]-4-[6-methoxy-5-(trifluoromethyl)pyrazolo[1,5-a]pyridin-3-yl]-1,3-thiazole-2-carboxamide;
N-[(1R,6S)-6-Amino-2,2-difluorocyclohexyl]-4-{6-[(trimethylsilyl)ethynyl]pyrazolo[1,5-a]pyridin-3-yl}-1,3-thiazole-2-carboxamide;
N-[(1R,6R)-6-Amino-2,2-difluorocyclohexyl]-5-chloro-4-(4,6-difluoropyrazolo[1,5-a]pyridin-3-yl)-1,3-thiazole-2-carboxamide;
N-[(1R,6S)-6-Amino-2,2-difluorocyclohexyl]-4-(4-chloro-6-methoxypyrazolo[1,5-a]pyridin-3-yl)-1,3-thiazole-2-carboxamide;
N-[(1R,6S)-6-Amino-2,2-difluorocyclohexyl]-4-(6-ethylpyrazolo[1,5-a]pyridin-3-yl)-1,3-thiazole-2-carboxamide;
N-[(1R,6S)-6-Amino-2,2-difluorocyclohexyl]-4-(5-chloro-6-fluoropyrazolo[1,5-a]pyridin-3-yl)-1,3-thiazole-2-carboxamide;
N-[(1R,6S)-6-Amino-2,2-difluorocyclohexyl]-4-(6-methoxypyrazolo[1,5-a]pyridin-3-yl)-1,3-thiazole-2-carboxamide;
N-[(1R,6S)-6-Amino-2,2-difluorocyclohexyl]-5-chloro-4-(6-cyclopropylpyrazolo[1,5-a]pyridin-3-yl)-1,3-thiazole-2-carboxamide;

N-[(1R,6S)-6-Amino-2,2-difluorocyclohexyl]-5-ethyl-4-(6-fluoropyrazolo[1,5-a]pyridin-3-yl)thiophene-2-carboxamide;

N-[(1R,6S)-6-Amino-2,2-difluorocyclohexyl]-5-isopropyl-4-pyrazolo[1,5-a]pyridin-3-yl-1,3-thiazole-2-carboxamide;

N-[(1R,6R)-6-Amino-2,2-difluorocyclohexyl]-5-isopropyl-4-pyrazolo[1,5-a]pyridin-3-yl-1,3-thiazole-2-carboxamide;

N-[(1R,6S)-6-amino-2,2-difluorocyclohexyl]-5-ethyl-4-[6-(trifluoromethyl)pyrazolo[1,5-a]pyridin-3-yl]thiophene-2-carboxamide;

N-[(1R,6S)-6-Amino-2,2-difluorocyclohexyl]-5-ethyl-4-pyrazolo[1,5-a]pyridin-3-yl-1,3-thiazole-2-carboxamide;

N-[(1R,6S)-6-Amino-2,2-difluorocyclohexyl]-5-methyl-4-pyrazolo[1,5-a]pyridin-3-yl-1,3-thiazole-2-carboxamide;

N-[(1R,6S)-6-Amino-2,2-difluorocyclohexyl]-4-(6-fluoropyrazolo[1,5-a]pyridin-3-yl)-5-methyl-1,3-thiazole-2-carboxamide;

N-[(1R,6S)-6-Amino-2,2-difluorocyclohexyl]-4-(4,6-difluoropyrazolo[1,5-a]pyridin-3-yl)-5-methylthiophene-2-carboxamide;

N-[(trans)-4-Amino-1,1-dioxidotetrahydro-2H-thiopyran-3-yl]-5-methyl-4-(pyrazolo[1,5-a]pyridin-3-yl) thiophene-2-carboxamide;

N-[(cis)-4-Amino-1,1-dioxidotetrahydro-2H-thiopyran-3-yl]-5-methyl-4-(pyrazolo[1,5-a]pyridin-3-yl) thiophene-2-carboxamide;

N-[(1R,6S)-6-Amino-2,2-difluorocyclohexyl]-5-ethyl-4-[6-(trifluoromethyl)pyrazolo[1,5-a]pyridin-3-yl]thiophene-2-carboxamide;

N-[(1R,6S)-6-Amino-2,2-difluorocyclohexyl]-5-ethyl-4-(6-fluoropyrazolo[1,5-a]pyridin-3-yl) thiophene-2-carboxamide;

N-[(1R,6S)-6-Amino-2,2-difluorocyclohexyl]-4-(4,6-difluoropyrazolo[1,5-a]pyridin-3-yl)-5-methylthiophene-2-carboxamide;

N-[(trans)-4-amino-1,1-dioxidotetrahydro-2H-thiopyran-3-yl]-5-chloro-4-(pyrazolo[1,5-a]pyridin-3-yl) thiophene-2-carboxamide;

N-[(cis)-4-amino-1,1-dioxidotetrahydro-2H-thiopyran-3-yl]-5-chloro-4-(pyrazolo[1,5-a]pyridin-3-yl) thiophene-2-carboxamide;

N-[(trans)-3-amino-1,1-dioxidotetrahydro-2H-thiopyran-4-yl]-5-chloro-4-(pyrazolo[1,5-a]pyridin-3-yl) thiophene-2-carboxamide;

N-[(cis)-3-amino-1,1-dioxidotetrahydro-2H-thiopyran-4-yl]-5-chloro-4-(pyrazolo[1,5-a]pyridin-3-yl) thiophene-2-carboxamide;

N-[(1R,6R)-6-Amino-2,2-difluorocyclohexyl]-5-(phenylethynyl)-4-pyrazolo[1,5-a]pyridin-3-yl-1,3-thiazole-2-carboxamide;

N-[(1R,6R)-6-Amino-2,2-difluorocyclohexyl]-5-(3-hydroxy-3-methylbut-1-yn-1-yl)-4-pyrazolo[1,5-a]pyridin-3-yl-1,3-thiazole-2-carboxamide;

N-[(1R,6R)-6-Amino-2,2-difluorocyclohexyl]-5-ethynyl-4-pyrazolo[1,5-a]pyridin-3-yl-1,3-thiazole-2-carboxamide;

N-[(1R,6R)-6-Amino-2,2-difluorocyclohexyl]-5-(cyclopropylethynyl)-4-pyrazolo[1,5-a]pyridin-3-yl-1,3-thiazole-2-carboxamide;

N-[(1R,6R)-6-Amino-2,2-difluorocyclohexyl]-5-(3-methoxyprop-1-yn-1-yl)-4-pyrazolo[1,5-a]pyridin-3-yl-1,3-thiazole-2-carboxamide;

N-[(1R,6R)-6-amino-2,2-difluorocyclohexyl]-5-cyclopent-1-en-1-yl-4-pyrazolo[1,5-a]pyridin-3-yl-1,3-thiazole-2-carboxamide;

N-[(1R,6S)-6-Amino-2,2-difluorocyclohexyl]-5-isopropenyl-4-pyrazolo[1,5-a]pyridin-3-yl-1,3-thiazole-2-carboxamide;

N-[(1R,6S)-6-Amino-2,2-difluorocyclohexyl]-5-isopropenyl-4-[6-(trifluoromethyl)pyrazolo[1,5-a]pyridin-3-yl]-1,3-thiazole-2-carboxamide;

N-[(1R,6S)-6-Amino-2,2-difluorocyclohexyl]-4-pyrazolo[1,5-a]pyridin-3-yl-5-vinyl-1,3-thiazole-2-carboxamide;

N-[(1R,6S)-6-Amino-2,2-difluorocyclohexyl]-4-(6-fluoropyrazolo[1,5-a]pyridin-3-yl)-5-isopropenyl-1,3-thiazole-2-carboxamide;

N-[(1R,6R)-6-amino-2,2-difluorocyclohexyl]-5-[(1E)-but-1-en-1-yl]-4-pyrazolo[1,5-a]pyridin-3-yl-1,3-thiazole-2-carboxamide;

N-[(1R,6R)-6-Amino-2,2-difluorocyclohexyl]-4-pyrazolo pyridin-3-yl-5-vinyl-1,3-thiazole-2-carboxamide;

N-[(1R,6R)-6-amino-2,2-difluorocyclohexyl]-5-(2-methylprop-1-en-1-yl)-4-pyrazolo[1,5-a]pyridin-3-yl-1,3-thiazole-2-carboxamide;

N-[(1R,6R)-6-amino-2,2-difluorocyclohexyl]-5-[(E)-2-cyclohexylvinyl]-4-pyrazolo[1,5-a]pyridin-3-yl-1,3-thiazole-2-carboxamide;

N-[(1R,6R)-6-amino-2,2-difluorocyclohexyl]-5-[(E)-2-cyclopropylvinyl]-4-pyrazolo[1,5-a]pyridin-3-yl-1,3-thiazole-2-carboxamide;

N-[(1R,6S)-6-amino-2,2-difluorocyclohexyl]-5-cyclopropyl-4-pyrazolo[1,5-a]pyridin-3-yl-1,3-thiazole-2-carboxamide;

N-[(1R,6R)-6-amino-2,2-difluorocyclohexyl]-5-cyano-4-pyrazolo[1,5-a]pyridin-3-yl-1,3-thiazole-2-carboxamide;

N-[(1R,6S)-6-amino-2,2-difluorocyclohexyl]-5-(difluoromethyl)-4-pyrazolo[1,5-a]pyridin-3-ylthiophene-2-carboxamide;

N-[(1R,6S)-6-Amino-2,2-difluorocyclohexyl]-5-(difluoromethyl)-4-(6-fluoropyrazolo[1,5-a]pyridin-3-yl)-1,3-thiazole-2-carboxamide;

N-[(1R,6S)-6-Amino-2,2-difluorocyclohexyl]-5-(difluoromethyl)-4-[6-(trifluoromethyl)pyrazolo[1,5-a]pyridin-3-yl]-1,3-thiazole-2-carboxamide;

N-[(1R,6R)-6-Amino-2,2-difluorocyclohexyl]-5-nitro-4-pyrazolo[1,5-a]pyridin-3-yl-1,3-thiazole-2-carboxamide;

2-(Piperidin-1-ylcarbonyl)-4-pyrazolo[1,5-a]pyridin-3-yl-1,3-thiazol-5-amine; and N-[(1R,6S)-6-Amino-2,2-difluorocyclohexyl]-5-(dimethylamino)-4-pyrazolo[1,5-a]pyridin-3-yl-1,3-thiazole-2-carboxamide;

or a pharmaceutically acceptable salt of any of the foregoing compounds.

The invention also encompasses a compound according to Formula Ia

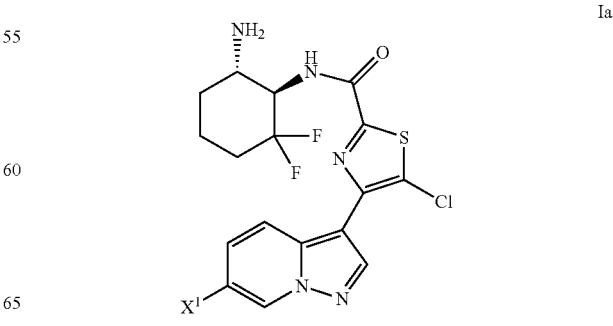

Ia or a pharmaceutically acceptable salt or hydrate thereof, wherein $X^1$ is selected from the group consisting of: H, halogen, $C_{1-6}$alkyl, $C_{2-6}$alkenyl, $C_{3-6}$cycloalkyl, $CF_3$, methoxy, CN, $CON(R^3)_2$, (trimethylsilyl)ethynyl, phenyl and a monocyclic or bicyclic ring system comprising up to 10 ring atoms, of which 1-3 are selected from N, O and S and the remainder are C, said phenyl and ring system bearing 0-3 substituents independently selected from halogen and $C_{1-4}$alkyl, optionally substituted with up to 3 halogen atoms.

The invention also encompasses a pharmaceutical composition comprising a compound of formula I or a pharmaceutically acceptable salt or hydrate thereof, and a pharmaceutically acceptable carrier.

The invention further provides a method for treatment or prevention of a neurodegenerative disease associated with hyperphosphorylation of tau in a human patient, said method comprising administering to that patient an effective amount of a compound of formula I as defined above, or a pharmaceutically acceptable salt or hydrate thereof.

Neurodegenerative diseases associated with hyperphosphorylation of tau include AD, frontotemporal dementia, Pick's disease and parkinsonism linked to chromosome 17 (FTDP-17).

In a further aspect, the invention provides a method for reducing the production of hyperphosphorylated tau in a human patient, said method comprising administering to said patient an effective amount of a compound of formula I as defined above or a pharmaceutically acceptable salt or hydrate thereof.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine.

The expression "$C_{3-x}$cycloalkyl" as used herein, where x is an integer greater than 3, refers to nonaromatic hydrocarbon ring systems containing from 3 to x ring atoms. Said systems may be monocyclic or bicyclic if the magnitude of x allows it. Examples include cyclopropyl, cyclobutyl, cyclopentyl, cyclohexyl, cycloheptyl, bicycloheptyl and decalinyl.

The expression "$C_{3-x}$cycloalkenyl" as used herein, means "$C_{3-x}$cycloalkyl" as defined above but containing at least one double bond.

Unless indicated otherwise, the term "bicyclic" includes bridged bicyclic and spiro-linked ring systems as well as fused ring systems. However, a bicyclic system in which one or both rings are aromatic is of necessity a fused ring system.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, trifluoroacetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds useful in the invention have one or more asymmetric centres, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

When a compound useful in the invention is capable of existing in tautomeric keto and enol forms, both of said forms are considered to be within the scope of the invention.

A nitrogen atom forming part of a heteroaryl ring may be in the form of the N-oxide. A sulphur atom forming part of a nonaromatic heterocycle may be in the form of the S-oxide or S,S-dioxide.

A heteroaryl group may be attached to the remainder of the molecule via a ring carbon or a ring nitrogen, provided that this is consistent with preservation of aromaticity.

In formula I, $X^1$ may represent a monocyclic or bicyclic ring system comprising up to 10 ring atoms, of which 1-3 are heteroatoms selected from N, O and S and the remainder are C. In the case of a bicyclic system comprising 2 or 3 heteroatoms, said heteroatoms may be confined to one of the rings or distributed over both of the rings. In the case of a bicyclic system, preferably at least one of the rings is aromatic, for example the ring which is bonded to the pyrazolopyridine system of formula I. In the case of a monocyclic system, the ring typically comprises 5 or 6 ring atoms and may be aromatic or nonaromatic, and in a particular embodiment such a ring is either aromatic or partially unsaturated.

Examples of aromatic monocyclic systems represented by $X^1$ include pyridine, pyrazole, imidazole, pyrrole, thiophene and furan.

Examples of nonaromatic monocyclic systems represented by $X^1$ include dihydropyridine and tetrahydropyridine.

Examples of bicyclic systems represented by $X^1$ include indole, benzofuran, quinoline, isoquinoline, 1H-pyrrolo[2,3-b]pyridine, 5,6-dihydro-4H-pyrrolo[1,2-b]pyrazole and 2,3-dihydro-1H-benzimidazole.

It will be apparent to those skilled in the art that a hydroxyl substituent on an unsaturated ring may be capable of tautomerising to a ketone. In such circumstances, both tautomers are to be considered equivalent. Thus, for example, 2-hydroxypyridine is considered equivalent to 2-oxo-1,2-dihydropyridine.

Specific examples of compounds in accordance with the invention are provided in the Examples hereinafter.

It will be apparent to those skilled in the art that individual compounds in accordance with formula I may be converted into other compounds in accordance with formula I using standard synthetic techniques. For example, compounds in which $X^1$ is a fluoro-substituted aromatic moiety may be treated with primary or secondary amines in DMF in the presence of alkali at elevated temperatures to provide the corresponding amino-substituted derivatives. Similarly, compounds in which $X^1$ comprises a dihydro- or tetrahydropyridine ring or similar may be N-alkylated using standard methods. Such transformations may also be carried out on intermediates in the synthesis of compounds of formula I.

Where they are not themselves commercially available, the starting materials and reagents described above may be obtained from commercially available precursors by means of well known synthetic procedures and/or the methods disclosed in the Examples section herein.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds of formula I are suitably administered to patients in the form a pharmaceutical composition comprising the active ingredient (i.e. the compound of formula I or pharmaceutically acceptable salt or hydrate thereof) and a pharmaceutically acceptable carrier, and said pharmaceutical compositions constitute a further aspect of the invention.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

In one embodiment of the invention, the compound of formula I is administered to a patient suffering from AD, FTDP-17, Pick's disease or frontotemporal dementia, in particular AD.

In an alternative embodiment of the invention, the compound of formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch, Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with nouns adjusted for age and education (Folstein et al., *J. Psych. Res.,* 12 (1975), 196-198, Anthony et al., *Psychological Med,* 12 (1982), 397-408; Cockrell et al., *Psychopharmacology,* 24 (1988), 689-692; Crum et al., *J. Am, Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry,* 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compound of formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which modulate the secretion of Aβ (including γ-secretase inhibitors, γ-secretase modulators and β-secretase inhibitors), compounds which inhibit the aggregation of Aβ, and antibodies which selectively bind to Aβ. Such additional compounds further include growth hormone secretagogues, e.g. as described in WO 2004/080459.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a (3-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ, including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which modulates the action of γ-secretase so as to selectively attenuate the production of Aβ(1-42). Compounds reported to show this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70), and compounds which modulate the activity of PPARα and/or PPARδ (WO 02/100836). Further examples of γ-secretase modulators are disclosed in WO 2005/054193, WO 2005/013985, WO 2005/108362, WO 2006/008558 and WO 2006/043064.

Alternatively, the amyloid modifier may be a compound which inhibits the aggregation of Aβ or otherwise attenuates is neurotoxicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors dm aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (Proteo-Tech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of formula I.

EXAMPLES

MARK 3 Assay

MARK3 activity was assayed in vitro using a Cdc25C biotinylated peptide substrate (Cell Signalling Technologies). The phosphopeptide product was quantitated using a Homogenous Time-Resolved Fluorescence (HTRF) assay system (Park et al., 1999, *Anal. Biochem.* 269:94-104). The reaction mixture contained 50 mM HEPES/Tris-HCl, pH 7.4; mM NaCl, 5 mM $MgCl_2$, 0.2 mM $NaVO_4$, 5 mM β-glycerol phosphate, 0.1% Tween-20, 2 mM dithiothreitol, 0.1% BSA, 10 μM ATP, 1 μM peptide substrate, and 10 nM recombinant MARK3 enzyme (University of Dundee) in a final volume of 12 μL. The buffer additionally contained protease inhibitor cocktail (Roche EDTA-free, 1 tab per 50 ml). The kinase reaction was incubated for 2 hours at 25° C., and then terminated with 3 μl Stop/Detection Buffer (50 mM HEPES, pH 7.0, 16.6 mM EDTA, 0.5M KF, 0.1% Tween-20, 0.1% BSA, 2 μg/ml $SLX^{ent}$ 665 (CISBIO), and 2 μg/mL $Eu^{3+}$ cryptate label antibody (CISBIO)). The reaction was allowed to equilibrate overnight at 0° C., and relative fluorescent units were read on an HTRF enabled plate reader (e.g. TECAN GENios Pro).

Inhibitor compounds were assayed in the reaction described above to determine compound $IC_{50}$s. Aliquots of compound dissolved in DMSO were added to the reaction wells in a third-log dilution series covering a range of 1 nM to 10 μM. Relative phospho substrate formation, read as HTRF fluorescence units, was measured over the range of compound concentrations and a titration curve generated.

The compounds described below gave $IC_{50}$ values of 1 μM or less, typically 500 nM or less, and in preferred cases 50 nM less, in the above assay. The following table provides $IC_{50}$ values in the above assay for representative examples:

| Example | $IC_{50}$ (nM) |
| --- | --- |
| 1 | 21 |
| 7 | 4 |
| 157 | 0.5 |
| 170 | 29 |
| 182 | 13 |
| 206 | 19 | pTau(S262) Cell Biochemical and Functional Assay

The cell biochemical potency of the below described MARK inhibitors was evaluated by measuring their ability to block the phosphorylation of Tau at 5262 in primary cell culture of rat cortical neurons induced by the action of Okadaic acid.

Reagents:
  Neurobasal (Invitrogen, cat. 21103-049)
  B27 (Invitrogen, cat. 17504-044)
  L-Glutamine (Invitrogen, cat. 25030-081)
  Penicillin-Streptomycin (Invitrogen, cat. 15140)
  Papain, sterile lyophilized (Worthington, cat. NC9212788)
    10 mL 1M Hepes added for 10× solution
  Tissue Culture plates:
    384 well: BD FALCON BD BIOCOAT Poly-D-Lysine Black/Clear Microtest, Tissue-Culture Treated Polystyrene (cat. 354663)
  E18 Primary Rat Cortical Cells: BrainBits, cat. cx2
  Stock Media (NB): Neurobasal+B-27 (1:50)+0.5 mM L-Glutamine+1% Pen/Strep Preparation of Isolated Neurons
  1. Store tissue at 4° C. (1-2 days) until ready to use.
  2. When ready to plate, make up 2 mL of enzymatic solution in Hibernate-Ca containing 1× papain. Filter sterile solution with 0.2 μm filter.
  3. Transfer 2 mL of medium from tissue tube into 15 mL falcon tube while not disturbing tissue. Save media.
  4. Add 2 mL enzymatic media (2) to tissue. Incubate for 30' at 37° C.
  5. Remove enzymatic solution while not disturbing tissue. Add back 1 mL of media from (3).
  6. Using pipettor with sterile plastic tip, triturate ~10 times until most of the cells are dispersed.
  7. Let undispersed pieces settle by gravity 1 minute,
  8. Transfer dispersed cells (supernatant) into 15 mL falcon tube containing 1 mL media from (3). Gently mix cells by swirling.
  9. Spin cells at 1,100 rpm for 1 minute. Remove supernatant.
  10. Flick tube to loosen cell pellet. Resuspend cells in 5 mL of NB.
  11. Transfer to new 50 mL falcon tube using 40 μm cell strainer. Rinse 15 mL falcon tube with 5 mL media, add to strainer.
  12. Count cells using hemacytometer.
  13. Dilute cells to 7,000 cells/100 μL/well in NB.
  14. Incubate cells at 37° C. with 5% $CO_2$.
    a. 4 DIV: Replace ½ volume (50 μL) NB per well.
    b. 6 DIV: Neurite Assay.

Tissue Culture/Compound Treatment
  Primary rat cortical neurons plated @ 6K cells/well in 384-well black/clear bottom Poly D-Lysine coated BD Falcon Biocoat plates.
    Media: Neurobasal+1×B27+2 mM L-Glutamine (+10% FBS) at time of plating
  Cells maintained at 37° C. and 5% $CO_2$ for *6 days in culture, w/½ media change every 3-4 days.
  Compound treatment:
    Prepare first plate: 200× compound in 100% DMSO with subsequent 3 fold serial dilution
    Prepare intermediate plate: 1:40 dilution of 200× compound in media (2.5% DMSO)
    Add 5× compound to cell in media at 1:5 dilution (0.5% final DMSO)
    Incubate for 30 min. at 37° C.

Okadaic Acid (OA) Treatment:
  Dilute OA stock (240 µM in 100% DMSO) to 6× final concentration in media (0.5% DMSO)
  Add 6×OA to cells at 1:6 dilution (200 nM final).
Incubate for 1.5 hrs. at 37° C.
Fix and Immunostaining
  Fix: 1% PFA, diluted in PBS
    Wash 1× with PBS, residual 30 ul/well.
  Add 30 µL/well warmed 2% PFA and incubate 30 min. at RT (1% PFA final)
  Wash 3× with PBS, 30 ul/well residual
  Permeabilize & Block.
    Add 30 µl/well PBS+0.2% Triton X-100+10% normal goat serum (0.1% Triton & 5% NGS final).
    Incubate 1 hr at RT or O/N at 4° C.
  Wash 3× with PBS, 30 µL/well residual
  Primary antibody: add 30 µL/well 2× final concentration antibody diluted in PBS
    Mouse anti-tau-3R
    Rabbit anti-tau-pS$^{262}$
    Incubate O/N at 4° C.
  Wash 4× with PBS, 30 µL/well residual
  Secondary antibody & nuclear staining: add 30 µL/well 2× final concentration stain diluted in PBS
    AlexaFluor goat anti mouse 488
    AlexaFluor goat anti rabbit 594
    Hoechst
    Incubate in dark 1 hr. at RT
  Wash 4× with PBS 30 µl/well residual, protect from light
  Acquire images in INCell Analyzer 1000 & Opera.
The compounds described below gave IC$_{50}$ values of 10 µM or less, typically 1000 nM or less, and in preferred cases 250 nM less, in the above assay measuring inhibition of phosphorylation of Tau at S262.

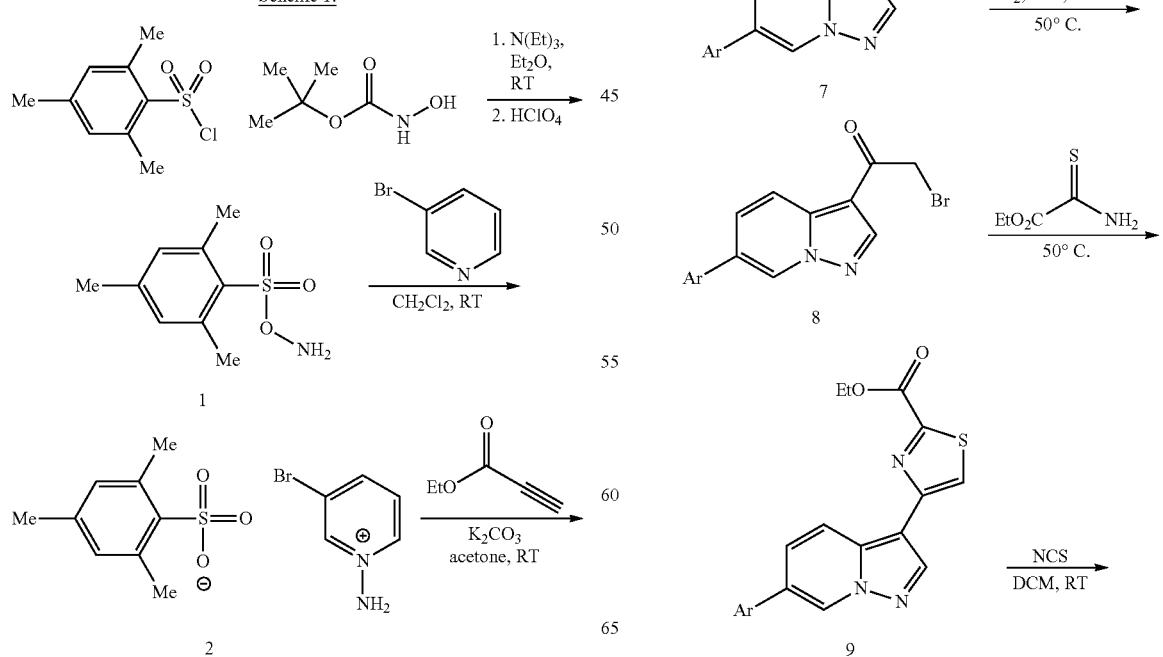

Scheme 1.

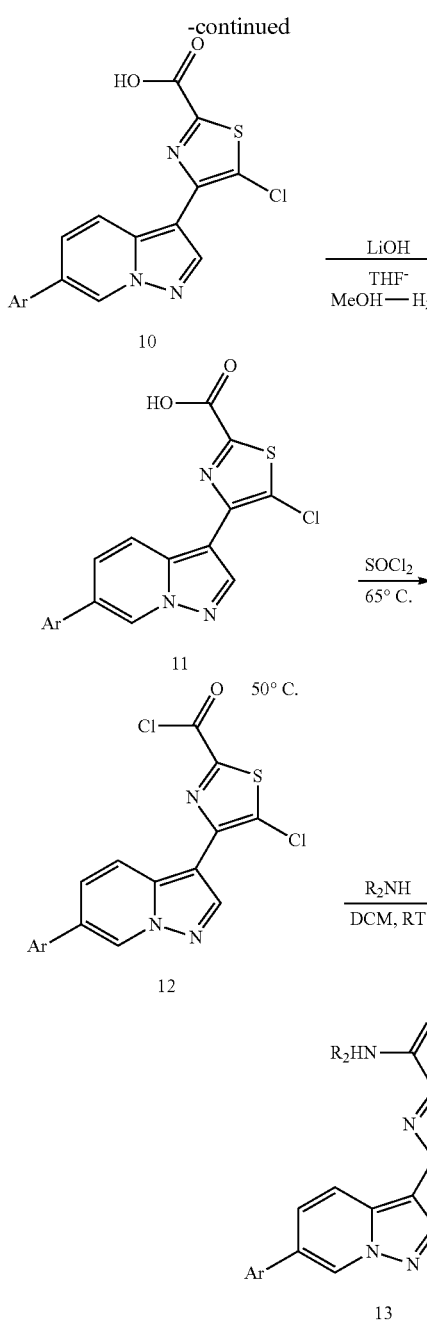

is accomplished via exposure to NCS to yield 10. A three step sequence of saponification to acid 11, acid chloride synthesis (12) and exposure to an amine, installs the final amide bond to yield target 13.

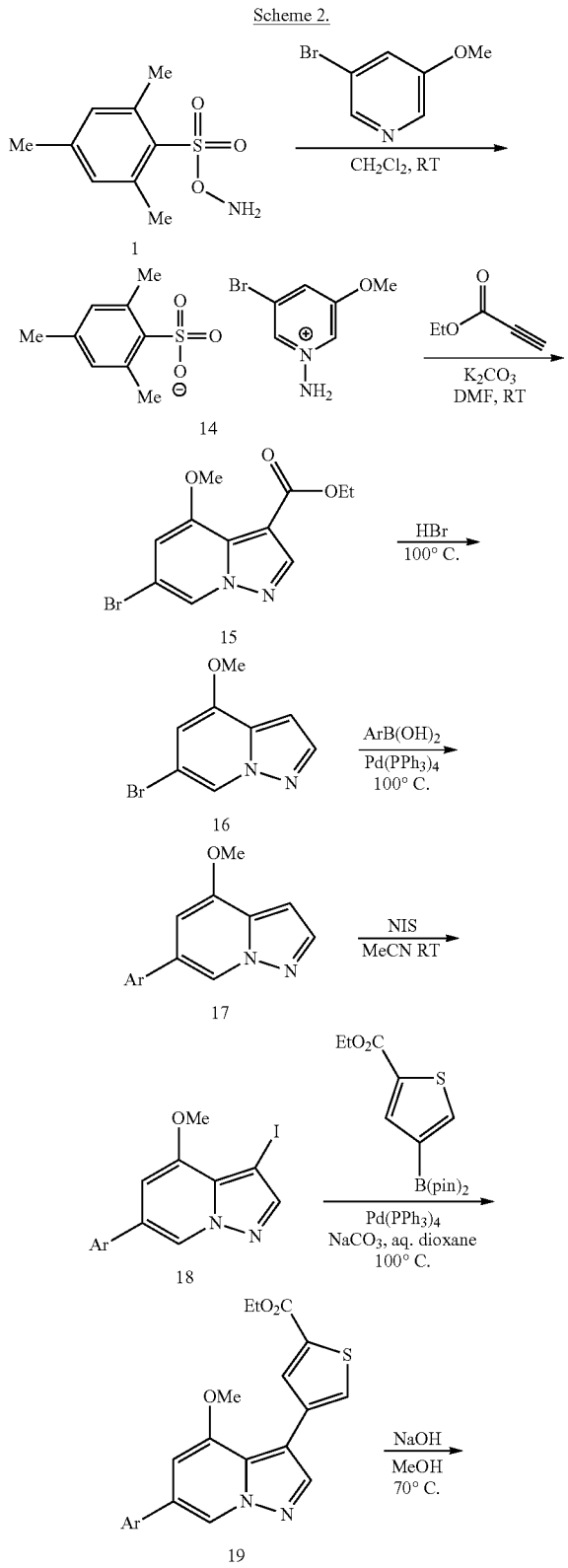

Preparation of the pyrazolopyridine core of the type 4 began with the preparation of O-mesitylenesulfonylhydroxylamine (1) in two steps from commercial starting materials. This reagent exposed to commercially available pyridines to access appropriately functionalized N-imino-pyridinium mesitylenesulphonate derivates of the type 2. A [3+2] cyclization of 2 with ethyl propiolate yields the pyrazolopyridine core (3). Functionalization of the 6-position of the pyrazolopyridine core is accomplished via a Suzuki coupling reaction to install aryl or heteroaromatic functionality (4) using commercially available boronic acids or esters. To install the thaizole moiety, the ester 4 is first saponified to acid 5 and then converted to the acid chloride 6. Subsequent ketone synthesis is carried out in the presence of aluminum chloride and dialkylzinc to provide 7. α-Bromination provides bromoketone 8, which is then subject to condensation with ethylthiooxamate to yield the thiazole 9. Chlorination of the thiazole

27

-continued

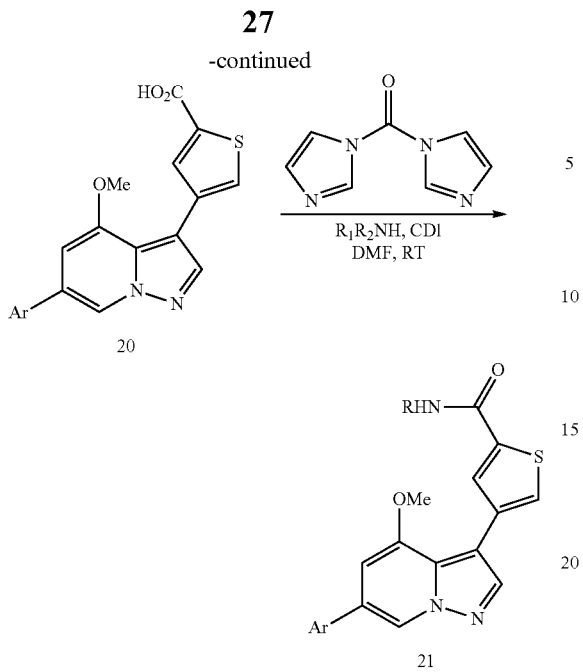

Molecules of type 21 were prepared according to scheme 2. O-Mesitylenesulfonylhydroxylamine (1) was used to access N-imino-pyridinium mesitylenesulphonate 14. [3+2] Cyclization of 2 with ethyl propiolate yields pyrazolopyridine 15. Decarboxylation in neat hydrobromic acid afforded 16. Functionalization of the 6-position of the pyrazolopyridine core is accomplished via a Suzuki coupling reaction to install aryl or heteroaromatic functionality (17) using known or commercially available boronic acids or esters. For specific boronic ester examples, see WO 2004052286 A2 and WO 2007085873 A1 Halogenation via reaction with N-iodosuccinimide enables a second Suzuki coupling of iodide 18 with thiophene boronic ester to yield coupling product 19. Hydrolysis of the ester yielded acid 20 and subsequent coupling with an amine yielded target 21.

Scheme 3.

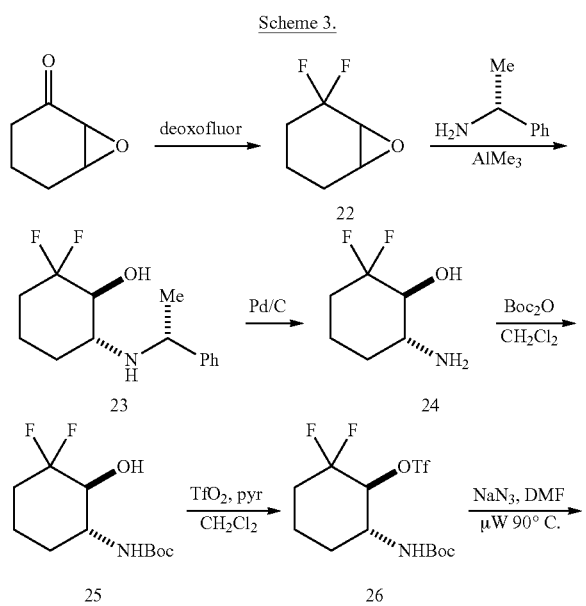

28

-continued

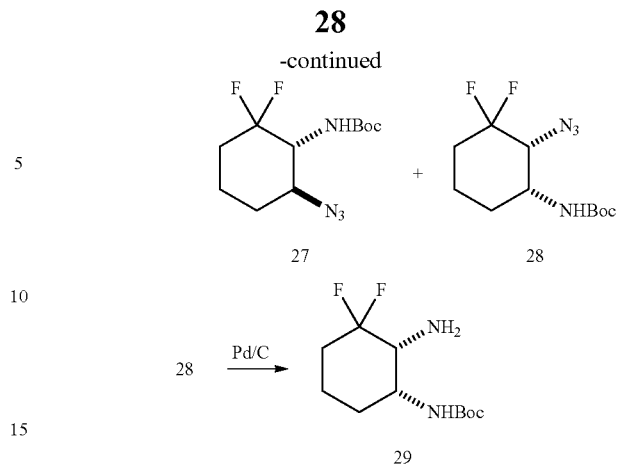

Amines were prepared according to scheme 3. Commercially available 7-oxabicyclo[4.1.0]heptan-2-one was reacted with deoxofluor to obtain 3,3-difluorinated product 22. Epoxide activation with trimethylaluminum and reaction with a known chiral amine provided amino alcohol 23. The free amine 24 was revealed via hydrogenation and then reprotected as the tert-butyl carbamate 25. The alcohol was activated towards displacement by conversion to triflate 26. Nucleophilic displacement by sodium azide provided 28 which was subsequently reduced to yield amine 29.

Scheme 4.

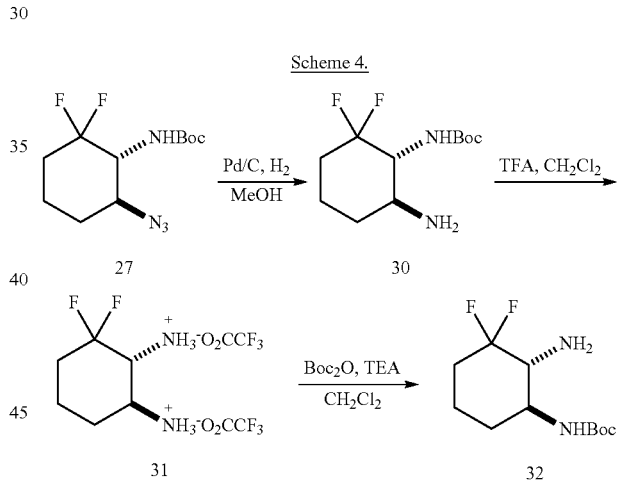

Amines were prepared according to scheme 4. Intermediate 27 was reduced to the corresponding diamine 30. Deprotection of 30 under acidic conditions produced the bis-TFA salt of 31. Selective monoprotection of 31 yielded Boc-protected diamine 32.

Scheme 5.

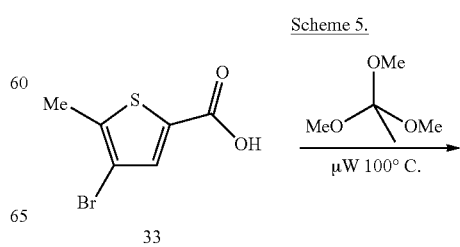

29

-continued

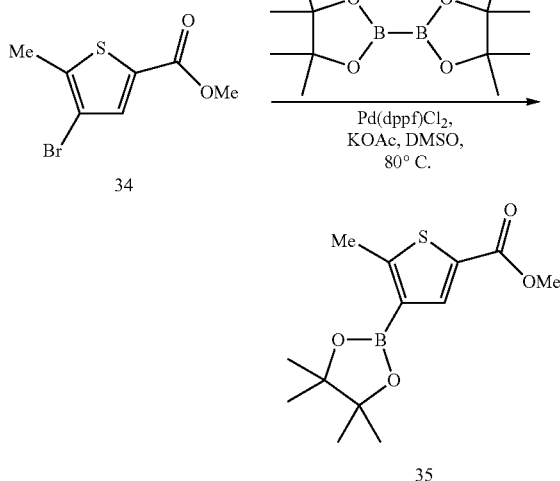

Commercially available 4-bromo-5-methyl-2-thiophen-ecarboxylic acid 33 (1.03 g, 4.66 mmol) and trimethyl orthoacetate (1.53 ml, 13.98 mmol) were heated at 40 min at 100° C. in a microwave reactor to yield ethyl ester 34. Boronic ester 35 was generated via a palladium-mediated coupling with bispinacolatodiboron.

Scheme 6.

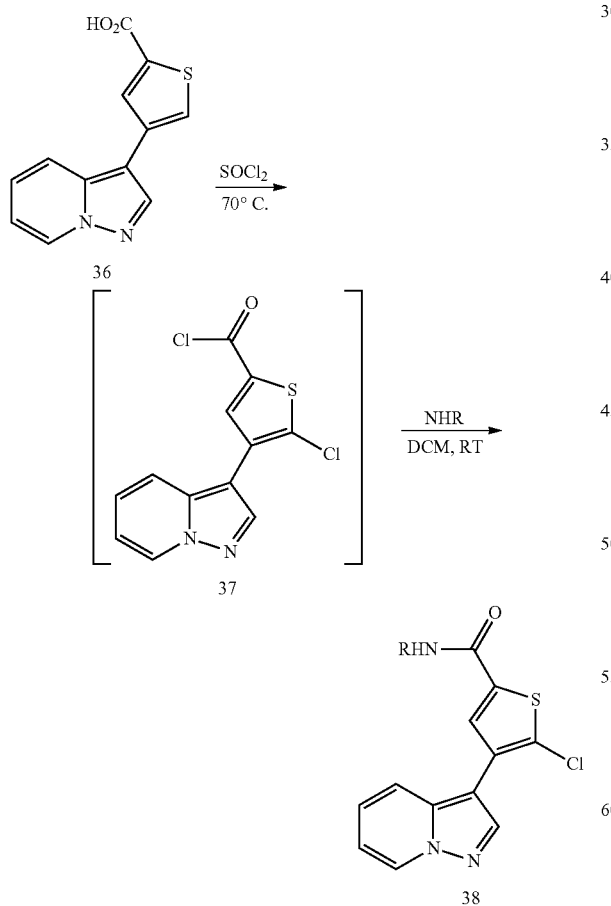

Molecules of type 36 were prepared according to scheme 5 using material generated from the synthetic sequence in scheme 2 (analogous to intermediate 20). Refluxing the

30

2-thiophene carboxylic acid (36) in thionyl chloride generates in situ acid chloride 37. Amide formation occurs upon exposure of the acid chloride 37 with an amine to yield product 38.

Scheme 7.

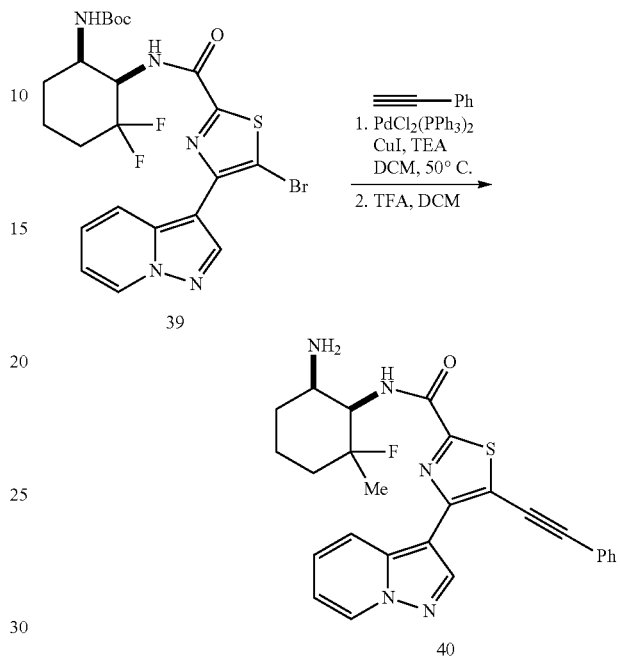

Molecules of type 40 were prepared according to scheme 7 using material generated from the synthetic sequence in scheme 1 (analogous to intermediate 13). Sonogashira coupling of the bromothiazole 39 with phenyl acetylene yielded the desired adduct. Subsequent deprotection yielded compound 40.

Scheme 8.

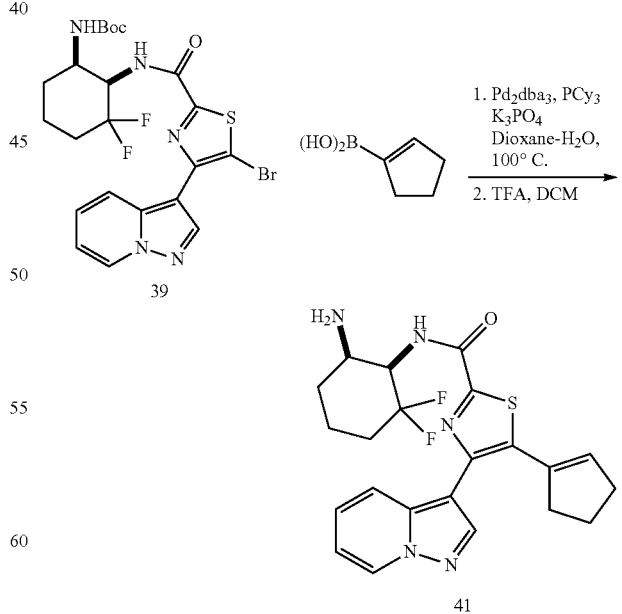

Molecules of type 41 were prepared according to scheme 8 using material generated from the synthetic sequence in scheme 1 (analogous to intermediate 13). A palladium-mediated Suzuki coupling of the bromothiazole 39 with cyclopentenyl boronic acid yielded the desired adduct. Subsequent deprotection yielded compound 41.

Scheme 9.

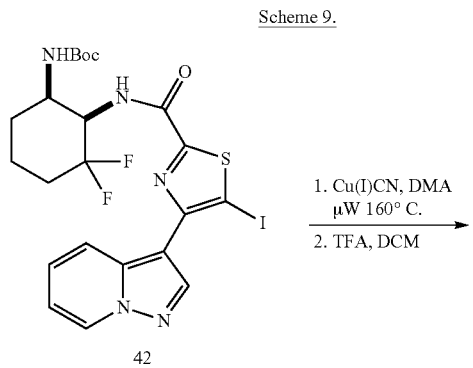

Molecules of type 43 were prepared according to scheme 9 using material generated from the synthetic sequence in scheme 1 (analogous to intermediate 13). Cyanation of iodothiazole 42 proceeded via copper-mediated coupling to yield the desired adduct. Subsequent deprotection yielded compound 43.

Scheme 10.

Step A:

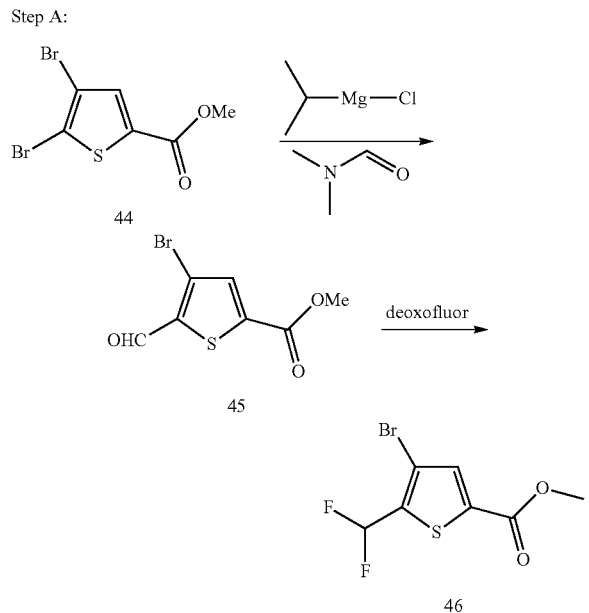

Step B:

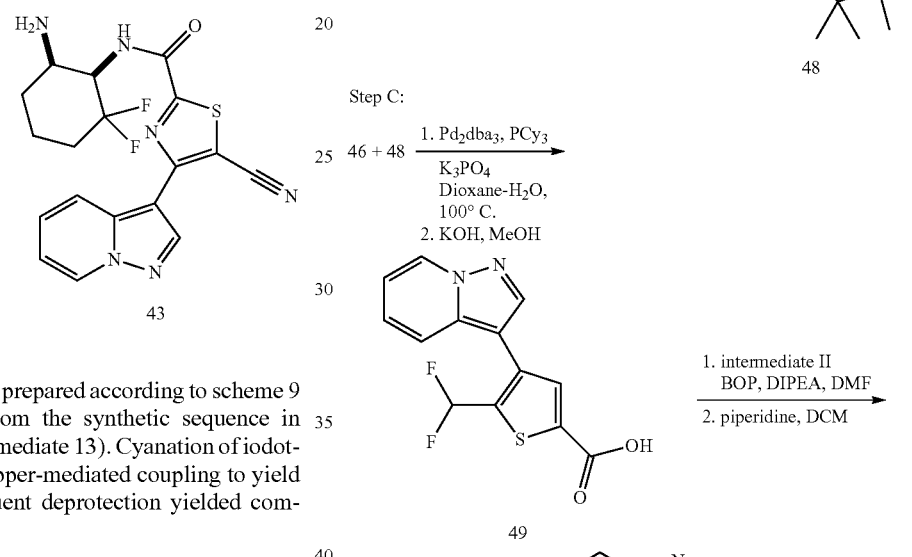

Molecules of type 50 were prepared according to scheme 10 with the synthesis of compounds 46 and 48. Compound 46 (step A) was synthesized from commercially available dibromide 44. Regioselective metal-exchange followed by DMF quench provided aldehyde 46. Aldehyde 46 was reacted with excess deoxofluor to furnish compound 46. Preparation of boronic ester 48 (step B) was accomplished from commercial starting material (compound 47) via lithium-halogen exchange in the presence of 4,4,5,5-tetramethyl-2-(propan-2-yloxy)-1,3,2-dioxaborolane. Palladium-mediated coupling of 46 and 48 was followed by saponification to yield carboxylic acid 49. Amide formation with intermediate II and subsequent deprotection provided compound 50.

Scheme 11.

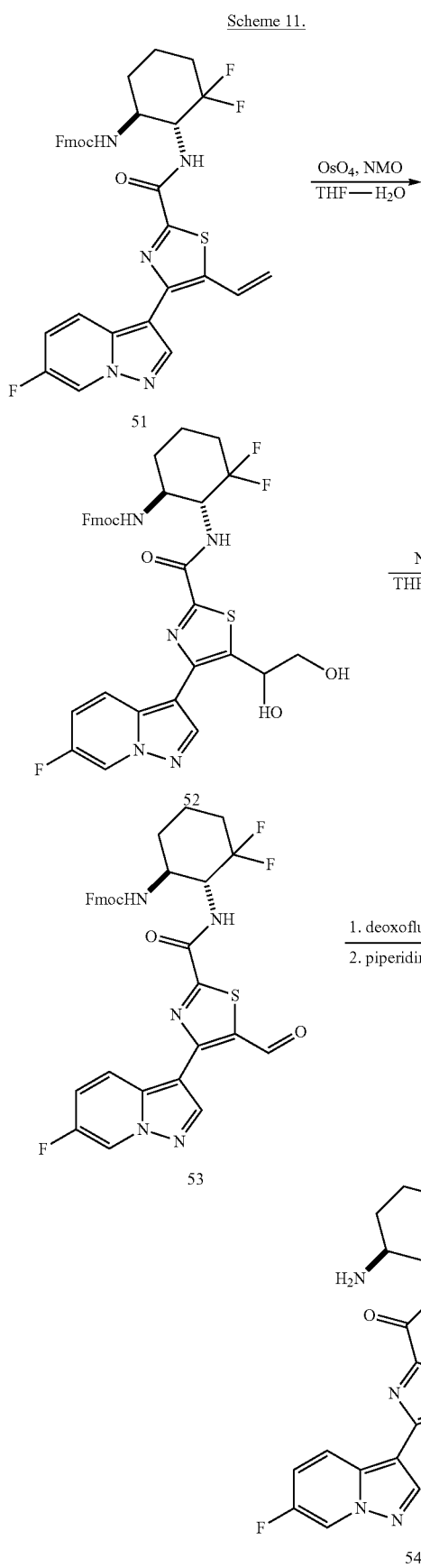

Molecules of type 54 were prepared according to scheme 11 using material generated from the synthetic sequence in example 218 (that yields compound 51). Specifically, varied functionality on the core pyridine ring (see scheme 1 and example 1, step A) is introduced via the use of an appropriately functionalized pyridine in step A, part 2, which in this case was 3-fluoropyridine. The synthesis continued with the use of step C (such that step B was not carried out) with all subsequent steps with the exception of the final deprotection step.

Dihydroxylation of compound 51 with catalytic osmium tetraoxide was carried out to provide diol 52. Periodate cleavage of this diol furnishes the corresponding aldehyde 53. Reaction with deoxofluor and subsequent Fmoc-deprotection yields product 54.

Scheme 12.

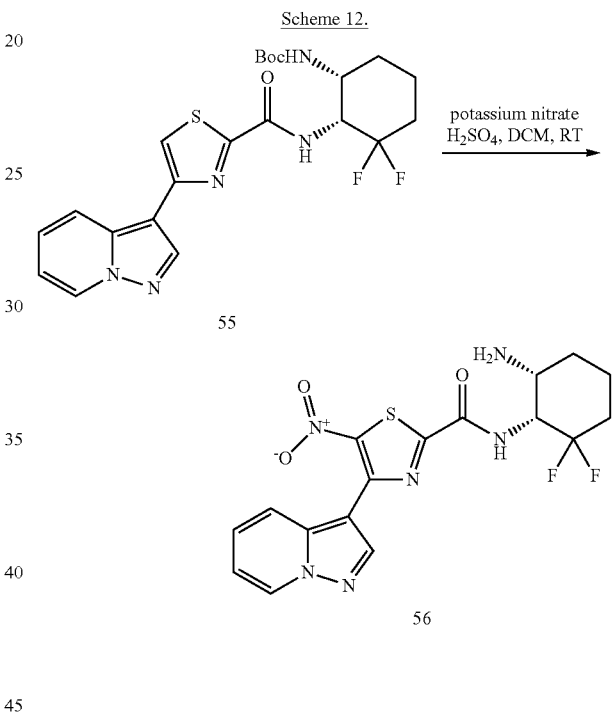

Synthesis of compound 56 began with Boc-protected N-[(1R,6R)-6-amino-2,2-difluorocyclohexyl]-4-(pyrazolo[1,5-a]pyridin-3-yl)-1,3-thiazole-2-carboxamide (55, synthesized using the procedure outlined in example 2). Direct nitration of the thiazole provided the desired adduct, compound 56.

Scheme 13.

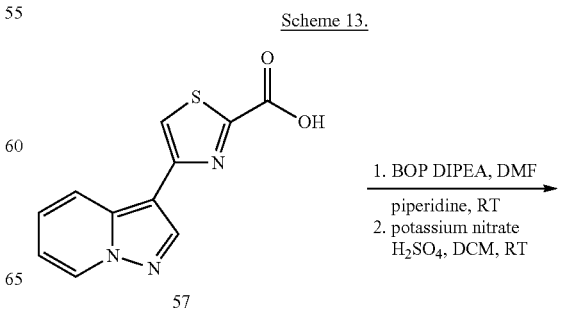

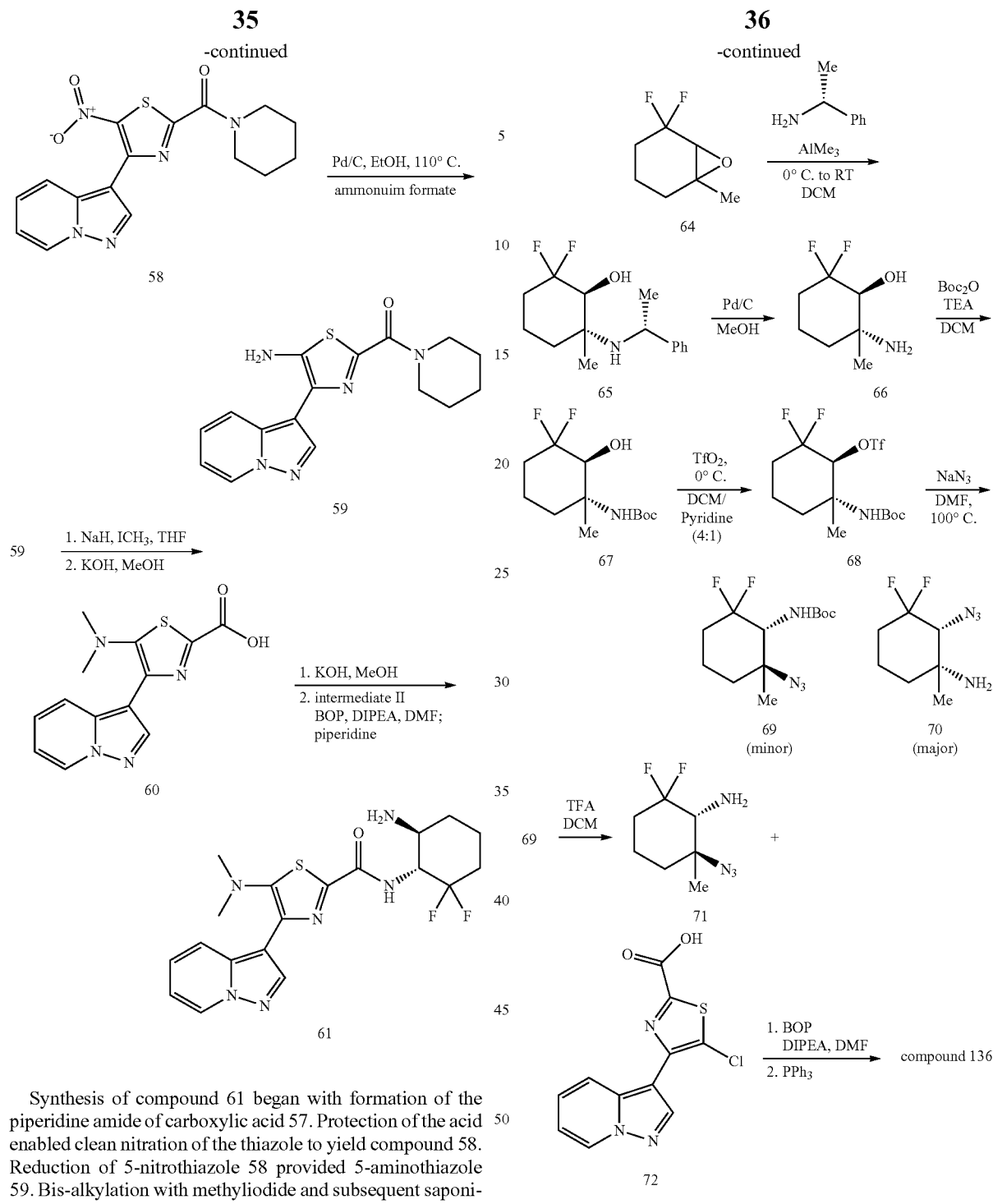

Synthesis of compound 61 began with formation of the piperidine amide of carboxylic acid 57. Protection of the acid enabled clean nitration of the thiazole to yield compound 58. Reduction of 5-nitrothiazole 58 provided 5-aminothiazole 59. Bis-alkylation with methyliodide and subsequent saponification yielded carboxylic acid 60. Amide formation with intermediate II and deprotection yields compound 61, Scheme 14.

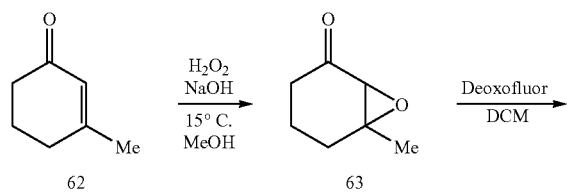

Compound 136 was synthesized according to scheme 14 and begins with a Weitz-Scheffer epoxidation of commercially available 3-methylcyclohex-2-en-1-one (62) to yield compound 63. Treatment with deoxofluor provides the 3,3-difluorinated product 64. Epoxide activation with trimethylaluminum and reaction with a known chiral amine provided amino alcohol 65. The free amine 66 was revealed via hydrogenation and then reprotected as the tert-butyl carbamate 67. The alcohol was activated towards displacement by conversion to triflate 68. Nucleophilic displacement by sodium azide provided 69 and 70 which were separable by chromatography. Azide 69 was coupled to carboxylic acid 72 (see procedure in example 2 for synthesis of acid core) and was subsequently reduced to yield example compound 136.

Scheme 15.

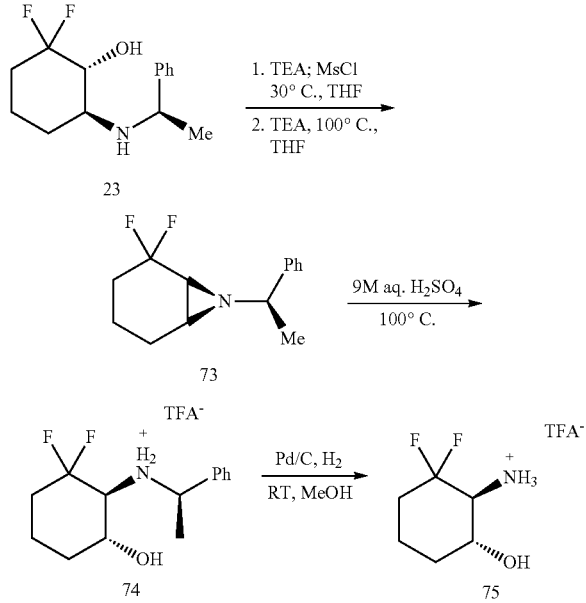

Intermediate III (compound 75) was synthesized from (1R,6S)-2,2-difluoro-6-{[(1R)-1-phenylethyl]amino}cyclohexanol (compound 23, scheme 3). Treatment with triethylamine affords aziridine 73, which was hydrolyzed to produce alcohol 74. Hydrogenation revealed the desired aminoalcohol 75.

Scheme 16.

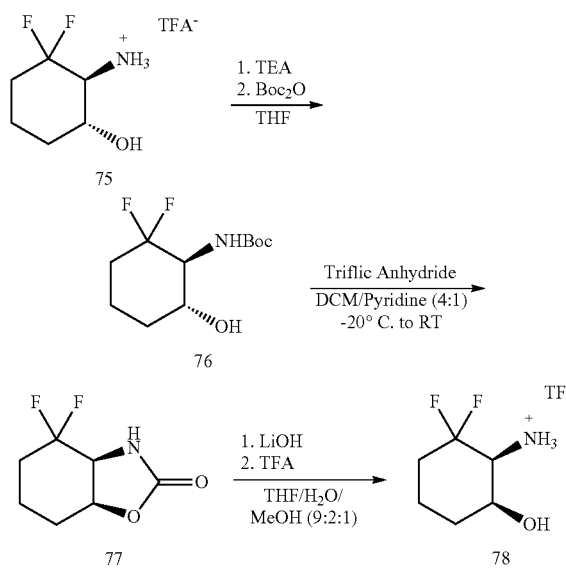

Intermediate IV (compound 78) was synthesized according to scheme 16, using intermediate III. Aminoalcohol 75 was protected as the tert-butyl carbamate 76. Activation of the alcohol towards displacement by conversion to triflate, resulted in the formation of oxazolidinone 77. Saponification and deprotection yielded compound 78.

Intermediate I

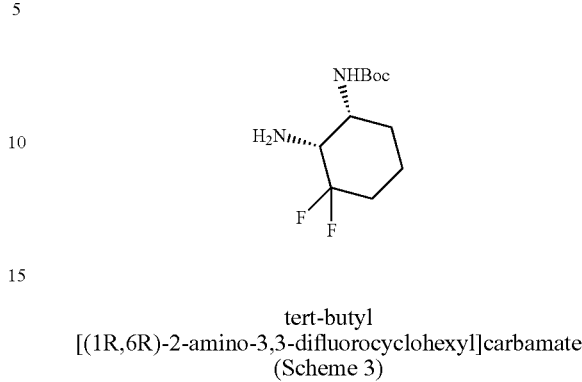

tert-butyl
[(1R,6R)-2-amino-3,3-difluorocyclohexyl]carbamate
(Scheme 3)

Step A: Difluorination

To a solution of 7-oxabicyclo[4.1.0]heptan-2-one (55.8 g, 0.5 mol) in dichloromethane (200 mL) cooled to 0° C. was added 1,1,1-trifluoro-N,N-bis(2-methoxyethyl)silanamine (Deoxofluor, 202 mL, 1.1 mol) and the resulting reaction was warmed to ambient temperature and stirred for 16 hours. The reaction was cooled to −20° C. and carefully quenched with water (10 mL, slow addition). The reaction was then partitioned between water/dichloromethane and the organics were passed through a plug of silica gel. This crude organic solution of 22 was carried into the next reaction.

Step B: Epoxide Opening

A solution of (1R)-1-phenylethanamine (22, 72 mL, 0.57 mol) in dichloromethane (200 mL) was cooled to 0° C. and treated with trimethylaluminum (260 mL, 0.52 mol) and the resulting solution was stirred for 1 hour at 0° C. To this solution was added a solution of 2,2-difluoro-7-oxabicyclo[4.1.0]heptane (66 g, 0.49 mol) in dichloromethane (200 mL) and the resulting mixture stirred at 0° C. for 3 hours. The reaction was then warmed to ambient temperature for 16 hours. The reaction was cooled to 0° C., treated with 103 g of sodium flouride and then quenched with water (90 mL, slow addition). The reaction was warmed to ambient temperature, the solids filtered and the solution evaporated in vacuo, Purification by flash chromatography (50-100% ethyl acetate in hexanes) gave 36.3 g (29%) of (1S,6R)-2,2-difluoro-6-{[(1R)-1-phenylethyl]amino}cyclohexanol 23 (plus 32 g of 1R,6S diastereomer) as a white solid: $^1$H NMR (500 MHz, CDCl$_3$) δ 7.32 (5H, s), 3.90 (1H, q, =6.6 Hz), 3.39 (1H, ddd, J=19.8, 9.8, 4.2 Hz), 2.70 (1H, m), 2.11 (1H, m), 1.80 (1H, m), 1.62 (2H, m), 1.43 (1H, m), 1.36 (3H, d, J=6.6 Hz), 0.96 (1H, m).

Step C: Hydrogenation

A solution of (1S,6R)-2,2-difluoro-6-{[(1R)-1-phenylethyl]amino}cyclohexanol 23 (2 g, 7.83 mmol) in methanol (100 mL) was degassed with nitrogen, treated with Pd (OH)$_2$/C (0.55 g) and then placed under an atmosphere of hydrogen and stirred vigorously for 16 hours. The reaction was filtered, washing with methanol, and evaporated in vacuo to give 1.0 g (84%) of (1S,6R)-6-amino-2,2-difluorocyclohexanol 24 as a white solid: $^1$H NMR (500 MHz, CD$_3$OD) δ 3.34 (1H, m), 2.74 (1H, m), 2.07 (1H, m), 1.89 (1H, m), 1.73 (2H, m), 1.50 (1H, m), 1.27 (1H, m).

Step D: Amine Protection

A solution of (1S,6R)-6-amino-2,2-difluorocyclohexanol 24 (2 g, 7.54 mmol) in dichloromethane (60 mL) was treated with triethylamine (5.26 mL, 37.7 mmol) and Boc anhydride (1.81 g, 830 mmol) and the resulting solution was stirred at ambient temperature for 16 hours. The reaction was evaporated in vacuo and purified by flash column chromatography (10-30% ethyl acetate in hexanes) to give 0.6 g (32%) of tort-butyl [(1R,2S)-3,3-difluoro-2-hydroxycyclohexyl]carbamate 25 as a white solid: $^1$H NMR (500 MHz, CDCl$_3$) δ 4.67 (1H, bs), 3.67 (1H, bm), 3.50 (1H, bm), 3.21 (1H, bs), 2.15 (1H, m), 2.03 (1H, m), 1.62 (3H, m), 1.45 (9H, s), 1.34 (1H, m).

Step E: Triflate Formation

A solution of tert-butyl [(1R,6S)-3,3-difluoro-2-hydroxycyclohexyl]carbamate 25 (1.78 g, 7.08 mmol) in dichloromethane (50 mL) was treated with pyridine (12.5 mL) and cooled to 0° C. Triflic anhydride (4.43 mL, 26.2 mmol) was added dropwise and the reaction was stirred at 0° C. for 2 hours and quenched with water. The reaction was partitioned between water and diethyl ether, the organics were dried over sodium sulfate, filtered and evaporated in vacuo. Purification by flash chromatography (0-15% ethyl acetate in hexanes) gave 2.33 (86%) of (1S,6R)-6-[(tert-butoxycarbonyl)amino]-2,2-difluorocyclohexyl trifluoromethanesulfonate 26 as a white solid: $^1$H NMR (500 MHz, CDCl$_3$) δ 4.77 (bm, 1H), 4.69 (bd, 1H), 3.92 (bm, 1H), 2.28 (m, 1H), 2.08 (m, 1H), 1.79 (m, 2H), 1.64 (m, 2H), 1.45 (s, 9H).

Step F: Azide Displacement

A solution of (1S,6R)-6-[(tert-butoxycarbonyl)amino]-2,2-difluorocyclohexyl trifluoromethanesulfonate 26 (2.32 g, 6.05 mmol) and sodium azide (2.36 g, 36.3 mmol) in DMF was sealed and heated to 100° C. for 3 hours in a microwave reactor. The reaction was partitioned between water and ethyl acetate. The organics were washed with water, dried over magnesium sulfate, filtered and evaporated in vacuo. Purification by flash chromatography (0-15% ethyl acetate in hexanes) gave 0.94 g (56%) of tert-butyl [(1R,2R)-2-azido-3,3-difluorocyclohexyl]carbamate 28 as a white solid: $^1$H NMR (500 MHz, CDCl$_3$) δ 4.75 (1H, m), 3.98 (1H, bs), 3.88 (1H, bm), 1.96 (2H, m), 1.70 (2H, m), 1.46 (9H, s), 1.37 (2H, m).

The diastereomer 27 was also obtained from this procedure: $^1$H NMR (500 MHz, CDCl$_3$) δ 4.82-4.80 (1H, br d, J=9.4 Hz), 3.93-3.89 (1H, dt, J=11.1, 10.5, 12.6, 8.1 Hz), 3.31-3.27 (1H, m), 2.24-2.19 (1H, m), 2.13-2.10 (1H, m), 1.86-1.67 (2H, m), 1.55-1.52 (2H, m), 1.48-1.41 (11H, m); $^{19}$F NMR (CDCl$_3$, 564 MHz) δ −102.2-−102.7 (1F, d, J=244 Hz), −113.9-−114.5 (1F, m).

Step G: Azide Reduction

A solution of tert-butyl [(1R,6R)-2-azido-3,3-difluorocyclohexyl]carbamate 28 (0.94 g, 3.40 mmol) in methanol (20 mL) was degassed with nitrogen and treated with 10% Pd/C (72 mg). The resulting heterogenous solution was exposed to a hydrogen atmosphere and stirred vigorously for 16 hours. The reaction was filtered, washing with methanol, and evaporated in vacuo to give 0.78 g (91%) of tert-butyl [(1R,2R)-2-amino-3,3-difluorocyclohexyl]carbamate 29 as a white solid: $^1$H NMR (500 MHz, DMSO-d$_6$) δ 6.67 (1H, d, J=8.3 Hz), 3.55 (1H, bs), 3.07 (1H, bs), 2.03 (1H, m), 1.62 (3H, m), 1.45 (1H, m), 1.36 (12H, m).

Intermediate II

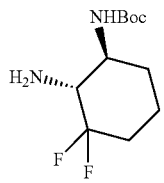

tert-butyl [(1R,6S)-2-amino-3,3-difluorocyclohexyl]carbamate (Scheme 4)

Step A: Reduction of Azide

To a clean dry 1 L RBF charged with tert-butyl [(1R,2S)-2-azido-3,3-difluorocyclohexyl]carbamate 27 (18.84 g, 68.2 mmol) was added 400 mL methanol. The system was degassed and purged (3× with N$_2$) before the addition of Pd/C (1.45 g). The reaction was stirred for 2 d under 1 atm of hydrogen. Upon reaction completion, the reaction was filtered through a plug of celite and concentrated to dryness to yield tert-butyl [(1R,2S)-2-amino-3,3-difluorocyclohexyl]carbamate 30 (16.47 g, 97% yield) as a pure white solid. $^1$H NMR (CDCl$_3$, 500 MHz) δ 4.76-4.74 (1H, d, J=10 Hz), 3.61-3.56 (1H, m), 2.63-2.59 (1H, dd 0.1-9.5 Hz), 2.2-2.0 (2H, m), 1.8-1.68, (2H, m), 1.53-1.42 (11H, m), 1.29-1.21 (m, 2H); $^{19}$F NMR (CDCl$_3$, 564 MHz) δ −101.7-−102.1 (1F, J=241 Hz), −114.3-−114.9 (1F, m)

Step B: BOC-Deprotection

To a clean dry 100 mL RBF was added 30 (5 g, 19.98 mmol), dichloromethane (50 mL) and TFA (6.16 mL, 80 mmol). The reaction was stirred overnight. Upon reaction completion, the solvent was removed under reduced pressure and 7.5 g (99%) pure bis-TFA salt 31 was isolated as a brown oil. $^{19}$F NMR (CDC$_{13}$, 564 MHz) δ −81.07 (6F, s), −99.7-−100.1 (1F, d, J=241.6 Hz), −111.1-−111.5 (1F, br d, J=242.1 Hz).

Step C: Monoprotection of Diamine

To a clean dry 250 mL RBF charged with 31 (7.5 g, 19.8 mmol) was added dichloromethane (100 mL), triethylamine (11.1 mL, 79.0 mmol) followed by BOCA) (5.52 mL, 23.8 mmol). The reaction was stirred for 10 hr at ambient temperature. Upon completion, the solvent was removed under reduced pressure and the resultant residue was purified by column chromatography (silica gel, 10-50% ethyl acetate in hexanes with 1% NH$_4$OH, linear gradient) to yield tert-butyl [(1R,2S)-2-amino-3,3-difluorocyclohexyl]carbamate 32 (1.8 g, 38% yield) of pure material isolated, along with 2.2 g mixed Boc-products. $^1$H NMR (CDCl$_3$, 500 MHz) δ 4.76 (1H, br s), 3.39 (br m, 1H), 2.71-2.64 (1H, m), 2.2-2.1 (2H, m), 1.7-1.59 (2H, m), 1.56-1.51 (2H, m), 1.45 (9H, s), 1.29-1.21 (2H, m); $^{19}$F NMR (CDCl$_3$, 564 MHz) δ −100.4-−100.9 (1F, d, J=236 Hz), −114.35-−114.87 (1F, br d, J=232 Hz).

Alternatively, Fmoc-protection could also be carried out to provide 9H-fluoren-9-ylmethyl [(1S,2R)-2-amino-3,3-difluorocyclohexyl]carbamate.

Intermediate III

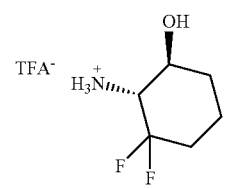

(1R,6S)-2,2-difluoro-6-hydroxycyclohexanaminium trifluoroacetate (Scheme 15)

To a solution of (23) (1.02 g, 4.01 mmol) in THF (20 mL) was added triethyl amine (0.56 mL, 4.01 mmol), followed by methanesulfonyl chloride (0.34 mL, 4.41 mmol). The reaction was allowed to stir at 35° C. overnight. After cooling to room temperature, the reaction mixture was filtered and then concentrated under reduced pressure. The crude material was purified by column chromatography (silica gel, 20-60% ethyl acetate in hexanes) to yield (1S,6R)-2,2-difluoro-6-{[(1R)-1-phenylethyl]amino}cyclohexyl methanesulfonate (1.01 g, 3.03 mmol, 76% yield). In a microwave vial, the sulfonate intermediate (1.02 g, 3.07 mmol) was dissolved in THF (15.4 mL) and triethylamine (0.58 mL, 4.15 mmol). The vial was sealed and was heated to 100° C. and was stirred overnight. After cooling to room temperature, the reaction mixture was concentrated under pressure. The resultant residue was directly purified by column chromatography (silica gel, 0-70% ether in hexanes, linear gradient) to yield aziridine 73.

Aziridine hydrolysis was accomplished via reflux of compound 73 (660 mg, 2.78 mmol) in 9M sulfuric acid (10 mL, 90 mmol) for 2 hours. After cooling to room temperature, the reaction mixture was neutralized with 1N NaOH and was diluted with water. The reaction was partitioned with dichloromethane and the organic layer cut and dried under reduced pressure. Compound 74 was purified by reverse phase chromatography (10-90% MeCN in water with 0.05% TFA modifier, linear gradient) and was isolated as a TFA salt.

(1R,6S)-2,2-difluoro-6-hydroxy-N-[(1R)-1-phenylethyl]cyclohexanaminium trifluoroacetate (74) in a solution of methanol (1.5 mL) was exposed to Pd/C (409 mg, 0.384 mmol) and hydrogen atmosphere (1 atm). The heterogeneous reaction mixture was filtered through a plug of celite and washed three times with 30 mL of methanol. The filtrate was concentrated under reduced pressure to yield (1R,6S)-2,2-difluoro-6-hydroxycyclohexanaminium trifluoroacetate (75) in quantitative yield. $^1$H NMR (500 MHz, CD$_3$OD) δ 3.68 (s, 1H), 3.34 (t, J=16.6, 2H), 2.19 (s, 1H), 2.06 (s, 1H), 1.87 (d, J=56.3, 2H), 1.49 (s, 2H), $^{19}$F NMR (470 MHz, cd3od) δ −77.30 (s, 3F), −99.95 (d, J=242.9, 1F), −114.48--116.71 (m, 1F).

Intermediate IV

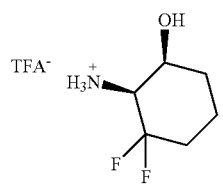

(1S,6S)-2,2-difluoro-6-hydroxycyclohexanaminium trifluoroacetate (Scheme 16)

Compound 75 (225 mg, 0.848 mmol) was dissolved in THF (4.24 mL) and triethylamine (237 µL, 1.697 mmol) was added. After 5 minutes Boc$_2$O (197 µL, 0.85 mmol) was added and the reaction mixture was stirred at RT overnight. The solvent was removed under reduced pressure and the remaining residue was purified by column chromatography (silica gel, 100% hexanes then 20-60% ethyl acetate in hexanes) to yield compound 76 (183 mg, 0.728 mmol, 86% yield).

A solution of compound 76 (183 mg, 0.73 mmol) in dichloromethane (2.9 mL) and pyridine (728 µL) was cooled to −20° C. Triflic anhydride (123 µL, 0.73 mmol) added slowly and reaction was stirred at −20° C. Upon completion, the reaction mixture was warmed to room temperature and was diluted with water. The product was extracted with dichloromethane (3×5 mL) and the combined organics were dried over sodium sulfate and concentrated. The resultant residue was purified by column chromatography (silica gel, 100% hexanes then 50% ethyl acetate in hexanes) to obtain compound 77 (109 mg, 84% yield).

A heterogeneous mixture of compound 77 (80 mg, 0.45 mmol) and lithium hydroxide (97 mg, 2.26 mmol) in THF (1.7 mL), methanol (1744), and water (347 µL) was warmed to 50° C. After cooling to RT, the reaction mixture was filtered though celite and TFA (500 µL, 6.49 mmol) was added to filtrate. The filtrate was dried under reduced pressure to yield (1S,6S)-2,2-difluoro-6-hydroxycyclohexanaminium trifluoroacetate (78, 120 mg, quant. yield). $^1$H NMR (500 MHz, CD$_3$OD) δ 4.21 (s, 1H), 3.63 (d, J=19.7, 1H), 3.31 (s, 1H), 2.17 (d, J=11.2, 1H), 1.89 (d, J=32.2, 7H), 1.73-1.53 (m, 2H).

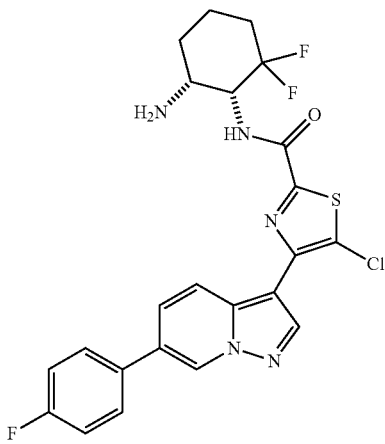 [SMILES: N[C@@H]1CCCC(F)(F)[C@@H]1NC(=O)c1nc(-c2cnn3cc(-c4ccc(F)cc4)ccc23)c(Cl)s1]

Example 1

N-[(1R,6R)-6-amino-2,2-difluorocyclohexyl]-5-chloro-4-[6-fluorophenyl)pyrazolo[1,5-a]pyridin-3-yl]-1,3-thiazole-2-carboxamide (Scheme 1)

Step A: [3+2] Cycloaddition
Part 1: Preparation of O-Mesitylenesulfonylhydroxylamine (2) (Literature reference-Tetrahedron Lett. 1972, 40, 4133-4135)

To a suspension of ethyl N-hydroxyacetimidate (4.72 g, 45.7 mmol) in DMF (453 ml) was added triethylamine (9.53 ml, 68.6 mmol) followed by portionwise addition of mesitylenesulfonyl chloride (1, 10 g, 45.7 mmol). The reaction mixture was stirred for 2 hours at room temperature then poured into ice water (150 mL). The resulting precipitate was collected by vacuum filtration. The collected solids were treated with neat perchloric acid (32.8 ml, 229 mmol) and stirred until homogeneous. Distilled water (30 mL) was used to titurate white crystals of O-mesitylenesulfonylhydroxylamine (2, 8.31 g, 38.6 mmol, 84% yield). MS APCI: [M+H]$^+$ m/z 216.3.

Part 2: Preparation of N-Iminopyridinium Salt
3-Bromopyridine (1.727 ml, 17.93 mmol) was added dropwise to a heterogeneous suspension of O-mesitylenesulfonylhydroxylamine (2, 3.86 g, 17.93 mmol) in DCM (25 ml). The reaction was stirred at room temperature for 30 minutes before ether (30 mL) was added to titurate the desired product from solution at 0° C. 3-Bromo-N-imino-pyridinium mesitylenesulphonate (3, 35.62 g, 15.06 mmol, 84% yield) was isolated as a white fluffy solid. MS APCI: [M+H]$^+$ m/z 175.0.

Part 3: Cycloaddition
Anhydrous potassium carbonate (4.02 g, 29.1 mmol) was added to a solution of N-imino-pyridinium mesitylenesulphonate (3, 7.24 g, 19.40 mmol) in acetone (70 mL). After stirring for 30 minutes at room temperature, ethyl propiolate (3.93 ml, 38.8 mmol) was added dropwise to the reaction.

After 6 hours, the solids were filtered off and the mother liquors were concentrated. The resulting residue was taken up in ethyl acetate (50 mL) and washed with brine (2×50 mL). The combined organics were dried over $Na_2SO_4$ and concentrated. Purification by column chromatography (10-40% acetone in hexane, linear gradient) yielded cyclized product 4 (2.56 g, 9.51 mmol, 49.0% yield) as an orange solid. MS APCI: $[M+H]^+$ m/z 270.1

Step B: Suzuki Coupling

A solution of ethyl 6-bromopyrazolo[1,5-a]pyridine-3-carboxylate (4, 890 mg, 3.31 mmol) and p-fluorophenylboronic acid (555 mg, 3.97 mmol) in dioxane (13.23 mL) and aq. sodium carbonate (2M, 4.5 mL, 9.00 mmol) deoxygenated. $Pd(PPh_3)_4$ (382 mg, 0.3 mmol) was added to the reaction and system was heated by to 100° C. and stirred for 1.5 hours. After cooling the reaction to room temperature, the reaction was filtered through a pad of silica and partitioned with DCM (10 mL) and washed with water (2×15 mL). The organic was dried and concentrated, then dissolved in EtOAc (10 mL). The resulting gold precipitate was filtered off to yield 535 mg of the coupled product 5. The mother liquor was concentrated and additional product (185 mg) was recovered by column chromatography (10% acetone in hexanes) for a combined yield of 77% (720 mg, 2.53 mmol). MS APCI: $[M+H]^+$ m/z 285.3.

Step C: Ketone Synthesis

Part 1: Ester Saponification

The hydrolysis of ethyl 6-(4-fluorophenyl)pyrazolo[1,5-a]pyridine-3-carboxylate (5, 720 mg, 2.53 mmol) was carried out in methanol (5.0 mL) with aq. sodium hydroxide (4N, 1.9 mL, 7.60 mmol) at 50° C. Methanol was removed under reduced pressure and 1M HCl was used to acidify the solution. 6-(4-Fluorophenyl)pyrazolo[1,5-a]pyridine-3-carboxylate (6) was collected by filtration (600 mg, 2.342 mmol, 92% yield). MS APCI: $[M+H]^+$ m/z 257.2.

Part 2: Acid Chloride Formation

Thionyl chloride (4.1 mL, 56.2 mmol) was added to 6-(4-fluorophenyl)pyrazolo[1,5-a]pyridine-3-carboxylate (6, 720 mg, 2.81 mmol) before heating the system to 65° C. Excess thionyl chloride was removed under reduced pressure to yield 6-(4-fluorophenyl)pyrazolo[1,5-a]pyridine-3-carboxyl chloride (7) in quantitative yield (773 mg, 2.18 mmol). Crude material was analyzed after methanol quench to obtain the corresponding methyl ester product, MS APCI: $[M+H]^+$ m/z 271.1.

Part 3: Alkylation (Literature Precedent: Arisawa, M.; Torisawa, Y.; Kawahara, M.; Yamanaka, M.; Nishida, A.; Nakagawa, M. *J. Org. Chem.* 1997, 62, 4327.)

To a cooled suspension of 6-(4-fluorophenyl)pyrazolo[1,5-a]pyridine-3-carboxyl chloride (7, 300 mg, 1.092 mmol) at −70° C. in DCM (2.2 mL) was added aluminum chloride (146 mg, 1.092 mmol). The reaction was aged for 1 hour at −30° C. A solution of dimethylzinc (655 μl, 0.655 mmol, 1M in heptanes) was added over 30 minutes at −70° C. and then allowed to warm to room temperature. Water (10 mL) was added to the reaction and the solution was partitioned with DCM (20 mL). The collected organic was dried over sodium sulfate and concentrated to yield 1-[6-(4-fluorophenyl)pyrazolo[1,5-a]pyridine-3-yl]ethanone (8, 260.2 mg, 1.02 mmol, 94% yield). MS APCI: $[M+H]^+$ m/z 255.3.

Step D: Thiazole Formation

Part 1: α-Bromination (Literature Reference: Keith, J. M.; Gomez, L. A.; Barbier, A. J.; Wilson, S. J.; Boggs, J. D.; Lord, B.; Mazur, C.; Aluisio, L.;. Lovenberg, T. W.; Carruthers, N. I. *Bio. Med. Chem. Lett.* 2007, 4374.)

Bromine (57.9 μL, 1.13 mmol) was added to a solution of 1-[6-(4-fluorophenyl)pyrazolo[1,5-a]pyridine-3-yl]ethanone (8, 197 mg, 0.775 mmol) in AcOH (1 mL) and hydrobromic acid (88 μL, 0.775 mmol). The reaction was heated to 50° C. for 2 hours after which an aqueous solution of 10% $Na_2S_2SO_3$ (5 mL) and dichloromethane (10 mL) were added to the reaction. The organic was collected and washed with a saturated solution of sodium bicarbonate (10 mL), dried over sodium sulfate and concentrated. The reaction was purified by column chromatography (10% acetone in hexanes) to yield 2-bromo-1-[6-(4-fluorophenyl)pyrazolo[1,5-a]pyridine-3-yl]ethanone (9, 220.4 mg, 0.662 mmol, 85% yield). MS APCI: $[M+H]^+$ m/z 334.2.

Part 2: Condensation

Ethyl thiooxamate (132 mg, 0.991 mmol) was added to a solution of 2-bromo-1-[6-(4-fluorophenyl)pyrazolo[1,5-a]pyridine-3-yl]ethanone (8, 220 mg, 0.660 mmol) in toluene (6.6 mL). The system is brought to reflux and was stirred 8 hours after which solvent was removed under reduced pressure and purified by column chromatography (10-20% acetone in hexanes, linear gradient) to quantitatively yield ethyl 4-[6-(4-fluorophenyl)pyrazolo[1,5-a]pyridine-3-yl]-1,3-thaizole-2-carboxylate (9, 243 mg, 0.66 mmol). MS APCI: $[M+H]^+$ m/z 368.4.

Part 3: Chlorination

To a solution of ethyl 4-[6-(4-fluorophenyl)pyrazolo[1,5-a]pyridine-3-yl]-1,3-thaizole-2-carboxylate (9, 276 mg, 0.751 mmol) in DCM (7.5 mL) is added NCS (100 mg, 0.751 mmol) at room temperature. After 15 minutes the reaction was quenched by an aqueous solution of 10% $Na_2S_2SO_3$ (5 mL). The organic was collected, dried over sodium sulfate, and concentrated. The reaction was purified by column chromatography (10% acetone in hexanes) to yield ethyl 5-chloro-4-[6-(4-fluorophenyl)pyrazolo[1,5-a]-pyridin-3-yl]-1,3-thaizole-2-carboxylate (10, 162 mg, 0.40 mmol, 54% yield). MS APCI: $[M+H]^+$ m/z 402.8.

Step E: Coupling

Part 1: Saponification

Lithium hydroxide (9.60 mg, 0.401 mmol) was added to a solution of ethyl 5-chloro-4-[6-(4-fluorophenyl)pyrazolo[1,5-a]pyridin-3-yl]-1,3-thaizole-2-carboxylate (10, 161 mg, 0.40 mmol) in THF (1.5 mL), MeOH (154 μL) and water (308 μL). After stirring for 1 hour at room temperature, THF and MeOH were removed under reduced pressure and the aqueous was acidified with 1M HCl. The product was collected by filtration to yield 5-chloro-4-[6-(4-fluorophenyl)pyrazolo[1,5-a]-pyridin-3-yl]-1,3-thaizole-2-carboxylic acid (11, 69.9 mg, 0.187 mmol, 46.7% yield). MS APCI: $[M+H]^+$ m/z 374.8.

Part 2: Acid Chloride Formation

Thionyl chloride (539 μl, 7.38 mmol was added to 5-chloro-4-[6-(4-fluorophenyl)pyrazolo[1,5-a]-pyridin-3-yl]-1,3-thaizole-2-carboxylic acid (11, 69 mg, 0.185 mmol) before heating the system to 65° C. Excess thionyl chloride was removed under reduced pressure to provide 3-{5-chloro-2-[(chlorooxyl)carbonyl]-1,3-thiazol-4-yl}-6-(4-fluorophenyl)pyrazolo[1,5-a]pyridine (12) in quantitative yield (75.5 mg, 0.185 mmol). Crude material was analyzed after methanol quench to obtain the corresponding methyl ester product, MS APCI: $[M+H]^{30}$ m/z 388.8

Part 3: Amide Synthesis

3-{5-Chloro-2-[(chlorooxyl)carbonyl]-1,3-thiazol-4-yl]-6-(4-fluorophenyl)pyrazolo[1,5-a]-pyridine (12, 75.5 mg, 0.185 mmol) was dissolved in a minimum amount of DCM and added to a solution of tert-butyl [(1R,2R)-2-amino-3,3-difluorocyclohexyl]carbamate (28, 34.5 mg, 0.138 mmol) in DCM (690 μl). After 10 minutes, TFA (0.5 mL) was added to reaction. The reaction was concentrated and purified by column chromatography (10% MeOH in DCM) to afford N-[(1R,6R)-6-amino-2,2-difluorocyclohexyl]-5-chloro-4-[6-fluorophenyl)pyrazolo[1,5-a]pyridin-3-yl]-1,3-thiazole-2-carboxamide (13, 38 mg, 0.092 mmol, 66.9% yield). MS APCI: $[M+H]^+$ m/z 506.9, $^1$H NMR (500 MHz, MeOH-$d_5$): δ 8.89 (1H, s), 8.65 (1H, s), 8.33 (1H, d, J=9.29 Hz), 7.77-7.72

(3H, m), 7.26 (2H, t, J=8.68 Hz), 4.99-4.93 (1H, m), 3.78-3.72 (1H, m), 2.36-2.21 (1H, m), 2.21-2.11 (2H, m), 2.05-1.95 (2H, m), 1.91-1.82 (1H, m), 1.80-1.70 (1H, m).

Example 2

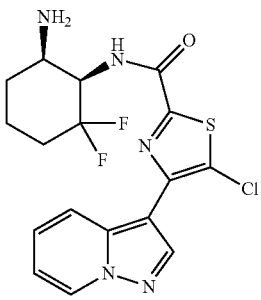 [SMILES: N[C@@H]1CCCC(F)(F)[C@@H]1NC(=O)c1nc(-c2cnn3ccccc23)c(Cl)s1]

N-[(1R,6R)-6-Amino-2,2-difluorocyclohexyl]-5-chloro-pyrazolo[1,5-a]pyridine-3-yl-1,3-thiazole-2-carboxamide (Scheme 1)

Synthesis began using commercially available pyrazolo[1,5-a]pyridine-3-carboxylic acid and by following the procedure outlined in example 1, part C, step 2 and all subsequent steps thereafter. Variation at the thiazole 5-position was introduced in example 1, part D, step 3 by the use of NCS or NBS or NIS to add a chloride or bromide or iodide, respectively. Note: In cases where 5-position is unfunctionalized, the halogenation step was not carried out. MS APCI: [M+H]+ m/z 412.9. $^1$H NMR (500 MHz, MeOH-d$_4$): δ 8.66-8.60 (2H, m), 8.28 (1H, d, J=9.0 Hz), 7.42 (1H, t, J=7.5 Hz), 7.04 (1H, t, J=7.5 Hz), 4.80 (1H, bs), 3.60 (1H, bs), 1.84-1.75 (1H, m), 1.72-1.55 (1H, m), 1.28-1.15 (4H, m), 0.95-0.89 (2H, m).

The following examples were prepared in an analogous manner of that described in example 2 with the use of known or commercial amines in step E, part 3.

| Name | Example # | Structure | LCMS M + H = |
|---|---|---|---|
| N-(2-Amino-3,3,3-trifluoro-1-phenylpropyl)-5-chloro-4-pyrazolo[1,5-a]pyridin-3-yl-1,3-thiazole-2-carboxamide | 3 | 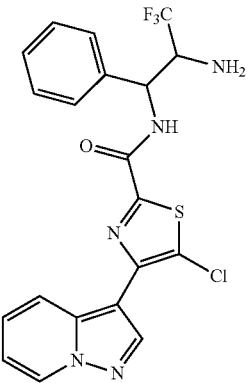 [SMILES: NC(C(NC(=O)c1nc(-c2cnn3ccccc23)c(Cl)s1)c1ccccc1)C(F)(F)F] | 467 |
| N-[(1R,2R]-2Amino-1,2-diphenylethyl)-5-chloro-4-pyrazolo[1,5-a]pyridin-3-yl-1,3-thiazole-2-carboxamide | 4 | 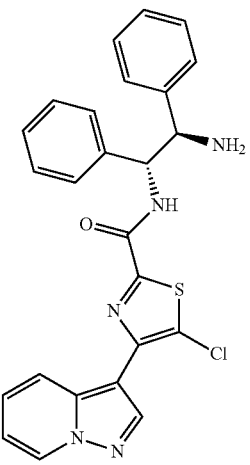 [SMILES: N[C@H](c1ccccc1)[C@H](NC(=O)c1nc(-c2cnn3ccccc23)c(Cl)s1)c1ccccc1] | 475 |

| Name | Example # | Structure | LCMS M + H = |
|---|---|---|---|
| 5-Chloro-4-pyrazolo[1,5-a]pyridin-3-yl-1,3-N-(2,2,2-trifluoroethyl)-1,3-thiazole-2-carboxamide | 5 | | 361 |
| N-[2-Amino-1-phenylethyl]-5-chloro-4-pyrazolo[1,5-a]pyridin-3-yl-1,3-thiazole-2-carboxamide | 6 | | 398 |
| N-[(1R,6S)-6-Amino-2,2-difluorocyclohexyl]-5-chloro-4-pyrazolo[1,5-a]pyridin-3-yl-1,3-thiazole-2-carboxamide | 7 | 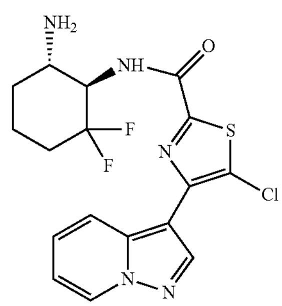 [SMILES: N[C@H]1CCCC(F)(F)[C@@H]1NC(=O)c1nc(-c2cnn3ccccc23)c(Cl)s1] | 412 |
| N-[(1R,6R)-6-Amino-2,2-difluorocyclohexyl]-5-bromo-4-pyrazolo[1,5-a]pyridin-3-yl-1,3-thiazole-2-carboxamide | 8 | 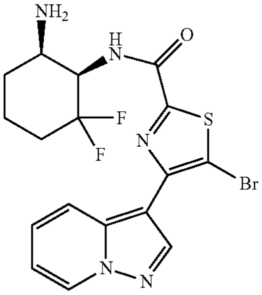 [SMILES: N[C@@H]1CCCC(F)(F)[C@@H]1NC(=O)c1nc(-c2cnn3ccccc23)c(Br)s1] | 456 |

-continued
| Name | Example # | Structure | LCMS M + H = |
|---|---|---|---|
| {4-[(5-Chloro-4-pyrazolo[1,5-a]pyridin-3-yl-1,3-thiazol-2-yl)carbonyl]piperazin-2-yl}methanol | 9 | 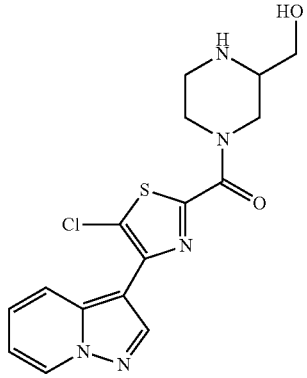 [SMILES: O=C(c1nc(-c2cnn3ccccc23)c(Cl)s1)N1CCNC(CO)C1] | 378 |
| 3-(5-Chloro-2-{[2-(difluoromethyl)piperazin-1-yl]carbonyl}-1,3-thiazol-4-yl)pyrazolo[1,5-a]pyridine | 10 | 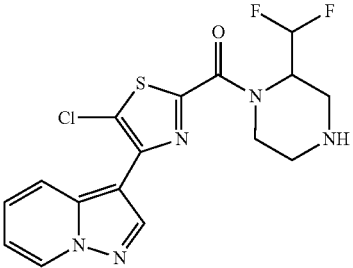 [SMILES: O=C(c1nc(-c2cnn3ccccc23)c(Cl)s1)N1CCNCC1C(F)F] | 398 |
| {4-[(5-Chloro-4-pyrazolo[1,5-a]pyridin-3-yl-1,3-thiazol-2-yl)carbonyl]morpholin-3-yl}methanol | 11 | 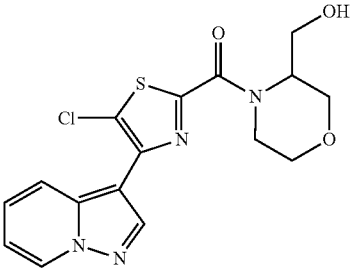 [SMILES: O=C(c1nc(-c2cnn3ccccc23)c(Cl)s1)N1CCOCC1CO] | 379 |
| 5-Chloro-N-(4-hydroxy-1,1-dioxidotetrahydro-3-thienyl)-4-pyrazolo[1,5-a]pyridin-3-yl-1-3-thiazole-2-carboxamide | 12 | 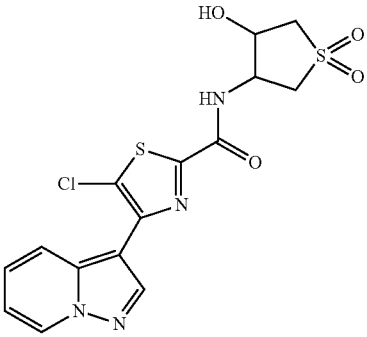 [SMILES: O=C(NC1CS(=O)(=O)CC1O)c1nc(-c2cnn3ccccc23)c(Cl)s1] | 413 |

-continued

| Name | Example # | Structure | LCMS M + H = |
|---|---|---|---|
| 3-(5-Chloro-2-{[2-(trifluoromethyl)piperazin-1-yl]carbonyl}-1,3-thiazol-4-yl)pyrazolo[1,5-a]pyridine | 13 | 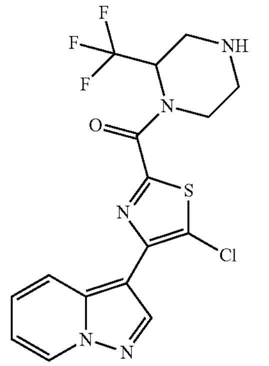 [SMILES: O=C(c1nc(-c2cnn3ccccc23)c(Cl)s1)N1CCNCC1C(F)(F)F] | 416 |
| (3R,4R)-1-[(5-Chloro-4-pyrazolo[1,5-a]pyridin-3-yl-1,3-thiazol-2-yl)carbonyl]-3-fluoropiperidin-4-amine | 14 | 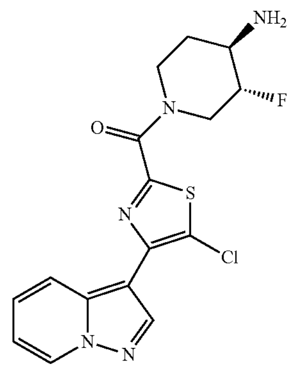 [SMILES: N[C@@H]1CCN(C(=O)c2nc(-c3cnn4ccccc34)c(Cl)s2)C[C@H]1F] | 380 |
| (3S,4R)-1-[(5-Chloro-4-pyrazolo[1,5-a]pyridin-3-yl-1,3-thiazol-2-yl)carbonyl]-3-fluoropiperidin-4-amine | 15 | 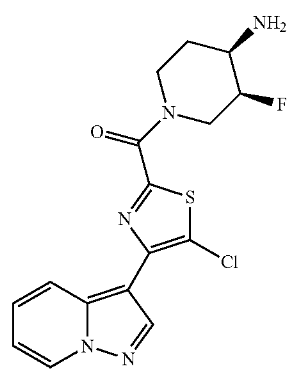 [SMILES: N[C@@H]1CCN(C(=O)c2nc(-c3cnn4ccccc34)c(Cl)s2)C[C@@H]1F] | 380 |
| N-[(3R,4R)-4-amino-1-benzylpyrrolidin-3-yl]-5-chloro-4-pyrazolo[1,5-a]pyridin-3-yl-1,3-thiazole-2-carboxamide | 16 | 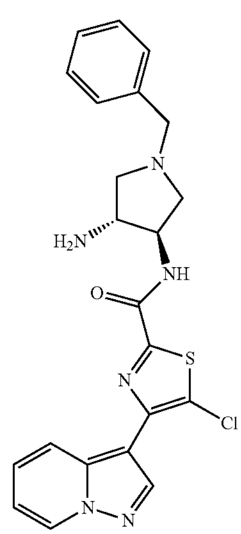 [SMILES: N[C@@H]1CN(Cc2ccccc2)C[C@H]1NC(=O)c1nc(-c2cnn3ccccc23)c(Cl)s1] | 453 |

-continued

| Name | Example # | Structure | LCMS M + H = |
|---|---|---|---|
| 2-[(5-Chloro-4-pyrazolo[1,5-a]pyridin-3-yl-1,3-thiazol-2-yl)carbonyl]-2,3-dihydro-1H-spiro[isoquinoline-4,4'-piperidine] | 17 | 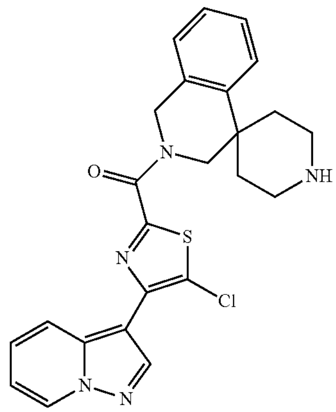 [SMILES: O=C(c1nc(-c2cnn3ccccc23)c(Cl)s1)N1Cc2ccccc2C2(CCNCC2)C1] | 464 |
| 5-Chloro-N-[(4-phenylpiperidin-4-yl)methyl]-4-pyrazolo[1,5-a]pyridin-3-yl-1,3-thiazole-2-carboxamide | 18 | 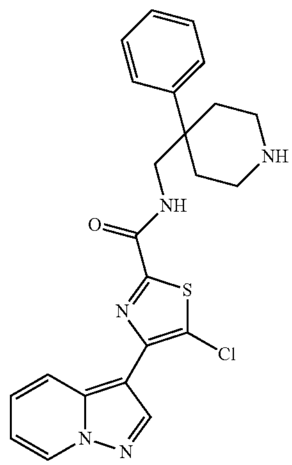 [SMILES: O=C(NCC1(c2ccccc2)CCNCC1)c1nc(-c2cnn3ccccc23)c(Cl)s1] | 452 |
| 5-Chloro-N-(2,3-dihydrospiro[indene-1,4'-piperidin]-3-yl)-4-pyrazolo[1,5-a]pyridin-3-yl-1,3-thiazole-2-carboxamide | 19 | 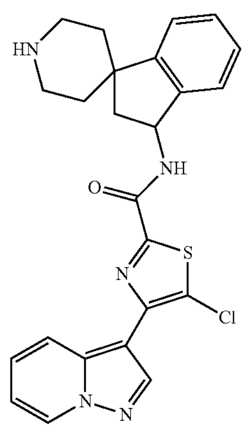 [SMILES: O=C(NC1CC2(CCNCC2)c2ccccc21)c1nc(-c2cnn3ccccc23)c(Cl)s1] | 464 |
| 5-Chloro-N-[(3S)-1-methylpyrrolidin-3-yl]-4-pyrazolo[1,5-a]pyridin-3-yl-1,3-thiazole-2-carboxamide | 20 | 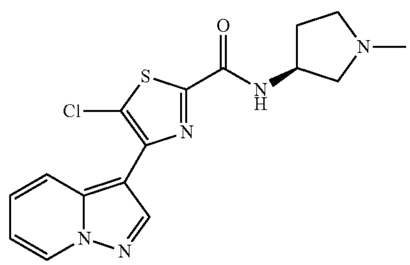 [SMILES: CN1CC[C@H](NC(=O)c2nc(-c3cnn4ccccc34)c(Cl)s2)C1] | 362 |

| Name | Example # | Structure | LCMS M + H = |
|---|---|---|---|
| 5-Chloro-4-pyrazolo[1,5-a]pyridin-3-yl-N-(1,2,3,4-tetrahydroisoquinolin-1-ylmethyl)-1,3-thiazole-2-carboxamide | 21 | 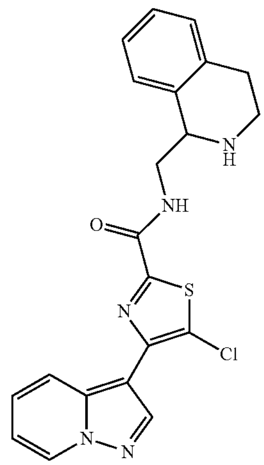 [SMILES: O=C(NCC1NCCc2ccccc21)c1nc(-c2cnn3ccccc23)c(Cl)s1] | 424 |
| {3-Amino-1-[(5-chloro-4-pyrazolo[1,5-a]pyridin-3-yl-1,3-thiazol-2-yl)carbonyl]pyrrolidin-3-yl}methanol | 22 | 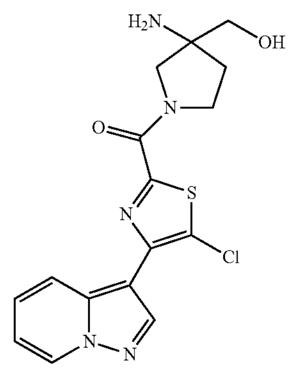 [SMILES: NC1(CO)CCN(C(=O)c2nc(-c3cnn4ccccc34)c(Cl)s2)C1] | 378 |
| 5-Chloro-N-piperidin-3-yl-4-pyrazolo[1,5-a]pyridin-3-yl-1,3-thiazole-2-carboxamide | 23 | 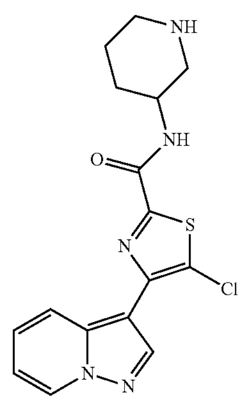 [SMILES: O=C(NC1CCCNC1)c1nc(-c2cnn3ccccc23)c(Cl)s1] | 362 |
| 1-[(5-Chloro-4-pyrazolo[1,5-a]pyridin-3-yl-1,3-thiazol-2-yl)carbonyl]pyrrolidin-3-amine | 24 | 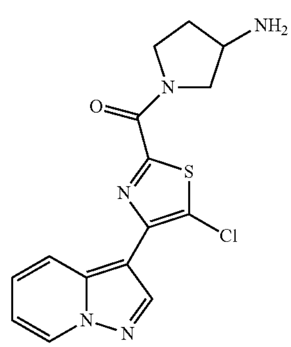 [SMILES: NC1CCN(C(=O)c2nc(-c3cnn4ccccc34)c(Cl)s2)C1] | 348 |

-continued
| Name | Example # | Structure | LCMS M + H = |
|---|---|---|---|
| 3-[5-Chloro-2-(piperazin-1-ylcarbonyl)-1,3-thiazol-4-yl]pyrazolo[1,5-a]pyridine | 25 | 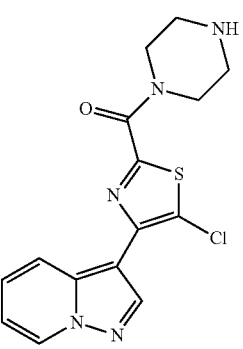 [SMILES: O=C(c1nc(-c2cnn3ccccc23)c(Cl)s1)N1CCNCC1] | 348 |
| N-(2-Aminoethyl)-5-chloro-N-methyl-4-pyrazolo[1,5-a]pyridin-3-yl-1,3-thiazole-2-carboxamide | 26 | 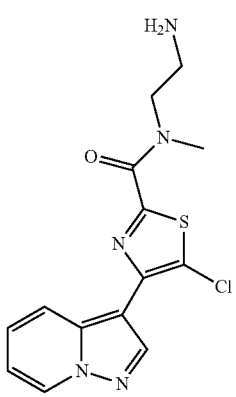 [SMILES: CN(CCN)C(=O)c1nc(-c2cnn3ccccc23)c(Cl)s1] | 336 |
| N-(2-Aminoethyl)-5-chloro-N-ethyl-4-pyrazolo[1,5-a]pyridin-3-yl-1,3-thiazole-2-carboxamide | 27 | 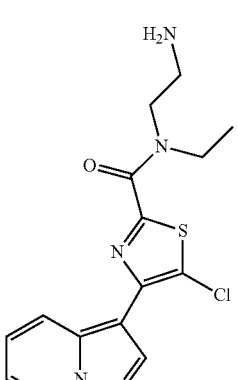 | 350 |
| 1-[(5-Chloro-4-pyrazolo[1,5-a]pyridin-3-yl-1,3-thiazol-2-yl)carbonyl]-N-methylpyrrolidin-3-amine | 28 | 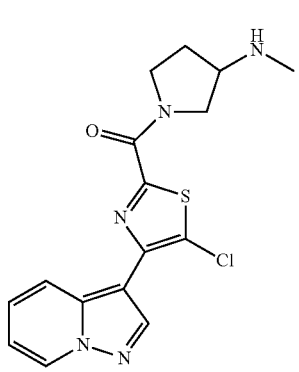 [SMILES: CNC1CCN(C(=O)c2nc(-c3cnn4ccccc34)c(Cl)s2)C1] | 362 |

| Name | Example # | Structure | LCMS M + H = |
|---|---|---|---|
| 3-{5-Chloro-2-[(2-methylpiperazin-1-yl)carbonyl]-1,3-thiazol-4-yl}pyrazolo[1,5-a]pyridine | 29 | 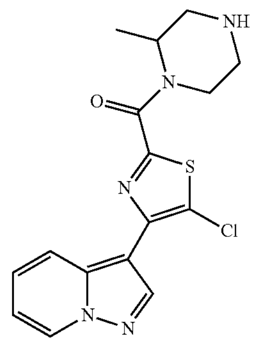 [SMILES: CC1CNCCN1C(=O)c1nc(-c2cnn3ccccc23)c(Cl)s1] | 362 |
| N-[(1-Aminocyclopentyl)methyl]-5-chloro-4-pyrazolo[1,5-a]pyridin-3-yl-1,3-thiazole-2-carboxamide | 30 | 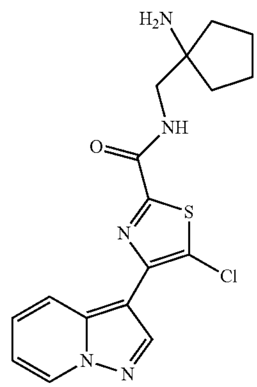 [SMILES: NC1(CNC(=O)c2nc(-c3cnn4ccccc34)c(Cl)s2)CCCC1] | 376 |
| N-[(1-Aminocyclohexyl)methyl]-5-chloro-4-pyrazolo[1,5-a]pyridin-3-yl-1,3-thiazole-2-carboxamide | 31 | 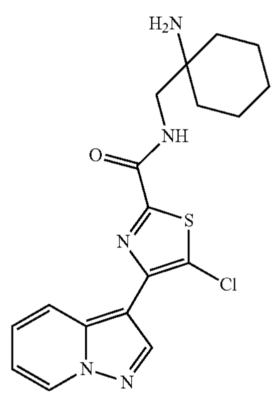 [SMILES: NC1(CNC(=O)c2nc(-c3cnn4ccccc34)c(Cl)s2)CCCCC1] | 390 |
| 1-[(5-Chloro-4-pyrazolo[1,5-a]pyridin-3-yl-1,3-thiazol-2-yl)carbonyl]-1,2,3,4-tetrahydroquinolin-3-amine | 32 | 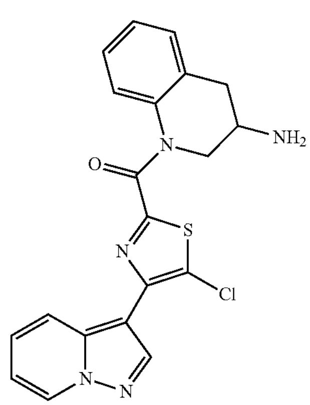 [SMILES: NC1Cc2ccccc2N(C(=O)c2nc(-c3cnn4ccccc34)c(Cl)s2)C1] | 410 |

-continued
| Name | Example # | Structure | LCMS M + H = |
|---|---|---|---|
| N-[(1-Amino-2-phenylethyl)-5-chloro-4-pyrazolo[1,5-a]pyridin-3-yl-1,3-thiazole-2-carboxamide | 33 | 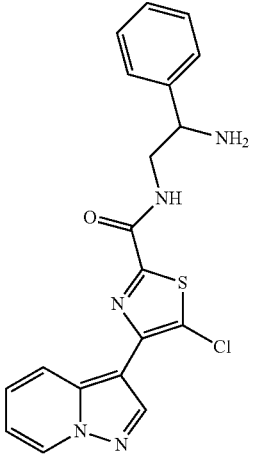 [SMILES: NC(CNC(=O)c1nc(-c2cnn3ccccc23)c(Cl)s1)c1ccccc1] | 398 |
| N-(2-Aminoethyl)-5-chloro-4-pyrazolo[1,5-a]pyridin-3-yl-1,3-thiazole-2-carboxamide | 34 | 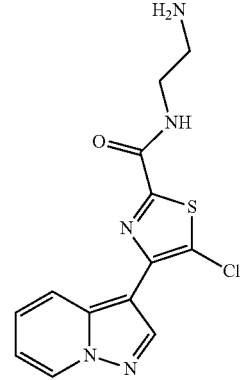 [SMILES: NCCNC(=O)c1nc(-c2cnn3ccccc23)c(Cl)s1] | 322 |
| 5-Chloro-4-pyrazolo[1,5-a]pyridin-3-yl-N-pyrrolidin-3-yl-1,3-thiazole-2-carboxamide | 35 | 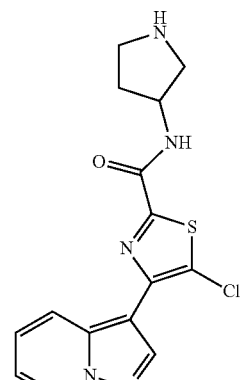 | 348 |

-continued
| Name | Example # | Structure | LCMS M + H = |
|---|---|---|---|
| 3-{5-Chloro-2-[(3-methylpiperazin-1-yl)carbonyl]-1,3-thiazol-4-yl}pyrazolo[1,5-a]pyridine | 36 | 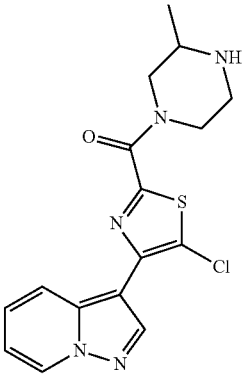 [SMILES: CC1CN(C(=O)c2nc(-c3cnn4ccccc34)c(Cl)s2)CCN1] | 362 |
| N-(3-Aminocyclohexyl)-5-chloro-4-pyrazolo[1,5-a]pyridin-3-yl-1,3-thiazole-2-carboxamide | 37 | 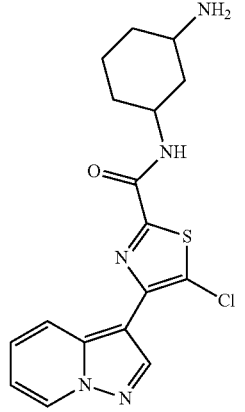 [SMILES: NC1CCCC(NC(=O)c2nc(-c3cnn4ccccc34)c(Cl)s2)C1] | 376 |
| 3-{5-Chloro-2-[(3-methylpiperazin-1-yl)carbonyl]-1,3-thiazol-4-yl}pyrazolo[1,5-a]pyridine | 38 | 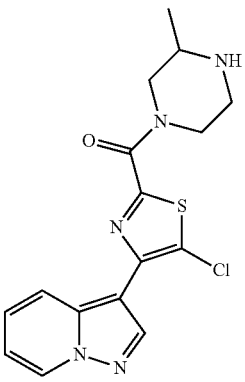 [SMILES: CC1CN(C(=O)c2nc(-c3cnn4ccccc34)c(Cl)s2)CCN1] | 362 |
| N-(3-Aminocyclohexyl)-5-chloro-4-pyrazolo[1,5-a]pyridin-3-yl-1,3-thiazole-2-carboxamide | 39 | 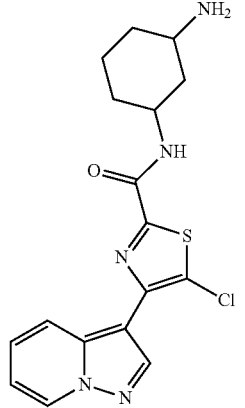 [SMILES: NC1CCCC(NC(=O)c2nc(-c3cnn4ccccc34)c(Cl)s2)C1] | 376 |

-continued
| Name | Example # | Structure | LCMS M + H = |
|---|---|---|---|
| 1-{1-[(5-Chloro-4-pyrazolo[1,5-a]pyridin-3-yl-1,3-thiazol-2-yl)carbonyl]-4-phenylpiperidin-4-yl}methanamine | 40 | 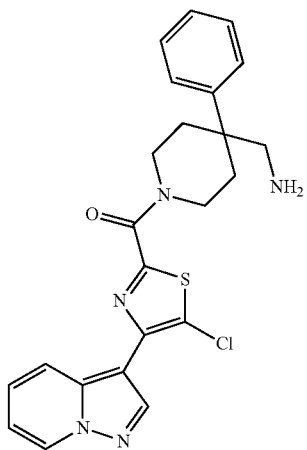 [SMILES: NCC1(c2ccccc2)CCN(C(=O)c2nc(-c3cnn4ccccc34)c(Cl)s2)CC1] | 452 |
| N-(4-Amino-1,1-dioxidotetrahydro-3-thienyl)-5-chloro-4-pyrazolo[1,5-a]pyridin-3-yl-1,3-thiazole-2-carboxamide | 41 | 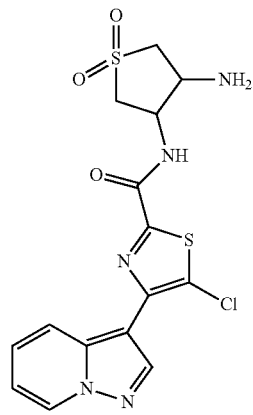 [SMILES: NC1CS(=O)(=O)CC1NC(=O)c1nc(-c2cnn3ccccc23)c(Cl)s1] | 412 |
| N-(2-Amino-2-methylpropyl)-5-chloro-4-pyrazolo[1,5-a]pyridin-3-yl-1,3-thiazole-2-carboxamide | 42 | 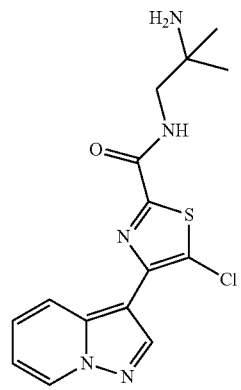 [SMILES: CC(C)(N)CNC(=O)c1nc(-c2cnn3ccccc23)c(Cl)s1] | 350 |

-continued

| Name | Example # | Structure | LCMS M + H = |
|---|---|---|---|
| 5-Chloro-N-(2-oxopiperidin-3-yl)-4-pyrazolo[1,5-a]pyridin-3-yl-1,3-thiazole-2-carboxamide | 43 | 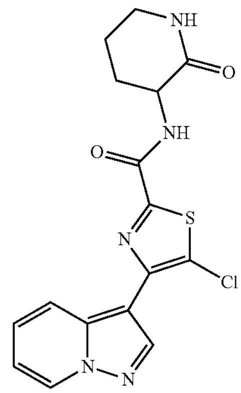 [SMILES: O=C(NC1CCCNC1=O)c1nc(-c2cnn3ccccc23)c(Cl)s1] | 376 |
| N-[(1S,2R)-2-aminocyclopentyl]-5-chloro-4-pyrazolo[1,5-a]pyridin-3-yl-1,3-thiazole-2-carboxamide | 44 | 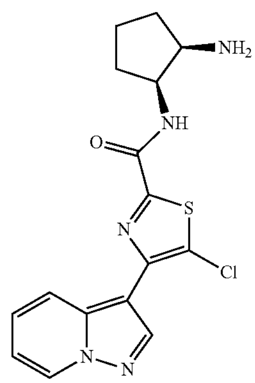 [SMILES: N[C@@H]1CCC[C@@H]1NC(=O)c1nc(-c2cnn3ccccc23)c(Cl)s1] | 362 |
| N-[(1-aminocycloheptyl)methyl]-5-chloro-4-pyrazolo[1,5-a]pyridin-3-yl-1,3-thiazole-2-carboxamide | 45 | 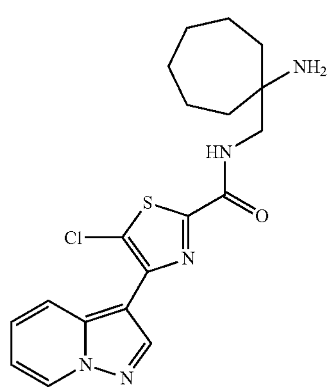 [SMILES: NC1(CNC(=O)c2nc(-c3cnn4ccccc34)c(Cl)s2)CCCCCC1] | 404 |
| N-[(1R,6S)-6-Amino-2,2-difluorocyclohexyl]-5-chloro-4-pyrazolo[1,5-a]pyridin-3-yl-1,3-thiazole-2-carboxamide | 46 | 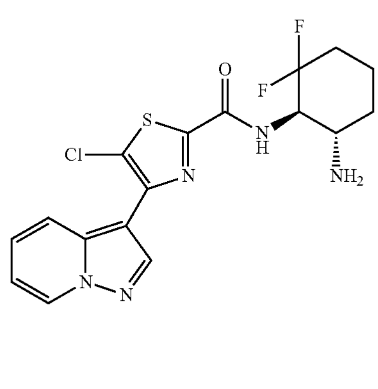 [SMILES: N[C@H]1CCCC(F)(F)[C@@H]1NC(=O)c1nc(-c2cnn3ccccc23)c(Cl)s1] | 412 |

| Name | Example # | Structure | LCMS M + H = |
|---|---|---|---|
| 5-Chloro-N-(1-methyl-2-oxopyrrolidin-3-yl)-4-pyrazolo[1,5-a]pyridin-3-yl-1,3-thiazole-2-carboxamide | 47 | 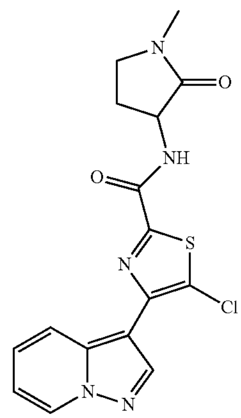 [SMILES: CN1CCC(NC(=O)c2nc(-c3cnn4ccccc34)c(Cl)s2)C1=O] | 376 |
| 5-Chloro-N-(3,3-difluorocyclopentyl)-4-pyrazolo[1,5-a]pyridin-3-yl-1,3-thiazole-2-carboxamide | 48 | 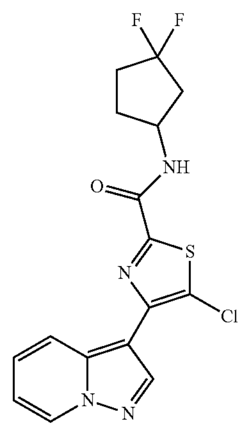 [SMILES: O=C(NC1CCC(F)(F)C1)c1nc(-c2cnn3ccccc23)c(Cl)s1] | 383 |
| N-(2-Azetidin-1-yl-3,3,3-trifluoropropyl)-5-chloro-4-pyrazolo[1,5-a]pyridin-3-yl-1,3-thiazole-2-carboxamide | 49 | 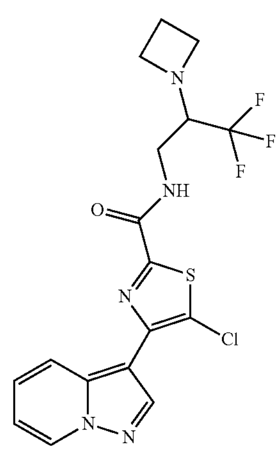 [SMILES: O=C(NCC(N1CCC1)C(F)(F)F)c1nc(-c2cnn3ccccc23)c(Cl)s1] | 430 |

-continued

| Name | Example # | Structure | LCMS M + H = |
|---|---|---|---|
| 3-[5-Chloro-2-[(morpholin-4-ylcarbonyl)-1,3-thiazol-4-yl]pyrazolo[1,5-a]pyridine | 50 | 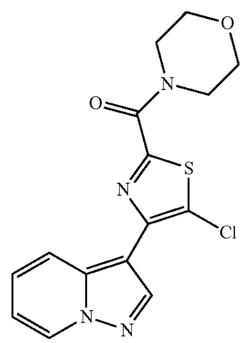 [SMILES: O=C(c1nc(-c2cnn3ccccc23)c(Cl)s1)N1CCOCC1] | 349 |
| 3-{5-Chloro-2-[(2,6-dimethylmorpholin-4-yl)carbonyl]-1,3-thiazol-4-yl}pyrazolo[1,5-a]pyridine | 51 | 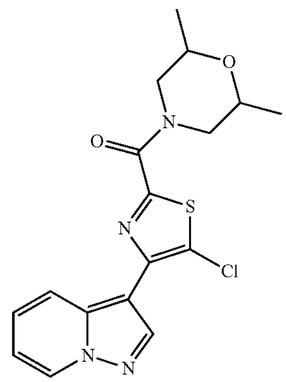 [SMILES: CC1CN(C(=O)c2nc(-c3cnn4ccccc34)c(Cl)s2)CC(C)O1] | 377 |
| 3-{5-Chloro-2-[(4-methylpiperazin-1-yl)carbonyl]-1,3-thiazol-4-yl}pyrazolo[1,5-a]pyridine | 52 | 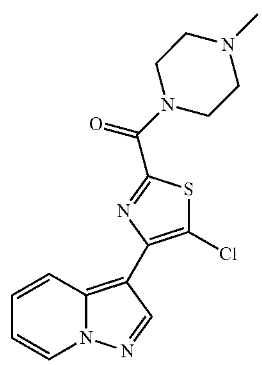 [SMILES: CN1CCN(C(=O)c2nc(-c3cnn4ccccc34)c(Cl)s2)CC1] | 362 |
| 5-Chloro-N-(2-morpholin-4-ylethyl)-4-pyrazolo[1,5-a]pyridin-3-yl-1,3-thiazole-2-carboxamide | 53 | 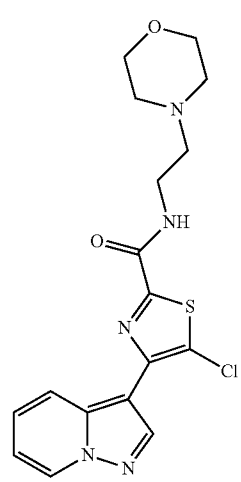 [SMILES: O=C(NCCN1CCOCC1)c1nc(-c2cnn3ccccc23)c(Cl)s1] | 392 |

| Name | Example # | Structure | LCMS M + H = |
|---|---|---|---|
| 1-[(5-Chloro-4-pyrazolo[1,5-a]pyridin-3-yl-1,3-thiazol-2-yl)carbonyl]piperidin-4-ol | 54 | 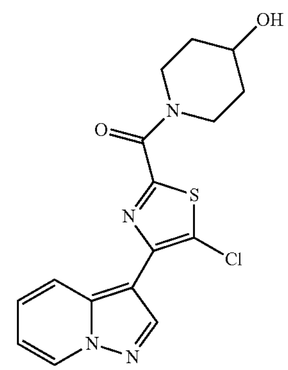 [SMILES: O=C(c1nc(-c2cnn3ccccc23)c(Cl)s1)N1CCC(O)CC1] | 363 |
| 1-[(5-Chloro-4-pyrazolo[1,5-a]pyridin-3-yl-1,3-thiazol-2-yl)carbonyl]-N,N-dimethylpiperidin-4-amine | 55 | 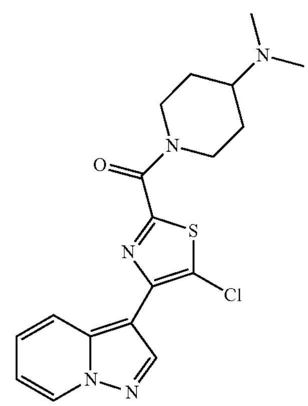 [SMILES: CN(C)C1CCN(C(=O)c2nc(-c3cnn4ccccc34)c(Cl)s2)CC1] | 390 |
| 5-Chloro-N-[1-(hydroxymethyl)-2-methylpropyl]-4-pyrazolo[1,5-a]pyridin-3-yl-1,3-thiazole-2-carboxamide | 56 | 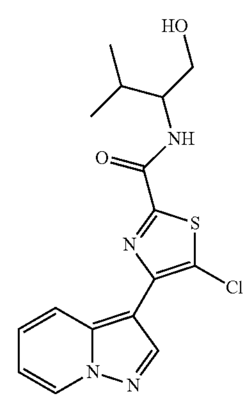 [SMILES: CC(C)C(CO)NC(=O)c1nc(-c2cnn3ccccc23)c(Cl)s1] | 365 |

| Name | Example # | Structure | LCMS M + H = |
|---|---|---|---|
| Diethyl{1-[(5-chloro-4-pyrazolo[1,5-a]pyridin-3-yl-1,3-thiazol-2-yl)carbonyl]piperidin-4-yl}phosphonate | 57 | 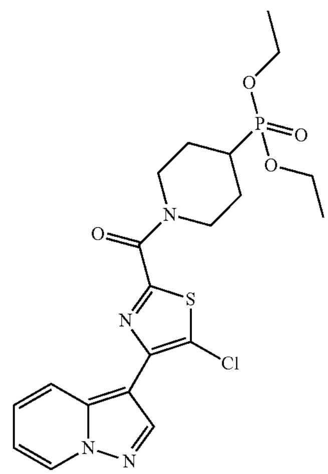 [SMILES: CCOP(=O)(OCC)C1CCN(C(=O)c2nc(-c3cnn4ccccc34)c(Cl)s2)CC1] | 483 |
| 5-Chloro-N-(2-hydroxycyclopentyl)-4-pyrazolo[1,5-a]pyridin-3-yl-1,3-thiazole-2-carboxamide | 58 | 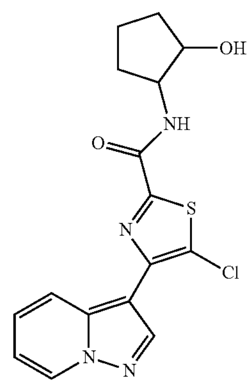 [SMILES: O=C(NC1CCCC1O)c1nc(-c2cnn3ccccc23)c(Cl)s1] | 363 |
| 5-Chloro-N-(2,3-dihydroxypropyl)-N-methyl-4-pyrazolo[1,5-a]pyridin-3-yl-1,3-thiazole-2-carboxamide | 59 | 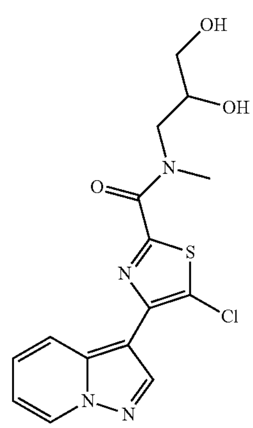 [SMILES: CN(CC(O)CO)C(=O)c1nc(-c2cnn3ccccc23)c(Cl)s1] | 367 |

| Name | Example # | Structure | LCMS M + H = |
|---|---|---|---|
| 5-Chloro-N-(hydroxy-2-methylpropyl)-4-pyrazolo[1,5-a]pyridin-3-yl-1,3-thiazole-2-carboxamide | 60 | 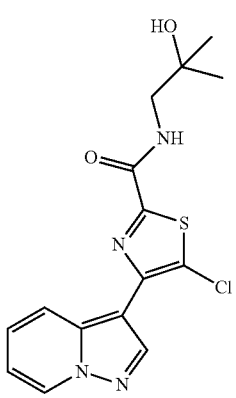 [SMILES: CC(C)(O)CNC(=O)c1nc(-c2cnn3ccccc23)c(Cl)s1] | 351 |
| 1-[(5-Chloro-4-pyrazolo[1,5-a]pyridin-3-yl-1,3-thiazol-2-yl)carbonyl]-N,N-dimethylpiperidin-3-amine | 61 | 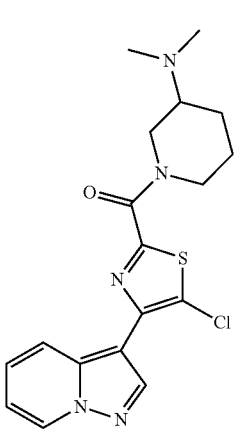 [SMILES: CN(C)C1CCCN(C(=O)c2nc(-c3cnn4ccccc34)c(Cl)s2)C1] | 390 |
| 5-Chloro-N-(2-oxopyrrolidin-3-yl)-4-pyrazolo[1,5-a]pyridin-3-yl-1,3-thiazole-2-carboxamide | 62 | 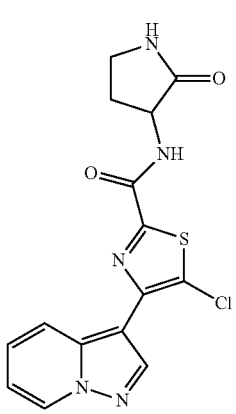 [SMILES: O=C(NC1CCNC1=O)c1nc(-c2cnn3ccccc23)c(Cl)s1] | 362 |

| Name | Example # | Structure | LCMS M + H = |
|---|---|---|---|
| 5-Chloro-N-[(3R)-1-isopropylpyrrolidin-3-yl]-4-pyrazolo[1,5-a]pyridin-3-yl-1,3-thiazole-2-carboxamide | 63 | 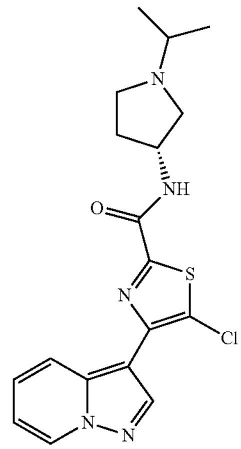 [SMILES: CC(C)N1CC[C@@H](NC(=O)c2nc(-c3cnn4ccccc34)c(Cl)s2)C1] | 390 |
| 5-Chloro-N-[(3S)-1-isopropylpyrrolidin-3-yl]-4-pyrazolo[1,5-a]pyridin-3-yl-1,3-thiazole-2-carboxamide | 64 | 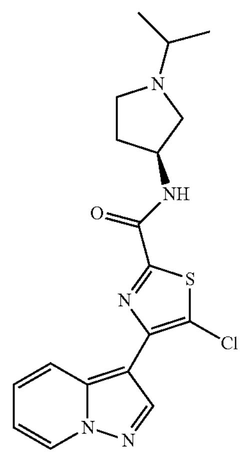 [SMILES: CC(C)N1CC[C@H](NC(=O)c2nc(-c3cnn4ccccc34)c(Cl)s2)C1] | 390 |
| 5-Chloro-N-[2-(dimethylamino)-3,3,3-trifluoropropyl]-4-pyrazolo[1,5-a]pyridin-3-yl-1,3-thiazole-2-carboxamide | 66 | 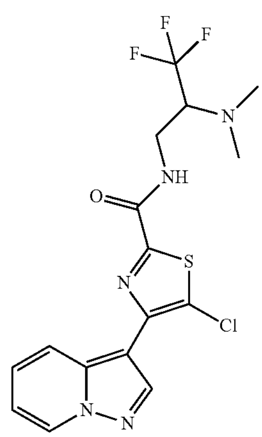 [SMILES: CN(C)C(CNC(=O)c1nc(-c2cnn3ccccc23)c(Cl)s1)C(F)(F)F] | 418 |

| Name | Example # | Structure | LCMS M + H = |
|---|---|---|---|
| 5-Chloro-4-pyrazolo[1,5-a]pyridin-3-yl-N-[3,3,3-trifluoro-2-(3-fluoroazetidin-1-yl)propyl]-1,3-thiazole-2-carboxamide | 67 | 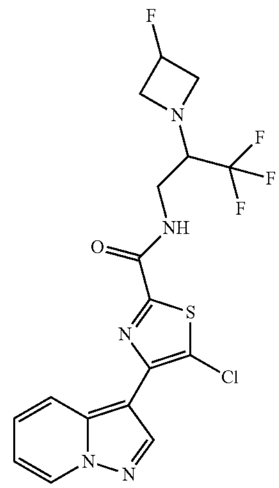 [SMILES: O=C(NCC(N1CC(F)C1)C(F)(F)F)c1nc(-c2cnn3ccccc23)c(Cl)s1] | 448 |
| 5-Chloro-N-(4-hydroxy-1,1-dioxidotetrahydro-3-thienyl)-4-pyrazolo[1,5-a]pyridin-3-yl-1,3-thiazole-2-carboxamide | 68 | 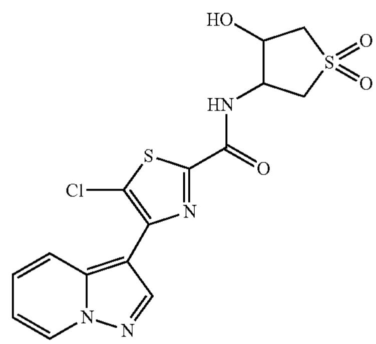 [SMILES: O=C(NC1CS(=O)(=O)CC1O)c1nc(-c2cnn3ccccc23)c(Cl)s1] | 413 |
| (2S)-2-Anilino-2-phenylethyl 5-chloro-4-pyrazolo[1,5-a]pyridin-3-yl-1,3-thiazole-2-carboxylate | 69 | 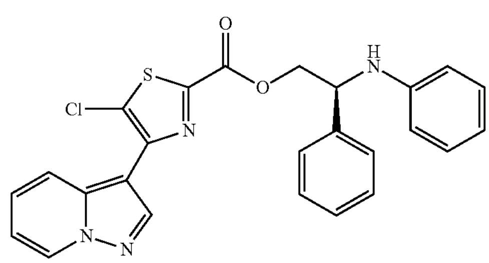 [SMILES: O=C(OC[C@@H](Nc1ccccc1)c1ccccc1)c1nc(-c2cnn3ccccc23)c(Cl)s1] | 475 |
| (2S)-2-Anilinopropyl 5-chloro-4-pyrazolo[1,5-a]pyridin-3-yl-1,3-thiazole-2-carboxylate | 70 | 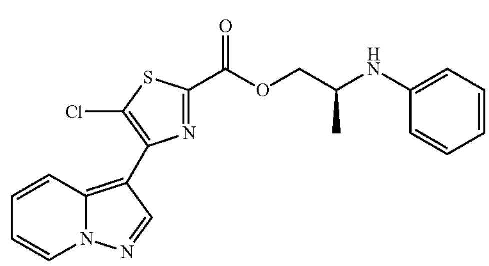 [SMILES: C[C@@H](COC(=O)c1nc(-c2cnn3ccccc23)c(Cl)s1)Nc1ccccc1] | 413 |
| 5-Chloro-N-[(1S)-2-hydroxy-1-methylethyl]-N-phenyl-4-pyrazolo[1,5-a]pyridin-3-yl-1,3-thiazole-2-carboxamide | 71 | 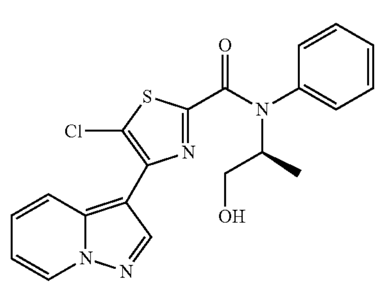 [SMILES: C[C@@H](CO)N(C(=O)c1nc(-c2cnn3ccccc23)c(Cl)s1)c1ccccc1] | 413 |

| Name | Example # | Structure | LCMS M + H = |
|---|---|---|---|
| 5-Chloro-N-phenyl-4-pyrazolo[1,5-a]pyridin-3-yl-N-(2,2,2-trifluoroethyl)-1,3-thiazole-2-carboxamide | 72 | 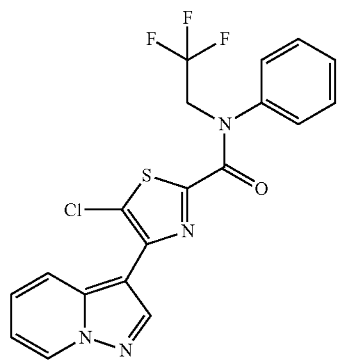 [SMILES: O=C(c1nc(-c2cnn3ccccc23)c(Cl)s1)N(CC(F)(F)F)c1ccccc1] | 437 |
| 5-Chloro-N-isopropyl-4-pyrazolo[1,5-a]pyridin-3-yl-1,3-thiazole-2-carboxamide | 73 | 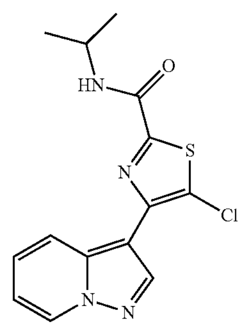 [SMILES: CC(C)NC(=O)c1nc(-c2cnn3ccccc23)c(Cl)s1] | 321 |
| 5-Chloro-N-ethyl-N-methyl-4-pyrazolo[1,5-a]pyridin-3-yl-1,3-thiazole-2-carboxamide | 74 | 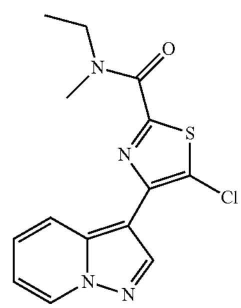 [SMILES: CCN(C)C(=O)c1nc(-c2cnn3ccccc23)c(Cl)s1] | 321 |
| 5-Chloro-N-(2-hydroxyethyl)-4-pyrazolo[1,5-a]pyridin-3-yl-1,3-thiazole-2-carboxamide | 75 | 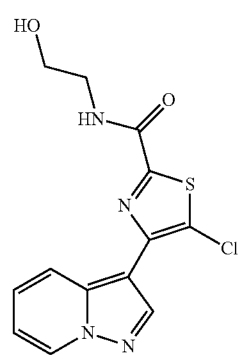 [SMILES: O=C(NCCO)c1nc(-c2cnn3ccccc23)c(Cl)s1] | 323 |

-continued

| Name | Example # | Structure | LCMS M + H = |
|---|---|---|---|
| 5-Chloro-N-ethyl-4-pyrazolo[1,5-a]pyridin-3-yl-1,3-thiazole-2-carboxamide | 76 | 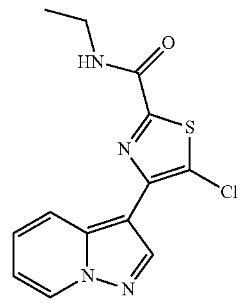 [SMILES: CCNC(=O)c1nc(-c2cnn3ccccc23)c(Cl)s1] | 307 |
| 5-Chloro-N-(2-methoxyethyl)-4-pyrazolo[1,5-a]pyridin-3-yl-1,3-thiazole-2-carboxamide | 77 | 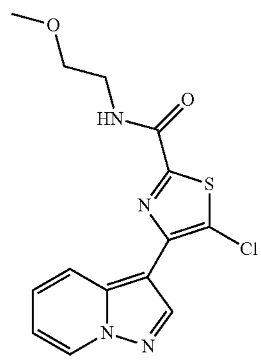 [SMILES: COCCNC(=O)c1nc(-c2cnn3ccccc23)c(Cl)s1] | 337 |
| 3-[5-Chloro-2-(piperidin-1-ylcarbonyl)-1,3-thiazol-4-yl]pyrazolo[1,5-a]pyridine | 78 | 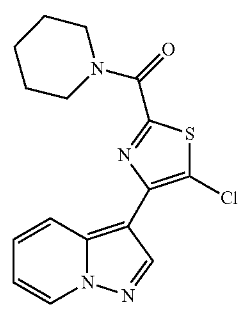 [SMILES: O=C(c1nc(-c2cnn3ccccc23)c(Cl)s1)N1CCCCC1] | 347 |
| 5-Chloro-4-pyrazolo[1,5-a]pyridin-3-yl-N-pyridin-3-yl-1,3-thiazole-2-carboxamide | 79 | 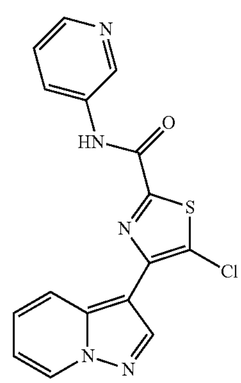 [SMILES: O=C(Nc1cccnc1)c1nc(-c2cnn3ccccc23)c(Cl)s1] | 356 |

-continued

| Name | Example # | Structure | LCMS M + H = |
|---|---|---|---|
| 5-Chloro-N-cyclohexyl-4-pyrazolo[1,5-a]pyridin-3-yl-1,3-thiazole-2-carboxamide | 80 | 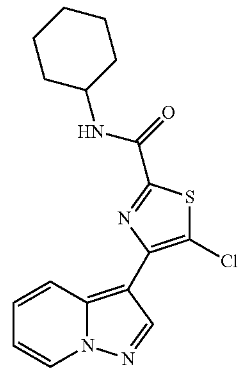 [SMILES: O=C(NC1CCCCC1)c1nc(-c2cnn3ccccc23)c(Cl)s1] | 361 |
| N-Benzyl-5-chloro-4-pyrazolo[1,5-a]pyridin-3-yl-1,3-thiazole-2-carboxamide | 81 | 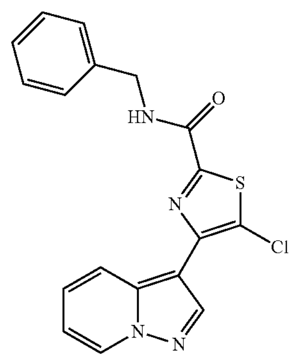 [SMILES: O=C(NCc1ccccc1)c1nc(-c2cnn3ccccc23)c(Cl)s1] | 369 |
| 5-Chloro-4-pyrazolo[1,5-a]pyridin-3-yl-N-(pyridin-3-ylmethyl)-1,3-thiazole-2-carboxamide | 82 | 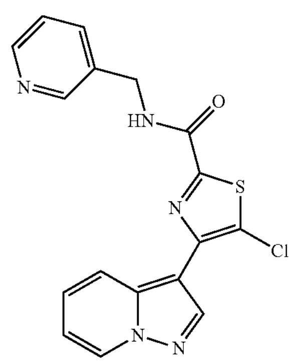 [SMILES: O=C(NCc1cccnc1)c1nc(-c2cnn3ccccc23)c(Cl)s1] | 370 |
| 5-Chloro-4-pyrazolo[1,5-a]pyridin-3-yl-N-(2-thienylmethyl)-1,3-thiazole-2-carboxamide | 83 | 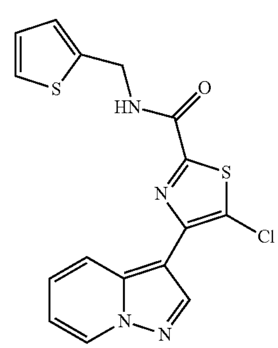 [SMILES: O=C(NCc1cccs1)c1nc(-c2cnn3ccccc23)c(Cl)s1] | 375 |

| Name | Example # | Structure | LCMS M + H = |
|---|---|---|---|
| 5-Chloro-4-pyrazolo[1,5-a]pyridin-3-yl-N-(2-pyrrolidin-1-ylethyl)-1,3-thiazole-2-carboxamide | 84 | 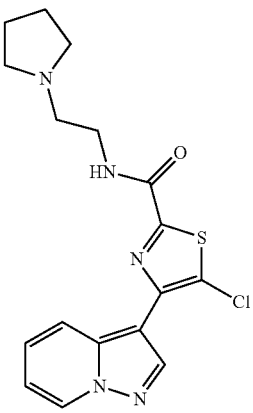 [SMILES: O=C(NCCN1CCCC1)c1nc(-c2cnn3ccccc23)c(Cl)s1] | 376 |
| 5-Chloro-1-(2,6-dimethylphenyl)-4-pyrazolo[1,5-a]pyridin-3-yl-1,3-thiazole-2-carboxamide | 85 | 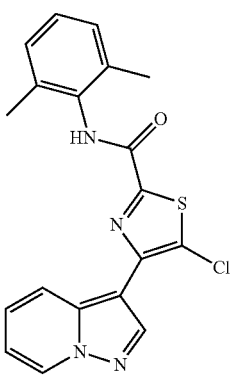 [SMILES: Cc1cccc(C)c1NC(=O)c1nc(-c2cnn3ccccc23)c(Cl)s1] | 383 |
| 3-{2-[(4-Acetylpiperazin-1-yl)carbonyl]-5-chloro-1,3-thiazol-4-yl}pyrazolo[1,5-a]pyridine | 86 | 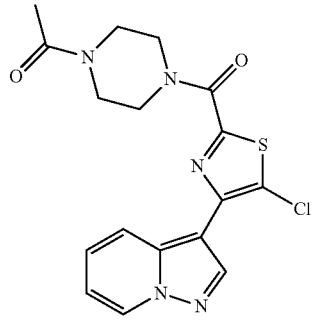 [SMILES: CC(=O)N1CCN(C(=O)c2nc(-c3cnn4ccccc34)c(Cl)s2)CC1] | 390 |
| 5-Chloro-N-(3-phenylpropyl)-4-pyrazolo[1,5-a]pyridin-3-yl-1,3-thiazole-2-carboxamide | 87 | 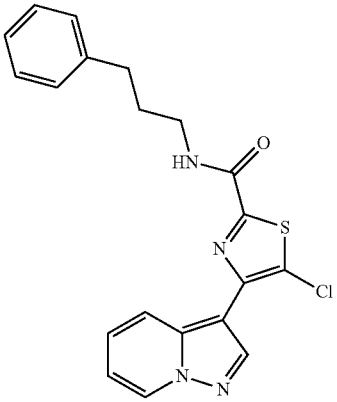 [SMILES: O=C(NCCCc1ccccc1)c1nc(-c2cnn3ccccc23)c(Cl)s1] | 397 |

| Name | Example # | Structure | LCMS M + H = |
|---|---|---|---|
| 5-Chloro-N-(3-chlorobenzyl)-4-pyrazolo[1,5-a]pyridin-3-yl-1,3-thiazole-2-carboxamide | 88 | 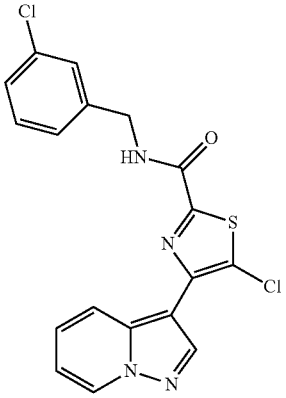 [SMILES: O=C(NCc1cccc(Cl)c1)c1nc(-c2cnn3ccccc23)c(Cl)s1] | 403 |
| 5-Chloro-4-pyrazolo[1,5-a]pyridin-3-yl-N-quinolin-7-yl-1,3-thiazole-2-carboxamide | 89 | 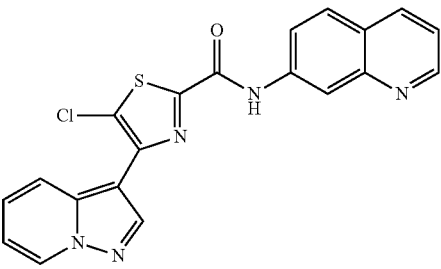 [SMILES: O=C(Nc1ccc2cccnc2c1)c1nc(-c2cnn3ccccc23)c(Cl)s1] | 406 |
| 5-Chloro-4-pyrazolo[1,5-a]pyridin-3-yl-N-[4-(trifluoromethyl)benzyl]-1,3-thiazole-2-carboxamide | 90 | 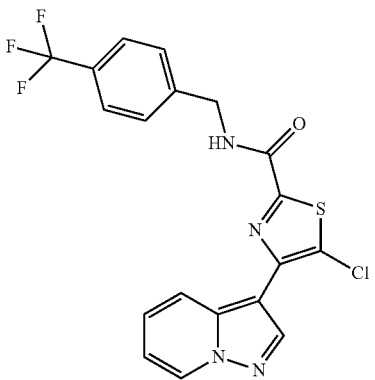 [SMILES: O=C(NCc1ccc(C(F)(F)F)cc1)c1nc(-c2cnn3ccccc23)c(Cl)s1] | 437 |
| 3-{2-[(4-Benzylpiperazin-1-yl)carbonyl]-5-chloro-1,3-thiazol-4-yl}pyrazolo[1,5-a]pyridine | 91 | 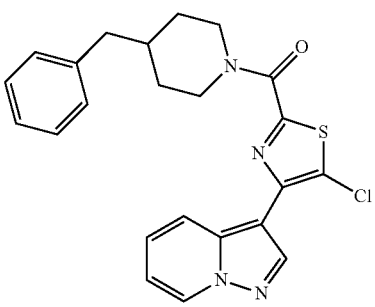 [SMILES: O=C(c1nc(-c2cnn3ccccc23)c(Cl)s1)N1CCC(Cc2ccccc2)CC1] | 437 |

-continued

| Name | Example # | Structure | LCMS M + H = |
|---|---|---|---|
| 3-(5-Chloro-2-{[4-(3-methoxyphenyl)piperazin-1-yl]carbonyl}-1,3-thiazol-4-yl)pyrazolo[1,5-a]pyridine | 92 | 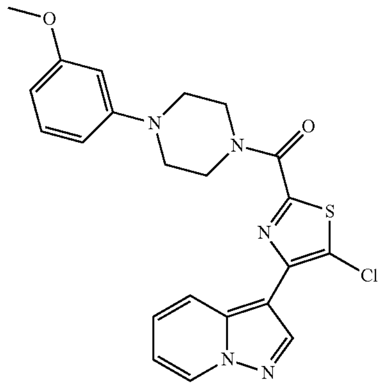 [SMILES: COc1cccc(N2CCN(C(=O)c3nc(-c4cnn5ccccc45)c(Cl)s3)CC2)c1] | 454 |
| 5-Chloro-N-ethyl-N-phenyl-4-pyrazolo[1,5-a]pyridin-3-yl-1,3-thiazole-2-carboxamide | 93 | 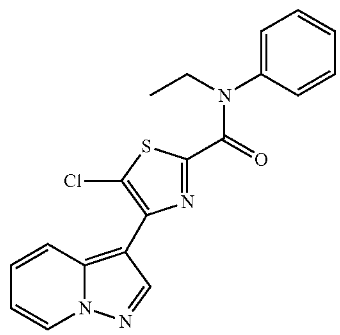 [SMILES: CCN(C(=O)c1nc(-c2cnn3ccccc23)c(Cl)s1)c1ccccc1] | 383 |
| 5-Chloro-N-isopropyl-N-phenyl-4-pyrazolo[1,5-a]pyridin-3-yl-1,3-thiazole-2-carboxamide | 94 | 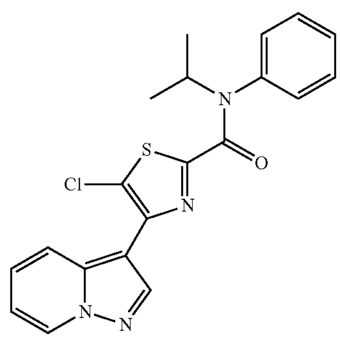 [SMILES: CC(C)N(C(=O)c1nc(-c2cnn3ccccc23)c(Cl)s1)c1ccccc1] | 397 |
| N-(2-Anilinocyclohexyl)-5-chloro-4-pyrazolo[1,5-a]pyridin-3-yl-1,3-thiazole-2-carboxamide | 95 | 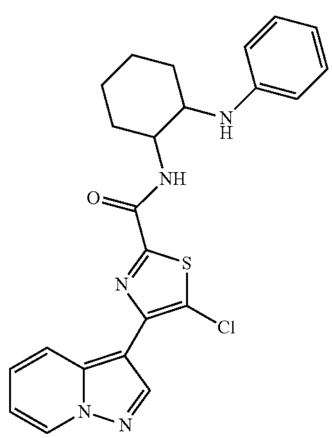 [SMILES: O=C(NC1CCCCC1Nc1ccccc1)c1nc(-c2cnn3ccccc23)c(Cl)s1] | 452 |

-continued

| Name | Example # | Structure | LCMS M + H = |
|---|---|---|---|
| 5-Chloro-N-methyl-N-(3-methylphenyl)-4-pyrazolo[1,5-a]pyridin-3-yl-1,3-thiazole-2-carboxamide | 96 | 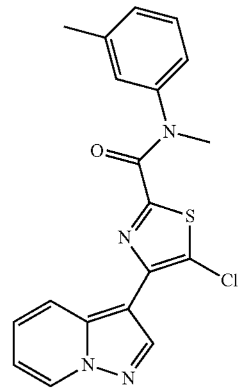 [SMILES: Cc1cccc(N(C)C(=O)c2nc(-c3cnn4ccccc34)c(Cl)s2)c1] | 383 |
| 3-(5-Chloro-2-{[3-(methylsulfonyl)pyrrolidin-1-yl]carbonyl}-1,3-thiazol-4-yl)pyrazolo[1,5-a]pyridine | 97 | 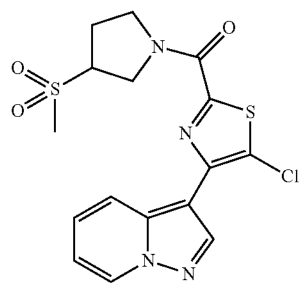 [SMILES: CS(=O)(=O)C1CCN(C(=O)c2nc(-c3cnn4ccccc34)c(Cl)s2)C1] | 411 |
| N-[(1R)-1-(Aminomethyl)-2,2,2-trifluoroethyl]-5-chloro-4-pyrazolo[1,5-a]pyridin-3-yl-1,3-thiazole-2-carboxamide | 98 | 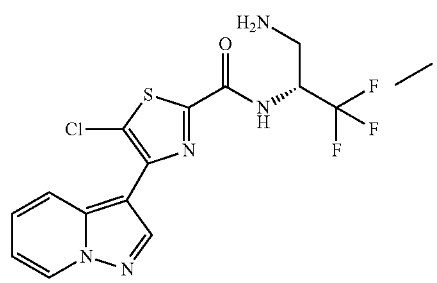 | 390 |
| N-(2-Aminoethoxy)-5-chloro-4-pyrazolo[1,5-a]pyridin-3-yl-1,3-thiazole-2-carboxamide | 99 | 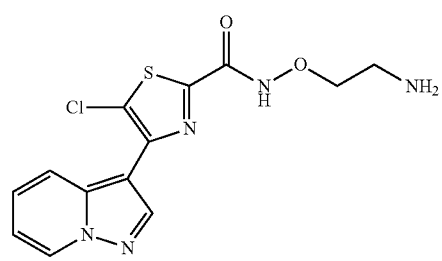 [SMILES: NCCONC(=O)c1nc(-c2cnn3ccccc23)c(Cl)s1] | 338 |
| N-[(1S)-1-(Aminomethyl)-2,2,2-trifluoroethyl]-5-chloro-4-pyrazolo[1,5-a]pyridin-3-yl-1,3-thiazole-2-carboxamide | 100 | 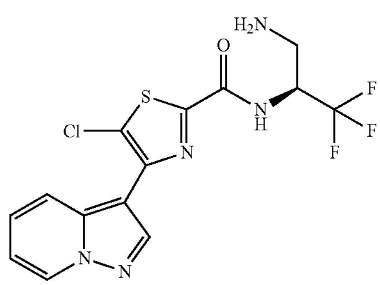 [SMILES: NC[C@H](NC(=O)c1nc(-c2cnn3ccccc23)c(Cl)s1)C(F)(F)F] | 390 |

-continued
| Name | Example # | Structure | LCMS M + H = |
|---|---|---|---|
| 5-Chloro-N-(2-hydroxyethoxy)-4-pyrazolo[1,5-a]pyridin-3-yl-1,3-thiazole-2-carboxamide | 101 | 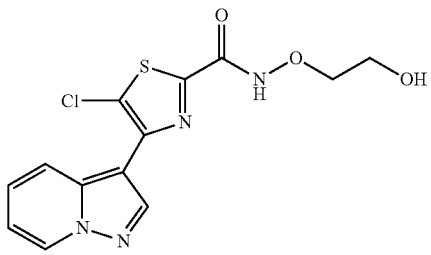 [SMILES: O=C(NOCCO)c1nc(-c2cnn3ccccc23)c(Cl)s1] | 339 |
| N-(2-Anilinocyclohexyl)-5-chloro-4-pyrazolo[1,5-a]pyridin-3-yl-1,3-thiazole-2-carboxamide | 102 | 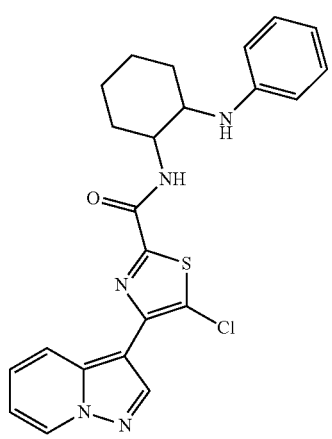 [SMILES: O=C(NC1CCCCC1Nc1ccccc1)c1nc(-c2cnn3ccccc23)c(Cl)s1] | 452 |
| 5-Chloro-N-(2,4-difluorophenyl)-N-methyl-4-pyrazolo[1,5-a]pyridin-3-yl-1,3-thiazole-2-carboxamide | 103 | 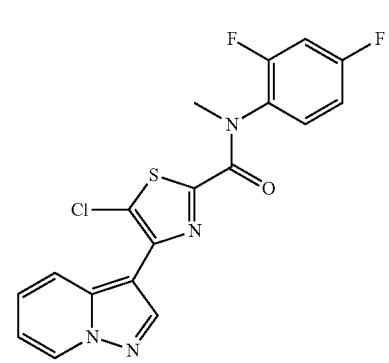 [SMILES: CN(C(=O)c1nc(-c2cnn3ccccc23)c(Cl)s1)c1ccc(F)cc1F] | 405 |
| 5-Chloro-N-(2,5-difluorophenyl)-N-methyl-4-pyrazolo[1,5-a]pyridin-3-yl-1,3-thiazole-2-carboxamide | 104 | 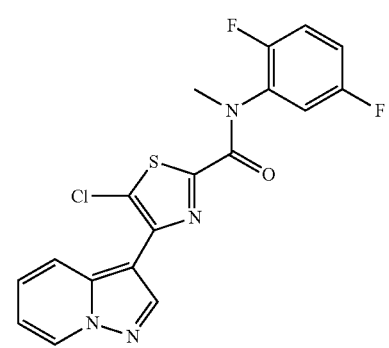 [SMILES: CN(C(=O)c1nc(-c2cnn3ccccc23)c(Cl)s1)c1cc(F)ccc1F] | 405 |

-continued

| Name | Example # | Structure | LCMS M + H = |
|---|---|---|---|
| 5-Chloro-N-(2,3-difluorophenyl)-N-methyl-4-pyrazolo[1,5-a]pyridin-3-yl-1,3-thiazole-2-carboxamide | 105 | 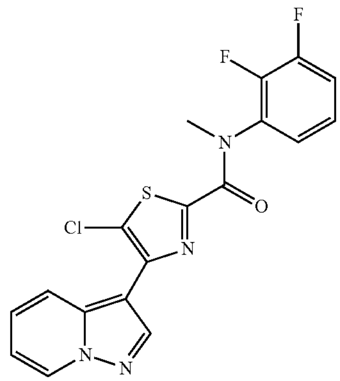 [SMILES: CN(C(=O)c1nc(-c2cnn3ccccc23)c(Cl)s1)c1cccc(F)c1F] | 405 |
| 5-Chloro-N-(4-chlorophenyl)-N-methyl-4-pyrazolo[1,5-a]pyridin-3-yl-1,3-thiazole-2-carboxamide | 106 | 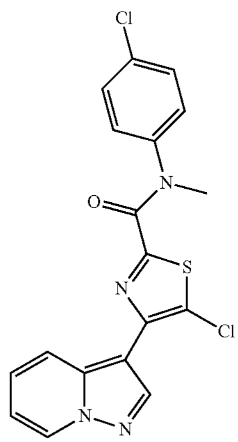 [SMILES: CN(C(=O)c1nc(-c2cnn3ccccc23)c(Cl)s1)c1ccc(Cl)cc1] | 403 |
| N-(3-Aminophenyl)-5-chloro-N-methyl-4-pyrazolo[1,5-a]pyridin-3-yl-1,3-thiazole-2-carboxamide | 107 | 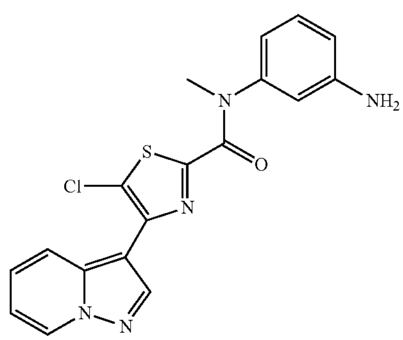 [SMILES: CN(C(=O)c1nc(-c2cnn3ccccc23)c(Cl)s1)c1cccc(N)c1] | 384 |
| 5-Chloro-N-methyl-N-(4-methylphenyl)-4-pyrazolo[1,5-a]pyridin-3-yl-1,3-thiazole-2-carboxamide | 108 | 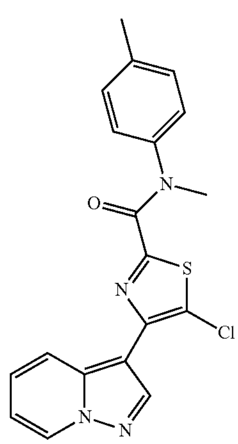 [SMILES: Cc1ccc(N(C)C(=O)c2nc(-c3cnn4ccccc34)c(Cl)s2)cc1] | 383 |

| Name | Example # | Structure | LCMS M + H = |
|---|---|---|---|
| 5-Chloro-N-methyl-4-pyrazolo[1,5-a]pyridin-3-yl-N-pyridin-2-yl-1,3-thiazole-2-carboxamide | 109 | 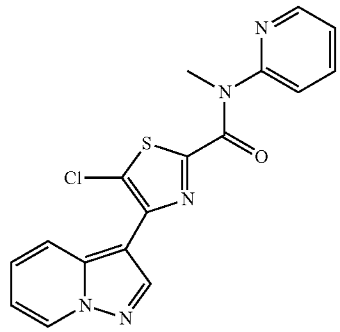 [SMILES: CN(C(=O)c1nc(-c2cnn3ccccc23)c(Cl)s1)c1ccccn1] | 370 |
| 5-Chloro-N-(2,6-difluorophenyl)-N-methyl-4-pyrazolo[1,5-a]pyridin-3-yl-1,3-thiazole-2-carboxamide | 110 | 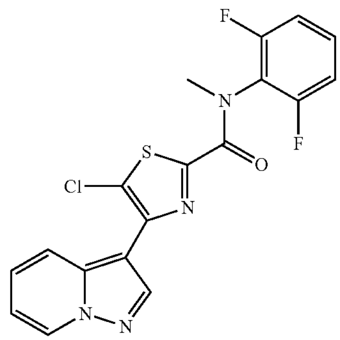 [SMILES: CN(C(=O)c1nc(-c2cnn3ccccc23)c(Cl)s1)c1c(F)cccc1F] | 405 |
| 5-Chloro-N-methyl-N-(3-methylphenyl)-4-pyrazolo[1,5-a]pyridin-3-yl-1,3-thiazole-2-carboxamide | 111 | 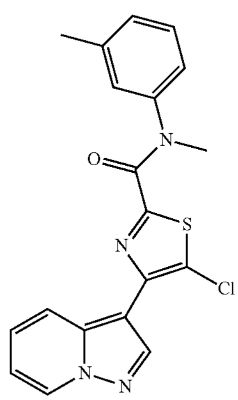 [SMILES: Cc1cccc(N(C)C(=O)c2nc(-c3cnn4ccccc34)c(Cl)s2)c1] | 383 |
| 5-Chloro-4-pyrazolo[1,5-a]pyridin-3-yl-N-(2,2,2-trifluoroethyl)-1,3-thiazole-2-carboxamide | 112 | 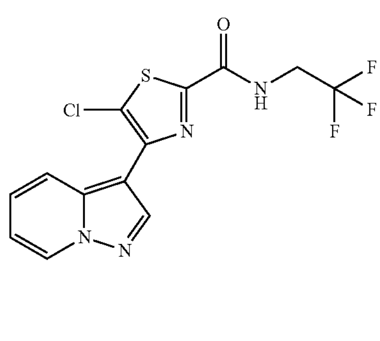 [SMILES: O=C(NCC(F)(F)F)c1nc(-c2cnn3ccccc23)c(Cl)s1] | 361 |

-continued

| Name | Example # | Structure | LCMS M + H = |
|---|---|---|---|
| 5-Chloro-N-(3-hydroxyphenyl)-N-methyl-4-pyrazolo[1,5-a]pyridin-3-yl-1,3-thiazole-2-carboxamide | 113 | 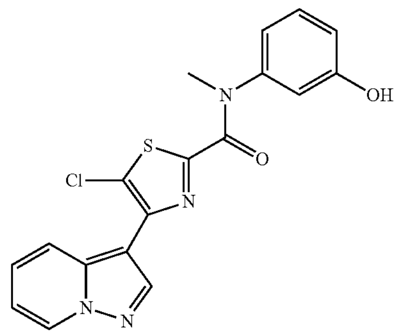 [SMILES: CN(C(=O)c1nc(-c2cnn3ccccc23)c(Cl)s1)c1cccc(O)c1] | 385 |
| N-[(1R,6R)-2-Aminocyclohexyl]-5-chloro-4-[(6-trifluoromethyl)pyrazolo[1,5-a]pyridin-3-yl]-1,3-thiazole-2-carboxamide | 114 | 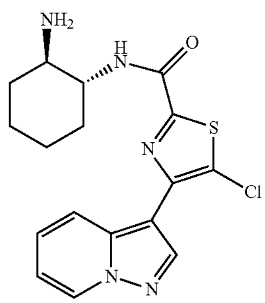 [SMILES: N[C@@H]1CCCC[C@H]1NC(=O)c1nc(-c2cnn3ccccc23)c(Cl)s1] | 376 |
| 5-Chloro-N-(2-chlorophenyl)-N-methyl-4-pyrazolo[1,5-a]pyridin-3-yl-1,3-thiazole-2-carboxamide | 115 | 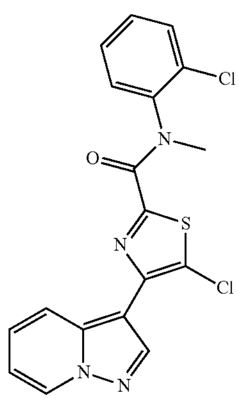 [SMILES: CN(C(=O)c1nc(-c2cnn3ccccc23)c(Cl)s1)c1ccccc1Cl] | 403 |
| 5-Chloro-N-methyl-N-(2-methylphenyl)-4-pyrazolo[1,5-a]pyridin-3-yl-1,3-thiazole-2-carboxamide | 116 | 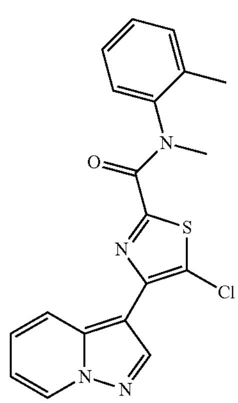 [SMILES: Cc1ccccc1N(C)C(=O)c1nc(-c2cnn3ccccc23)c(Cl)s1] | 383 |

| Name | Example # | Structure | LCMS M + H = |
|---|---|---|---|
| 5-Chloro-N-(4-fluorophenyl)-N-methyl-4-pyrazolo[1,5-a]pyridin-3-yl-1,3-thiazole-2-carboxamide | 117 | 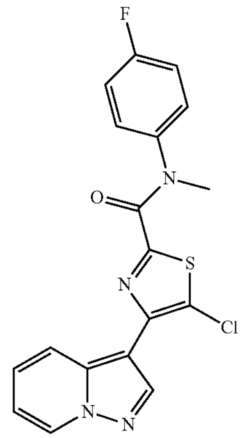 [SMILES: CN(C(=O)c1nc(-c2cnn3ccccc23)c(Cl)s1)c1ccc(F)cc1] | 387 |
| 5-Chloro-N-(3-chlorophenyl)-N-methyl-4-pyrazolo[1,5-a]pyridin-3-yl-1,3-thiazole-2-carboxamide | 118 | 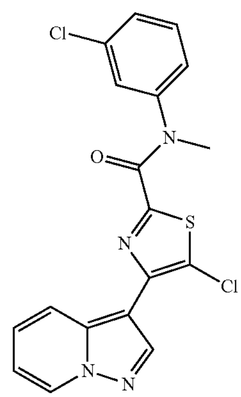 [SMILES: CN(C(=O)c1nc(-c2cnn3ccccc23)c(Cl)s1)c1cccc(Cl)c1] | 403 |
| 5-Chloro-N-(3-fluorophenyl)-N-methyl-4-pyrazolo[1,5-a]pyridin-3-yl-1,3-thiazole-2-carboxamide | 119 | 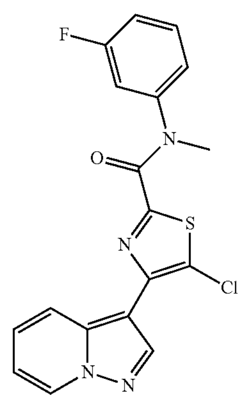 [SMILES: CN(C(=O)c1nc(-c2cnn3ccccc23)c(Cl)s1)c1cccc(F)c1] | 387 |
| N-[(1S,6S)-2-Aminocyclohexyl]-5-chloro-4-[(6-trifluoromethyl)pyrazolo[1,5-a]pyridin-3-yl]-1,3-thiazole-2-carboxamide | 120 | 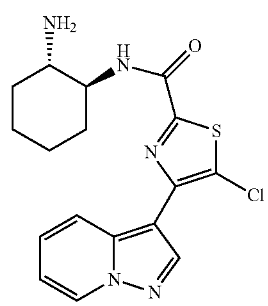 [SMILES: N[C@H]1CCCC[C@@H]1NC(=O)c1nc(-c2cnn3ccccc23)c(Cl)s1] | 376 |

-continued

| Name | Example # | Structure | LCMS M + H = |
|---|---|---|---|
| 5-Chloro-N-(2-chlorophenyl)-N-methyl-4-pyrazolo[1,5-a]pyridin-3-yl-1,3-thiazole-2-carboxamide | 121 | 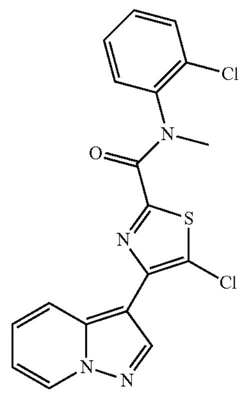 [SMILES: CN(C(=O)c1nc(-c2cnn3ccccc23)c(Cl)s1)c1ccccc1Cl] | 403 |
| {4-[(5-Chloro-4-pyrazolo[1,5-a]pyridin-3-yl-1,3-thiazol-2-yl)carbonyl]morpholin-2-yl}methanol | 122 | 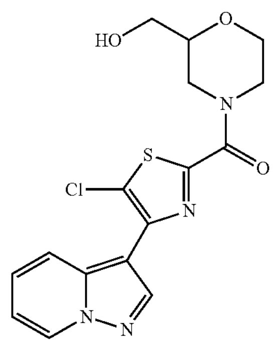 [SMILES: O=C(c1nc(-c2cnn3ccccc23)c(Cl)s1)N1CCOC(CO)C1] | 379 |
| 1-[(5-Chloro-4-pyrazolo[1,5-a]pyridin-3-yl-1,3-thiazol-2-yl)carbonyl]-2,3,4,5-tetrahydro-1H-1,4-benzodiazepine | 123 | 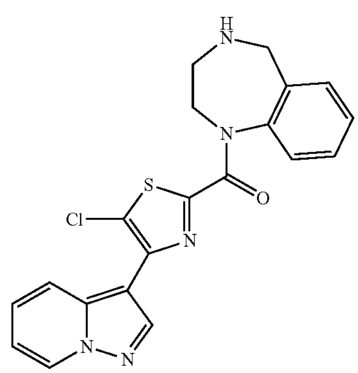 [SMILES: O=C(c1nc(-c2cnn3ccccc23)c(Cl)s1)N1CCNCc2ccccc21] | 410 |
| 5-Chloro-N-(3-fluorophenyl)-N-methyl-4-pyrazolo[1,5-a]pyridin-3-yl-1,3-thiazole-2-carboxamide | 124 | 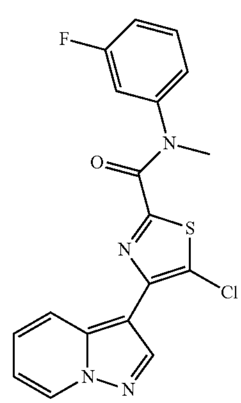 [SMILES: CN(C(=O)c1nc(-c2cnn3ccccc23)c(Cl)s1)c1cccc(F)c1] | 387 |

| Name | Example # | Structure | LCMS M + H = |
| --- | --- | --- | --- |
| N-[1-(Aminomethyl)-6-fluoro-2,3-dihydro-1H-inden-1-yl]-5-chloro-4-pyrazolo[1,5-a]pyridin-3-yl-1,3-thiazole-2-carboxamide | 125 | 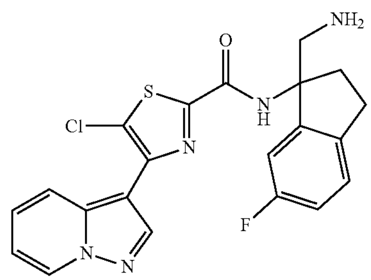 [SMILES: NCC1(NC(=O)c2nc(-c3cnn4ccccc34)c(Cl)s2)CCc2ccc(F)cc21] | 442 |
| 5-Chloro-N-methyl-N-phenyl-4-pyrazolo[1,5-a]pyridin-3-yl-1,3-thiazole-2-carboxamide | 126 | 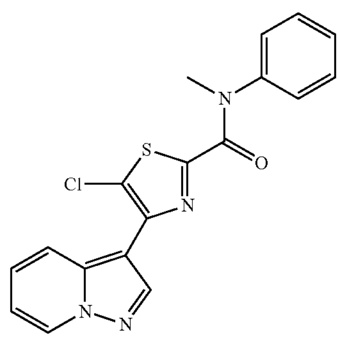 [SMILES: CN(C(=O)c1nc(-c2cnn3ccccc23)c(Cl)s1)c1ccccc1] | 369 |
| N-[(1R,6S)-6-amino-2,2-difluorocyclohexyl]-4-pyrazolo[1,5-a]pyridin-3-yl-1,3-thiazole-2-carboxamide | 127 | 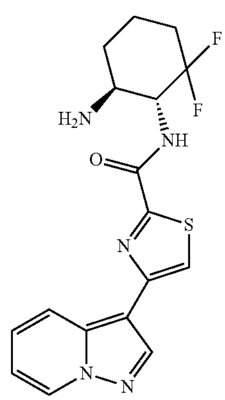 [SMILES: N[C@H]1CCCC(F)(F)[C@@H]1NC(=O)c1nc(-c2cnn3ccccc23)cs1] | 378 |
| 3-[2-(Piperidin-1-ylcarbonyl)-1,3-thiazol-4-yl]pyrazolo[1,5-a]pyridine | 128 | 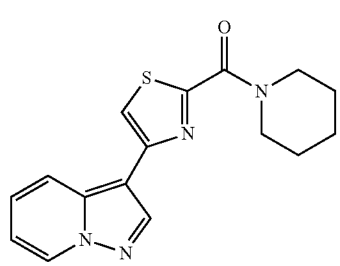 [SMILES: O=C(c1nc(-c2cnn3ccccc23)cs1)N1CCCCC1] | 313 |
| N-[1-(Aminomethyl)-5-fluoro-2,3-dihydro-1H-inden-1-yl]-5-chloro-4-pyrazolo[1,5-a]pyridin-3-yl-1,3-thiazole-2-carboxamide | 129 | 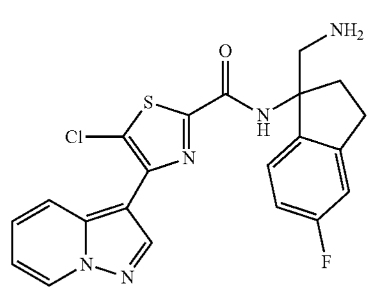 [SMILES: NCC1(NC(=O)c2nc(-c3cnn4ccccc34)c(Cl)s2)CCc2cc(F)ccc21] | 442 |

-continued

| Name | Example # | Structure | LCMS M + H = |
|---|---|---|---|
| N-[1-(Aminomethyl)-4-fluoro-2,3-dihydro-1H-inden-1-yl]-5-chloro-4-pyrazolo[1,5-a]pyridin-3-yl-1,3-thiazole-2-carboxamide | 130 | 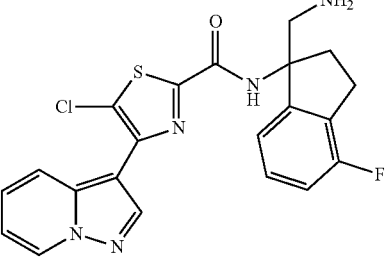 | 442 |
| N-[1-(Aminomethyl)-2,3-dihydro-1H-inden-1-yl]-5-chloro-4-pyrazolo[1,5-a]pyridin-3-yl-1,3-thiazole-2-carboxamide | 131 | 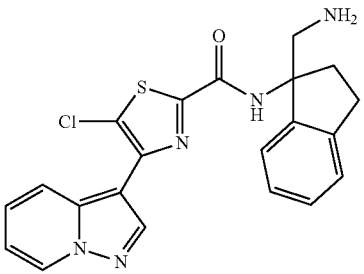 [SMILES: NCC1(NC(=O)c2nc(-c3cnn4ccccc34)c(Cl)s2)CCc2ccccc21] | 424 |
| N-(2-Amino-3,3,3-trifluoro-1-phenylpropyl)-5-chloro-4-pyrazolo[1,5-a]pyridin-3-yl-1,3-thiazole-2-carboxamide | 132 | 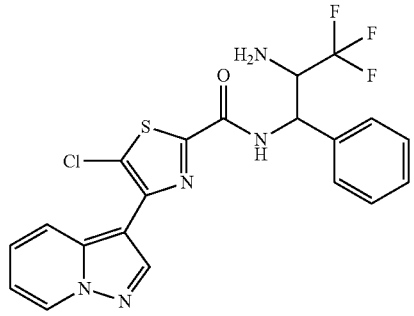 [SMILES: NC(C(NC(=O)c1nc(-c2cnn3ccccc23)c(Cl)s1)c1ccccc1)C(F)(F)F] | 466 |
| N-(2-Amino-3,3,3-trifluoro-1-phenylpropyl)-5-chloro-4-pyrazolo[1,5-a]pyridin-3-yl-1,3-thiazole-2-carboxamide | 133 | 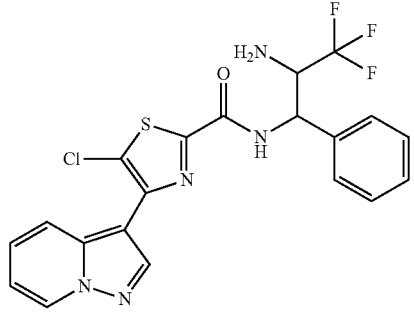 [SMILES: NC(C(NC(=O)c1nc(-c2cnn3ccccc23)c(Cl)s1)c1ccccc1)C(F)(F)F] | 466 |
| N-[(1S)-1-(Aminomethyl)-2,2,2-trifluoro-1-methylethyl]-5-chloro-4-pyrazolo[1,5-a]pyridin-3-yl-1,3-thiazole-2-carboxamide | 134 | 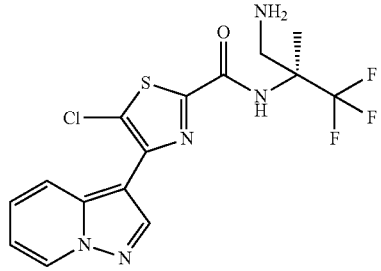 [SMILES: C[C@@](CN)(NC(=O)c1nc(-c2cnn3ccccc23)c(Cl)s1)C(F)(F)F] | 404 |

| Name | Example # | Structure | LCMS M + H = |
|---|---|---|---|
| 5-Chloro-N-(2-fluorophenyl)-N-methyl-4-pyrazolo[1,5-a]pyridin-3-yl-1,3-thiazole-2-carboxamide | 135 | 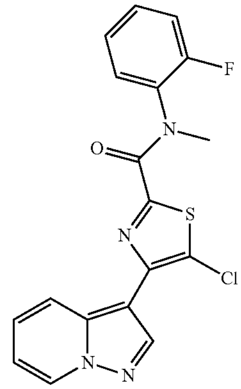 [SMILES: CN(C(=O)c1nc(-c2cnn3ccccc23)c(Cl)s1)c1ccccc1F] | 387 |

Example 136

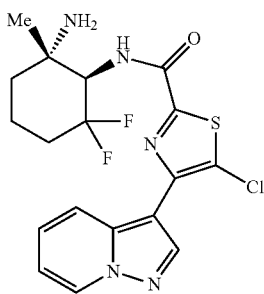

N-[(1R,2S)-2-amino-6,6-difluoro-2-methylcyclohexyl]-5-chloro-4-(pyrazolo[1,5-a]pyridin-3-yl)-1,3-thiazole-2-carboxamide (Scheme 14)

Step A: Epoxidation

A solution of 3-methylcyclohex-2-en-1-one (63, 25.7 mL, 227 mmol) and hydrogen peroxide (69.5 mL, 681 mmol) in methanol (200 mL) was cooled to 15° C. Aqueous sodium hydroxide (2M, 56.7 mL, 113 mmol) was added dropwise with stirring over the course of one hour. The reaction was stirred for 3 hours and was then poured into 400 mL water. Ether (2×300 mL) was used to extract the product and the combined organics were washed first with aqueous sodium thiosulfate (4×100 mL) and then followed by brine (300 mL). The organic was dried magnesium sulfate and was concentrated under reduced pressure to yield a crude yellow oil (~40 mL). Compound 64 was purified by distillation to obtain a clear oil (10.6 g, 83 mmol, 37% yield). $^1$H NMR (500 MHz, CDCl$_3$) δ 3.06 (s, 1H), 2.52-2.41 (m, 1H), 2.17-2.08 (m, 1H), 2.08-1.78 (m, 3H), 1.68-1.57 (m, 1H), 1.44 (s, 3H).

Step B: Fluorination

To a solution of epoxide 64 (10.6 g, 84 mmol) in DCM (100 mL) was added deoxofluor (41.7 mL, 226 mmol). The reaction was stirred for 8 hours at ambient temperature and was then poured into ~200 g ice. The extracted organic was washed water (100 mL) and brine (100 mL) before drying over magnesium sulfate and concentrating. The resultant oil was purified by column chromatography (silica gel, 5% ether in hexanes, linear gradient) to yield compound 65 (7.92 g, 53.5 mmol, 64% yield). Note:  product is volatile  $^1$H NMR (500 MHz, CDCl$_3$) δ 3.09 (d, J=4.2, 1H), 2.02-1.87 (m, 2H), 1.78-1.61 (m, 2H), 1.60-1.50 (m, 2H), 1.40 (s, 3H). $^{19}$F NMR (470 MHz, CDCl$_3$) δ −95.22--100.83 (m, 2F).

Step C: Epoxide Opening

For a related literature procedure, see: Overman, L. E.; Sugai, S. *J. Org. Chem.* 1985, 50, 4154-4155. To a rapidly stirring solution of (R)-α-methylbenzylamine (6.61 g, 54.6 mmol) in DCM (60 mL) at 0° C. was added trimethylaluminum (27.3 mL, 54.6 mmol) was added dropwise. After stirring for 1 hr at 0° C. a solution of compound 65 (7.7 g, 52.0 mmol) in DCM (40 mL) was added dropwise to the solution. The reaction was aged an additional 3 hrs at 0° C. before warming to room temperature overnight. The reaction was then cooled to −20° C. and was poured into 1000 mL Erlenmyer flask equipped with stir bar and sodium fluoride (10.9 g, 260 mmol). Ice (5.90 g, 327 mmol) was added slowly and was vigorously stirred for ca. 1 hour before filtering the solution through celite (wash with ~500 mL DCM). The solution was concentrated under reduced pressure and was purified by column chromatography (silica gel, 10-100% ethyl acetate in hexanes, linear gradient) to yield a mixture of diastereomeric products.

The diasteromers were purified by preparative chromatography (chiralcel OJ column) to yield (1R,6S)-2,2-difluoro-6-methyl-6-{[(1R)-1-phenylethyl]amino}cyclohexanol (435 mg, 1.68 mmol, 3.2% yield) and (1S,6R)-2,2-difluoro-6-methyl-6-{[(1R)-1-phenylethyl]amino}cyclohexanol (compound 66, 608 mg, 2.26 mmol, 4.3% yield). $^1$H NMR (600 MHz, cdcl3) δ 7.36 (d, J=7.3, 2H), 7.29 (t, J=7.6, 2H), 7.20 (t, J=7.3, 1H), 4.01 (q, J=6.7, 1H), 3.62-3.45 (m, 1H), 2.03 (d, J=9.0, 2H), 1.66-1.27 (m, 10H), 1.14 (d, J=1.9, 4H). $^{19}$F NMR (470 MHz, cdcl3) 6-99.01 (dd, J=241.2, 21.4, 1F), −112.75 (s, 1F).

Step D: Hydrogenation

To a degassed solution of compound 66 (608 mg, 2.26 mmol) in MeOH was added Pd/C (240 mg, 2.26 mmol). The reaction was stirred overnight at room temperature under hydrogen atmosphere (1 atm). Upon completion the solution was filtered through florosil and was concentrated to dryness. The crude material was carried forward without further purification (compound 67, 255 mg, 1.5 mmol, 68% yield). NMR (500 MHz, CDCl$_3$) δ 3.50 (d, J=16.7, 1H), 2.24-1.98 (m, 1H), 1.74 (s, 7H), 1.39 (s, 1H), 1.16 (s, 2H). $^{19}$F NMR (470 MHz, CDCl$_3$) δ −100.81 (d, J=245.7, 1F)

Step E: Amine Protection

To a solution of compound 67 (255 mg, 1.54 mmol) in DCM (1 mL) was added TEA (430 μL, 3.09 mmol) followed by BOC$_2$O (394 μL, 1.698 mmol). The reaction was stirred for 10 hours at room temperature and was evaporated in vacuo. The resultant residue was directly purified by flash column chromatography (silica gel, 0-30% ethyl acetate in hexanes, linear gradient) to give 290 mg (71% yield) of compound 68: $^1$H NMR (500 MHz, CDCl$_3$) δ 4.68 (s, 1H), 4.19 (dd, J=18.2, 5.9, 1H), 3.50 (s, 2H), 2.11 (s, 1H), 1.90 (dd, J=17.2, 7.2, 1H), 1.81-1.52 (m, 5H), 1.44 (s, 10H), 1.33 (d, J=22.3, 3H), $^{19}$F NMR (470 MHz, CDCl$_3$) δ −100.97 (d, J=246.2, 1F), −110.21--116.47 (broad s, 1F).

Step F: Triflate Formation

Compound 68 (290 mg, 1.09 mmol) was dissolved in pyridine (2 mL) and dichloromethane (8 mL) before being cooled to 0° C. Triflic anhydride (0.37 mL, 2.186 mmol) was added dropwise to the solution and the solution was stirred for 1 hr. The reaction was partitioned between water (100 mL) and ethyl acetate (50 mL), the organic was washed with brine (50 mL), dried over sodium sulfate, filtered and evaporated in vacuo. Purification by flash chromatography (silica gel, 0-10% ethyl acetate in hexanes, linear gradient) gave 356 mg (82%) compound 69: $^1$H NMR (500 MHz, CDCl$_3$) δ 5.90 (s, 1H), 4.57 (s, 1H), 2.79 (s, 1H), 2.27-2.15 (m, 1H), 1.97-1.80 (m, 1H), 1.74 (s, 1H), 1.69-1.51 (m, 3H), 1.45 (s, 8H), 1.29 (s, 3H).

Step G: Azide Displacement

A solution of 269 (356 mg, 0.896 mmol) and sodium azide (291 mg, 4.48 mmol) in DMF (4 mL) was sealed and heated to 100° C. for 4 hours in a microwave reactor. The reaction was directly purified by flash chromatography (silica gel, 0-50% ethyl acetate in hexanes, linear gradient) to yield the major product (1R,2R)-2-azido-3,3-difluoro-1-methylcyclohexanamine (71, 150 mg, 0.79 mmol, 88% yield) and a minor product tert-butyl [(1R,2S)-2-azido-6,6-difluoro-2-methylcyclohexyl]carbamate (70, 30 mg, 0.10 mmol, 11% yield). Compound 70: $^1$H NMR (500 MHz, CDCl$_3$) δ 4.90-4.76 (m, 1H), 4.15-3.97 (m, 1H), 2.28-2.12 (m, 1H), 1.82 (d, J=24.1, 3H), 1.59 (d, i=31.4, 4H), 1.49 (s, 9H), 1.34 (s, 3H). Compound 71: $^1$H NMR (500 MHz, CDCl$_3$) δ 5.31 (s, 1H), 4.21 (t, J=6.3, 1H), 2.18-1.98 (m, 2H), 1.78 (d, J=10.7, 2H), 1.67 (d, J=12.9, 3H), 1.44 (s, 3H).

Step H: Amine Deprotection

Compound 70 (30 mg, 0.103 mmol) was dissolved in DCM (1 mL) and TFA (7.96 μL, 0.103 mmol) was added dropwise at room temperature. The reaction was stirred until complete by LCMS analysis. The reaction was concentrated in vacuo to yield the TFA salt of compound 72 (27 mg, 86% yield). $^1$H NMR (500 MHz, CDCl$_3$) δ 3.65 (t, J=6.6, 1H), 1.60-1.49 (m, 2H), 1.45-1.33 (m, 1H), 0.93 (dd, J=10.0, 4.7, 2H). $^{19}$F NMR (470 MHz, CDCl$_3$) δ −76.28 (s, 0H), −101.69 (d, J=237.3, 1H), −118.96 (d, J=245.5, 1H).

Step 1: Amide Coupling and Reduction

Carboxylic acid 73 (29.4 mg, 0.097 mmol), which was synthesized according to example 2, and by following the procedure outlined in example 1, part C, step 2 and subsequent steps though step E, part 1. The thiazole 5-position was chlorinated with NCS in part D, step 3. Acid 73 was added to a solution of compound 72 (27 mg, 0.097 mmol) in DMF (0.5 mL) was added DIEA (16.86 μL, 0.097 mmol) and BOP (53.4 mg, 0.121 mmol) at room temperature. The reaction was directly purified by prep HPLC (10-100% acetonitrile in water+0.01% TFA modifier) to yield the corresponding amide (20 mg, 46% yield). MS APCI: [M+H]$^+$ m/z 452.0.

To a solution of the amide (20 mg, 0.04 mmol) in THF (0.25 mL) was added resin-bound triphenylphosphine (11.33 mg, 0.089 mmol). The reaction was heated for 72 hours at 105° C. The resin was filtered off and the filtrate was concentrated to dryness and was purified by prep HPLC (10-100% acetonitrile in water+0.01% TFA modifier) and by column chromatography (0-15% methanol in dichloromethane+1% NH$_3$) to yield the title compound (2.4 mg, 5.64 mmol, 13% yield). MS APCI: [M+H]$^+$ 426.0. $^{19}$F NMR (500 MHz, CD$_3$OD) δ 8.65 (d, J=7.3, 2H), 8.56-8.46 (m, 1H), 8.27 (d, J=9.2, 1H), 7.52-7.35 (m, 1H), 7.05 (s, 1H), 4.78-4.58 (m, 1H), 2.41-2.26 (m, 1H), 2.03 (s, 2H), 1.95 (s, 2H), 1.84-1.69 (m, 1H), 1.46 (s, 2H). $^{19}$F NMR (470 MHz, CD$_3$OD) δ −77.66 (s, 3F), −97.32 (d, J=247.6, 1F), −110.33 (d, J=295.0, 1F).

Example 137

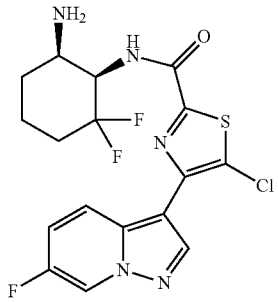 [SMILES: N[C@@H]1CCCC(F)(F)[C@@H]1NC(=O)c1nc(-c2cnn3cc(F)ccc23)c(Cl)s1]

N-[(1R,6R)-6-amino-2,2-difluorocyclohexyl]-5-chloro-4-fluoropyrazolo{1,5-dipyridine-3-yl-1,3-thiazole-2-carboxamide (Scheme 1)

Synthesis began in an analogous fashion to example 1, step A, part 1. Variable functionality on the core pyridine ring was introduced via the use of an appropriately functionalized pyridine in step A, part 2, which in this case was 3-fluoropyridine. The synthesis continued with the use of step C (such that step B was not carried out) with all subsequent steps leading to the synthesis of final compound. MS APCI: [M+H]$^+$ m/z 430.0. $^1$H NMR (500 MHz, DMSO-d$_6$): δ 8.65 (1H, s), 8.47 (1H, s), 8.30-8.25 (1H, m), 8.22-8.17 (1H, m), 4.44-4.33 (1H, m), 3.38 (1H, br s), 2.24-2.20 (1H, m), 2.05-1.95 (1H, m), 1.91-1.82 (2H, m), 1.80-1.70 (2H, m).

The following examples were prepared in an analogous manner of that described in example 137 with the use of known or commercial amines in step E, part 3. Variation at the thiazole 5-position was introduced in example 1, part D, step 3 by the use of NCS or NBS or NIS to add a chloride or bromide or iodide, respectively. Note: In cases where 5-position is unfunctionalized, the halogenation step was not carried out.

| Name | Example # | Structure | LCMS M + H = |
|---|---|---|---|
| N-[(1R,6S)-6-Amino-2,2-difluorocyclohexyl]-5-chloro-4-(6-fluoropyrazolo[1,5-a]pyridine-3-yl-1,3-thiazole-2-carboxamide | 138 | 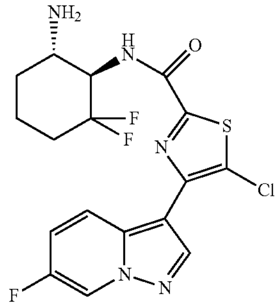 [SMILES: N[C@H]1CCCC(F)(F)[C@@H]1NC(=O)c1nc(-c2cnn3cc(F)ccc23)c(Cl)s1] | 430 |
| 5-Chloro-N-[(1R,6S)-2,2-difluoro-6-hydroxycyclohexyl]-4-(pyrazolo[1,5-a]pyridine-3-yl-1,3-thiazole-2-carboxamide | 139 | 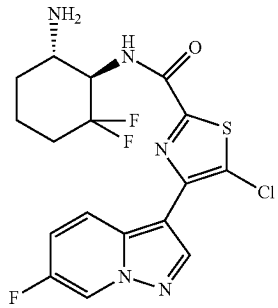 [SMILES: N[C@H]1CCCC(F)(F)[C@@H]1NC(=O)c1nc(-c2cnn3cc(F)ccc23)c(Cl)s1] | 413 |
| N-[(1R,6S)-6-Amino-2,2-difluorocyclohexyl]-5-chloro-4-(6-iodopyrazolo[1,5-a]pyridin-3-yl)-1,3-thiazole-2-carboxamide | 140 | 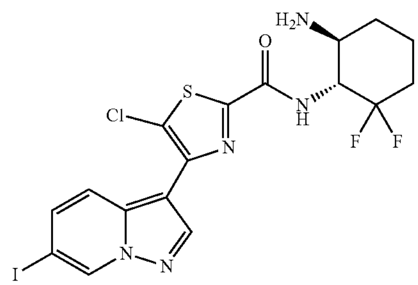 [SMILES: N[C@H]1CCCC(F)(F)[C@@H]1NC(=O)c1nc(-c2cnn3cc(I)ccc23)c(Cl)s1] | 538 |
| N-[(1R,6S)-6-Amino-2,2-difluorocyclohexyl]-4-(6-bromopyrazolo[1,5-a]pyridin-3-yl)-5-chloro-1,3-thiazole-2-carboxamide | 141 | 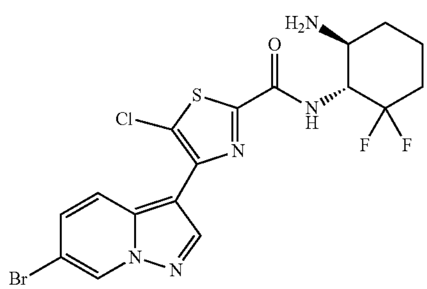 [SMILES: N[C@H]1CCCC(F)(F)[C@@H]1NC(=O)c1nc(-c2cnn3cc(Br)ccc23)c(Cl)s1] | 490 |
| N-[(1R,6S)-6-Amino-2,2-difluorocyclohexyl]-5-chloro-4-[5-(trifluoromethyl)pyrazolo[1,5-a]pyridin-3-yl]-1,3-thiazole-2-carboxamide | 142 | 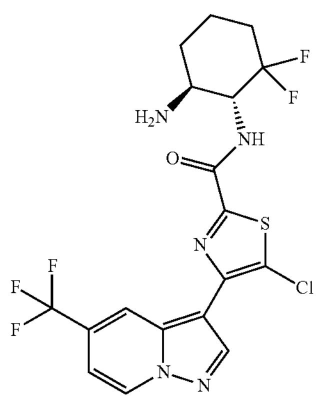 [SMILES: N[C@H]1CCCC(F)(F)[C@@H]1NC(=O)c1nc(-c2cnn3ccc(C(F)(F)F)cc23)c(Cl)s1] | 480 |

| Name | Example # | Structure | LCMS M + H = |
|---|---|---|---|
| N-[(1R-6S)-6-Amino-2,2-difluorocyclohexyl]-5-chloro-4-[(6-trifluoromethyl)pyrazolo[1,5-a]pyridin-3-yl]-1,3-thiazole-2-carboxamide | 143 | 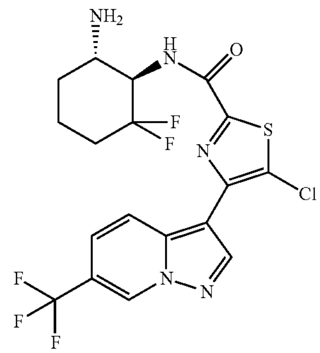 [SMILES: N[C@H]1CCCC(F)(F)[C@@H]1NC(=O)c1nc(-c2cnn3cc(C(F)(F)F)ccc23)c(Cl)s1] | 480 |
| N-[(1R,6S)-6-Amino-2,2-difluorocyclohexyl]-5-chloro-4-(6-methoxypyrazolo[1,5-a]pyridin-3-yl)-1,3-thiazole-2-carboxamide | 144 | 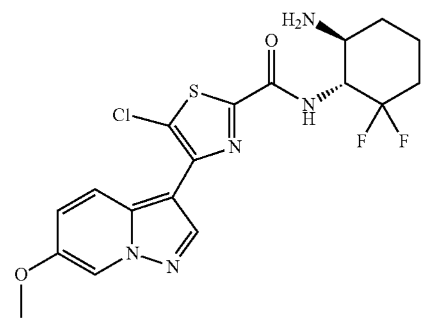 [SMILES: COc1ccc2c(-c3nc(C(=O)N[C@@H]4[C@@H](N)CCCC4(F)F)sc3Cl)cnn2c1] | 442 |
| N-[(1R,6S)-6-Amino-2,2-difluorocyclohexyl]-5-chloro-4-(6-ethylpyrazolo[1,5-a]pyridin-3-yl)-1,3-thiazole-2-carboxamide | 145 | 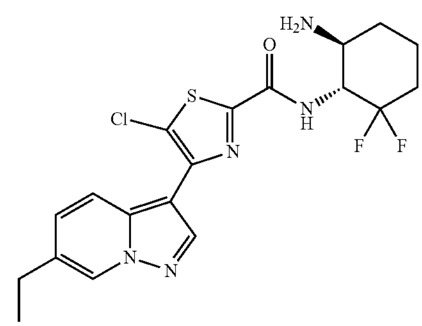 [SMILES: CCc1ccc2c(-c3nc(C(=O)N[C@@H]4[C@@H](N)CCCC4(F)F)sc3Cl)cnn2c1] | 440 |
| N-[(1R,6S)-6-Amino-2,2-difluorocyclohexyl]-5-chloro-4-(5-cyanopyrazolo[1,5-a]pyridin-3-yl)-1,3-thiazole-2-carboxamide | 146 | 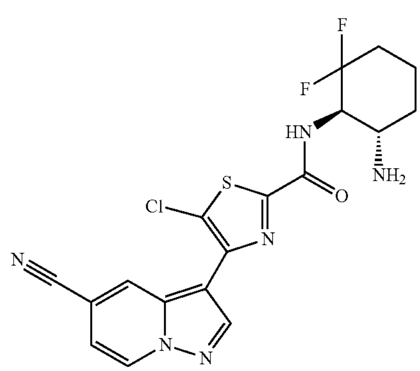 [SMILES: N#Cc1ccn2ncc(-c3nc(C(=O)N[C@@H]4[C@@H](N)CCCC4(F)F)sc3Cl)c2c1] | 437 |

-continued

| Name | Example # | Structure | LCMS M + H = |
|---|---|---|---|
| 3-[2-({[(1R,6S)-6-Amino-2,2-difluorocyclohexyl]amino}-carbonyl)-5-chloro-1,3-thiazol-4-yl]pyrazolo[1,5-a]pyridine-5-carboxamide | 147 | 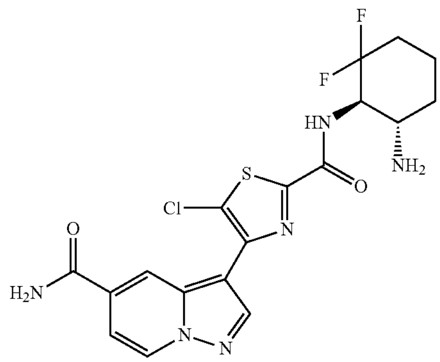 [SMILES: NC(=O)c1ccn2ncc(-c3nc(C(=O)N[C@@H]4[C@@H](N)CCCC4(F)F)sc3Cl)c2c1] | 455 |
| N-[(1R,6S)-6-amino-2,2-difluorocyclohexyl]-5-chloro-4-(6-fluoropyrazolo[1,5-a]pyridin-3-yl)-1,3-thiazole-2-carboxamide | 148 | 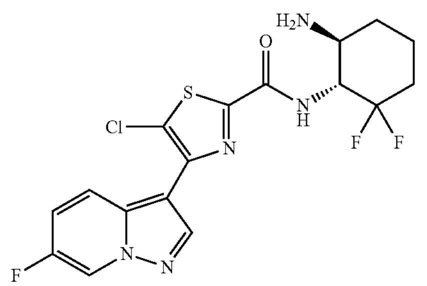 [SMILES: N[C@H]1CCCC(F)(F)[C@@H]1NC(=O)c1nc(-c2cnn3cc(F)ccc23)c(Cl)s1] | 430 |
| N-[(1R,6S)-6-amino-2,2-difluorocyclohexyl]-5-chloro-4-(5-chloropyrazolo[1,5-a]pyridine-3-yl)-1,3-thiazole-2-carboxamide | 149 | 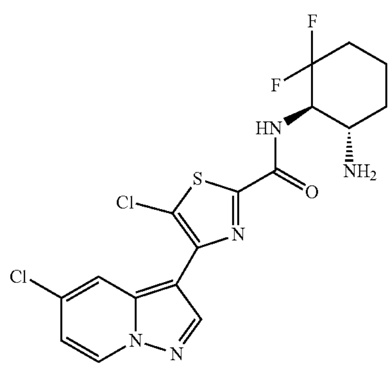 [SMILES: N[C@H]1CCCC(F)(F)[C@@H]1NC(=O)c1nc(-c2cnn3ccc(Cl)cc23)c(Cl)s1] | 446 |
| N-[(1R,6S)-6-Amino-2,2-difluorocyclohexyl]-5-chloro-4-(5-methylpyrazolo[1,5-a]pyridin-3-yl)-1,3-thiazole-2-carboxamide | 150 | 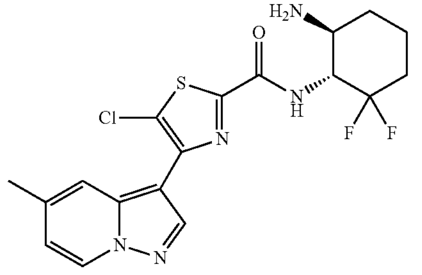 [SMILES: Cc1ccn2ncc(-c3nc(C(=O)N[C@@H]4[C@@H](N)CCCC4(F)F)sc3Cl)c2c1] | 426 |

| Name | Example # | Structure | LCMS M + H = |
|---|---|---|---|
| N-[(1R,6S)-6-Amino-2,2-difluorocyclohexyl]-5-chloro-4-(5-chloro-6-fluoropyrazolo[1,5-a]pyridin-3-yl)-1,3-thiazole-2-carboxamide | 151 | 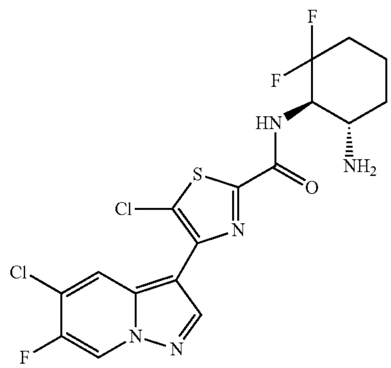 [SMILES: N[C@H]1CCCC(F)(F)[C@@H]1NC(=O)c1nc(-c2cnn3cc(F)c(Cl)cc23)c(Cl)s1] | 464 |
| N-[(1R,6S)-6-Amino-2,2-difluorocyclohexyl]-4-(6-ethylpyrazolo[1,5-a]pyridin-3-yl)-1,3-thiazole-2-carboxamide | 152 | 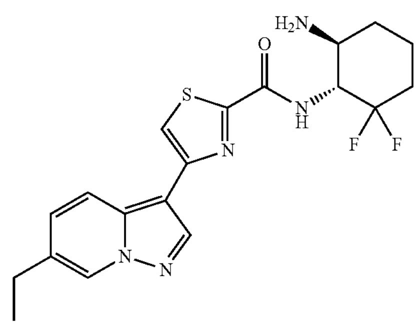 [SMILES: CCc1ccc2c(-c3csc(C(=O)N[C@@H]4[C@@H](N)CCCC4(F)F)n3)cnn2c1] | 406 |
| N-[(1R,6S)-6-Amino-2,2-difluorocyclohexyl]-4-(5-chloro-6-fluoropyrazolo[1,5-a]pyridin-3-yl)-1,3-thiazole-2-carboxamide | 153 | 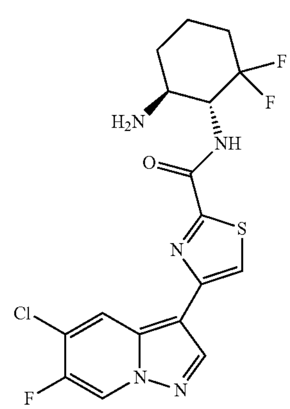 [SMILES: N[C@H]1CCCC(F)(F)[C@@H]1NC(=O)c1nc(-c2cnn3cc(F)c(Cl)cc23)cs1] | 430 |
| N-[(1R,6S)-6-Amino-2,2-difluorocyclohexyl]-4-(6-methoxypyrazolo[1,5-a]pyridin-3-yl)-1,3-thiazole-2-carboxamide | 154 | 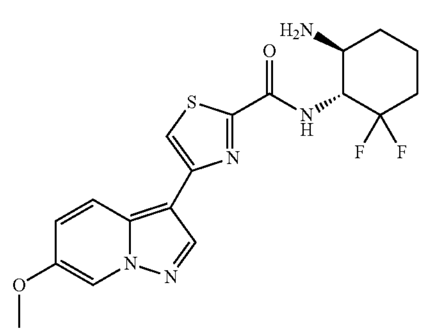 | 408 |

| Name | Example # | Structure | LCMS M + H = |
|---|---|---|---|
| N-[(1R,6S)-6-Amino-2,2-difluorocyclohexyl]-4-(5-cyanopyrazolo[1,5-a]pyridin-3-yl)-1,3-thiazole-2-carboxamide | 155 | 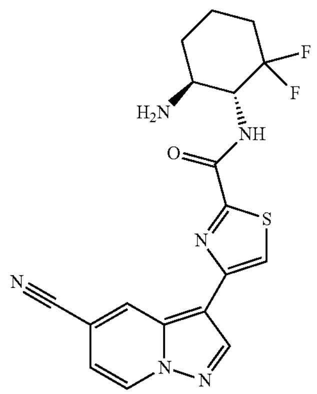 [SMILES: N#Cc1ccn2ncc(-c3csc(C(=O)N[C@@H]4[C@@H](N)CCCC4(F)F)n3)c2c1] | 403 |
| N-[(1R,6S)-6-Amino-2,2-difluorocyclohexyl]-4-(6-iodopyrazolo[1,5-a]pyridin-3-yl)-1,3-thiazole-2-carboxamide | 156 | 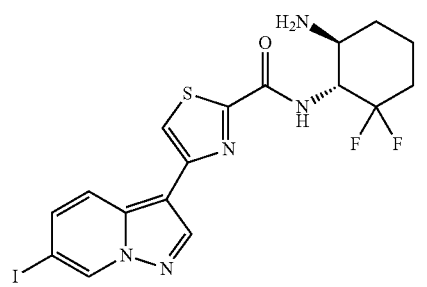 [SMILES: N[C@H]1CCCC(F)(F)[C@@H]1NC(=O)c1nc(-c2cnn3cc(I)ccc23)cs1] | 504 |
| N-[(1R,6S)-6-Amino-2,2-difluorocyclohexyl]-4-(6-isopropenylpyrazolo[1,5-a]pyridin-3-yl)-1,3-thiazole-2-carboxamide | 157 | 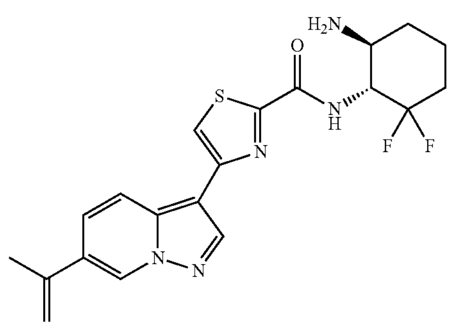 [SMILES: C=C(C)c1ccc2c(-c3csc(C(=O)N[C@@H]4[C@@H](N)CCCC4(F)F)n3)cnn2c1] | 418 |
| N-[(1R,6S)-6-Amino-2,2-difluorocyclohexyl]-4-(5-chloropyrazolo[1,5-a]pyridin-3-yl)-1,3-thiazole-2-carboxamide | 158 | 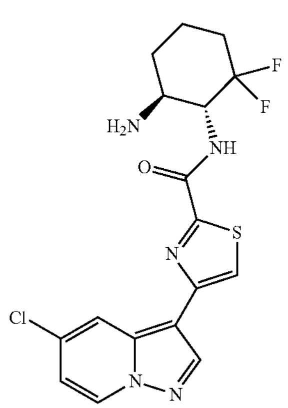 [SMILES: N[C@H]1CCCC(F)(F)[C@@H]1NC(=O)c1nc(-c2cnn3ccc(Cl)cc23)cs1] | 412 |

-continued

| Name | Example # | Structure | LCMS M + H = |
|------|-----------|-----------|--------------|
| N-[(1R,6S)-6-Amino-2,2-difluorocyclohexyl]-4-(6-cyanopyrazolo[1,5-a]pyridin-3-yl)-1,3-thiazole-2-carboxamide | 159 | 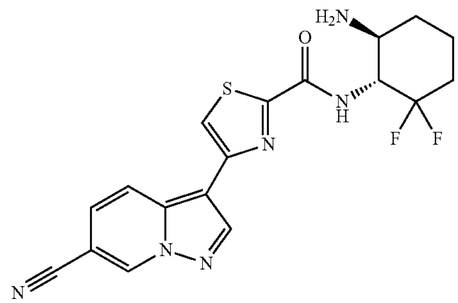 [SMILES: N#Cc1ccc2c(-c3csc(C(=O)N[C@@H]4[C@@H](N)CCCC4(F)F)n3)cnn2c1] | 403 |
| N-[(1R,6S)-6-Amino-2,2-difluorocyclohexyl]-4-[6-methoxy-5-(trifluoromethyl)pyrazolo[1,5-a]pyridin-3-yl]-1,3-thiazole-2-carboxamide | 160 | 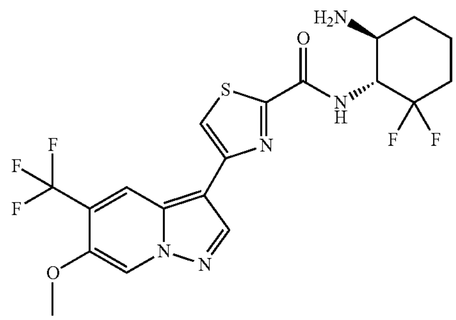 [SMILES: COc1cn2ncc(-c3csc(C(=O)N[C@@H]4[C@@H](N)CCCC4(F)F)n3)c2cc1C(F)(F)F] | 476 |
| N-[(1R,6S)-6-Amino-2,2-difluorocyclohexyl]-4-{6-[(trimethylsilyl)ethynyl]pyrazolo[1,5-a]pyridin-3-yl}-1,3-thiazole-2-carboxamide | 161 | 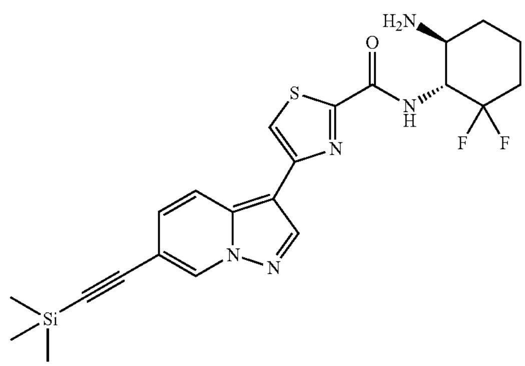 [SMILES: C[Si](C)(C)C#Cc1ccc2c(-c3csc(C(=O)N[C@@H]4[C@@H](N)CCCC4(F)F)n3)cnn2c1] | 474 |
| N-[(1R,6R)-6-Amino-2,2-difluorocyclohexyl]-5-chloro-4-(4,6-difluoropyrazolo[1,5-a]pyridin-3-yl)-1,3-thiazole-2-carboxamide | 162 | 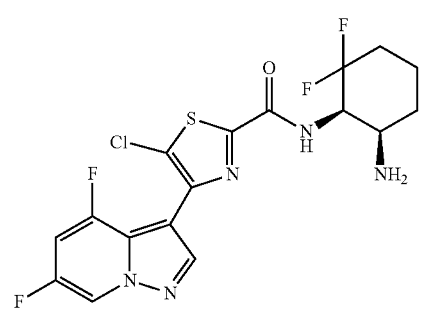 [SMILES: N[C@@H]1CCCC(F)(F)[C@@H]1NC(=O)c1nc(-c2cnn3cc(F)cc(F)c23)c(Cl)s1] | 448 |
| N-[(1R,6S)-6-Amino-2,2-difluorocyclohexyl]-4-(4-chloro-6-methoxypyrazolo[1,5-a]pyridin-3-yl)-1,3-thiazole-2-carboxamide | 163 | 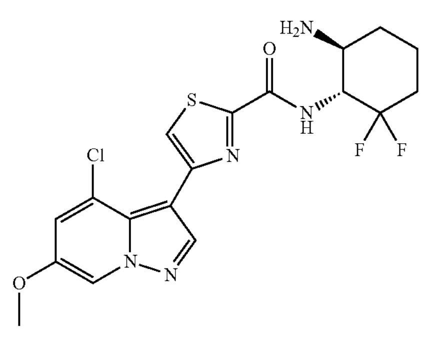 [SMILES: COc1cc(Cl)c2c(-c3csc(C(=O)N[C@@H]4[C@@H](N)CCCC4(F)F)n3)cnn2c1] | 442 |

-continued

| Name | Example # | Structure | LCMS M + H = |
|---|---|---|---|
| N-[(1R,6S)-6-Amino-2,2-difluorocyclohexyl]-4-(6-ethylpyrazolo[1,5-a]pyridin-3-yl)-1,3-thiazole-2-carboxamide | 164 | 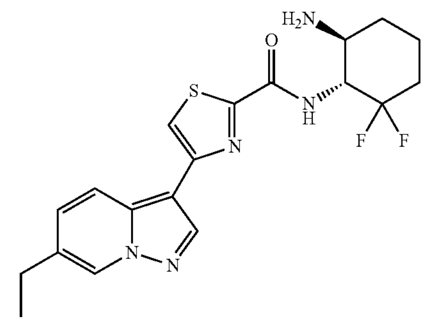 [SMILES: CCc1ccc2c(-c3csc(C(=O)N[C@@H]4[C@@H](N)CCCC4(F)F)n3)cnn2c1] | 406 |
| N-[(1R,6S)-6-Amino-2,2-difluorocyclohexyl]-4-(5-chloro-6-fluoropyrazolo[1,5-a]pyridin-3-yl)-1,3-thiazole-2-carboxamide | 165 | 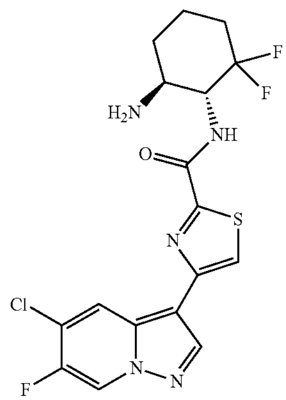 [SMILES: N[C@H]1CCCC(F)(F)[C@@H]1NC(=O)c1nc(-c2cnn3cc(F)c(Cl)cc23)cs1] | 430 |
| N-[(1R,6S)-6-Amino-2,2-difluorocyclohexyl]-4-(6-methoxypyrazolo[1,5-a]pyridin-3-yl)-1,3-thiazole-2-carboxamide | 166 | 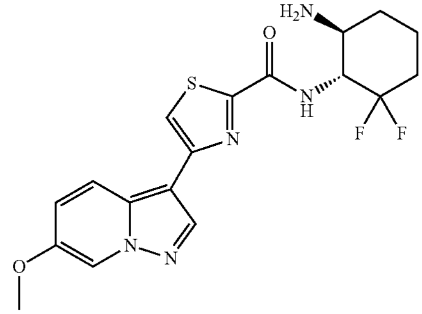 | 408 |
| N-[(1R,6S)-6-Amino-2,2-difluorocyclohexyl]-5-chloro-4-(6-cyclopropylpyrazolo[1,5-a]pyridin-3-yl)-1,3-thiazole-2-carboxamide | 167 | 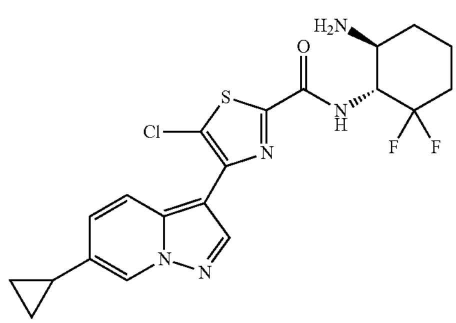 [SMILES: N[C@H]1CCCC(F)(F)[C@@H]1NC(=O)c1nc(-c2cnn3cc(C4CC4)ccc23)c(Cl)s1] | 452 |

Example 168

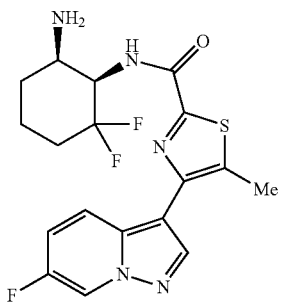 [SMILES: Cc1sc(C(=O)N[C@@H]2[C@H](N)CCCC2(F)F)nc1-c1cnn2cc(F)ccc12]

N-[(1R,6R)-6-Amino-2,2-difluorocyclohexyl]-5-methyl-pyrazolo pyridine-3-yl-1,3-thiazole-2-carboxamide (Scheme 1)

Synthesis began in an analogous fashion to example 1, step A, part 1. Variable functionality on the core pyridine ring was introduced via the use of an appropriately functionalized pyridine in step A, part 2, which in this case was 3-fluoropyridine. The synthesis continued with the use of step C (such that step B was not carried out). Introduction of the 5-alkyl thiazole moiety was accomplished via the procedure in example 1, part C, step 3 but substituting diethylzinc (1M in hexanes) as the reagent in the reaction (in place of dimethylzinc). Alternatively, the cyclization step (example 1, step A, part 3) was carried out with the appropriate ynone (RCH$_2$COCH, R=Me, Et, i-Pr) in THF at RT to directly provide the corresponding ketone carried into step D (example 1). All subsequent steps were analogous to that of example 1 with the use of known or commercial diamines in step E, part 3. MS APCI: [M+H]$^+$ m/z 410. $^1$H NMR (500 MHz, DMSO-d$_6$): δ 9.08 (1H, d, J=1.95 Hz), 8.43 (1H, s), 8.22-8.19 (1H, m), 7.49-7.46 (1H, m), 4.37-4.25 (1H, m), 3.15 (1H, br s), 2.13-2.00 (1H, m), 2.00-1.81 (1H, m), 1.79-1.67 (2H, m), 1.67-1.50 (2H, m).

The following examples were prepared in an analogous manner of that described in example 168 with the use of known or commercial amines in step E, part 3.

| Name | Example # | Structure | LCMS M + H = |
|---|---|---|---|
| N-[(1R,6R)-6-Amino-2,2-difluorocyclohexyl]-4-(4-fluoropyrazolo[1,5-a]pyridin-3-yl)-5-methyl-1,3-thiazole-2-carboxamide | 169 | 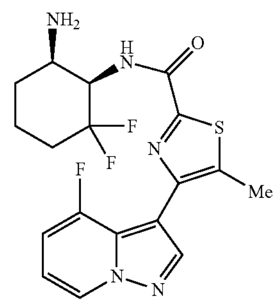 [SMILES: Cc1sc(C(=O)N[C@@H]2[C@H](N)CCCC2(F)F)nc1-c1cnn2cccc(F)c12] | 410 |
| N-[(1R,6S)-6-Amino-2,2-difluorocyclohexyl]-5-ethyl-4-(6-fluoropyrazolo[1,5-a]pyridin-3-yl)thiophene-2-carboxamide | 170 | 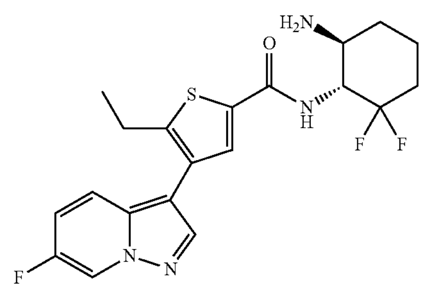 [SMILES: CCc1sc(C(=O)N[C@@H]2[C@@H](N)CCCC2(F)F)cc1-c1cnn2cc(F)ccc12] | 423 |
| N-[(1R,6S)-6-Amino-2,2-difluorocyclohexyl]-5-isopropyl-4-pyrazolo[1,5-a]pyridin-3-yl-1,3-thiazole-2-carboxamide | 171 | 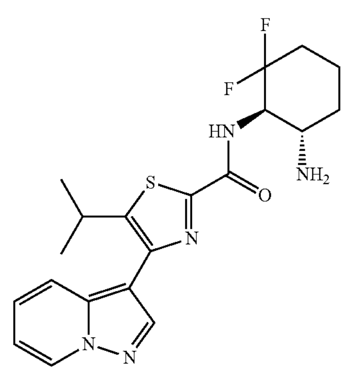 [SMILES: CC(C)c1sc(C(=O)N[C@@H]2[C@@H](N)CCCC2(F)F)nc1-c1cnn2ccccc12] | 420 |

-continued
| Name | Example # | Structure | LCMS M + H = |
|---|---|---|---|
| N-[(1R,6R)-6-Amino-2,2-difluorocyclohexyl]-5-isopropyl-4-pyrazolo[1,5-a]pyridin-3-yl-1,3-thiazole-2-carboxamide | 172 | 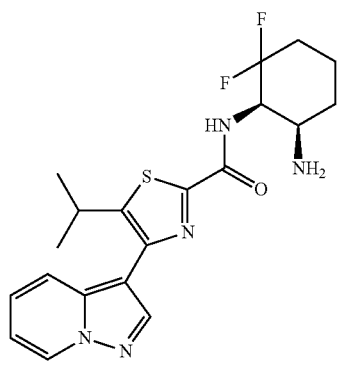 [SMILES: CC(C)c1sc(C(=O)N[C@@H]2[C@H](N)CCCC2(F)F)nc1-c1cnn2ccccc12] | 420 |
| N-[(1R,6S)-6-amino-2,2-difluorocyclohexyl]-5-ethyl-4-[6-(trifluoromethyl)pyrazolo-[1,5-a]pyridin-3-yl]thiophene-2-carboxamide | 173 | 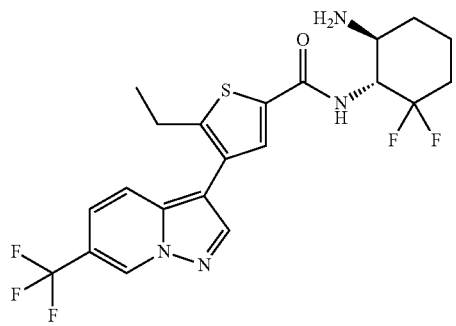 [SMILES: CCc1sc(C(=O)N[C@@H]2[C@@H](N)CCCC2(F)F)cc1-c1cnn2cc(C(F)(F)F)ccc12] | 473 |
| N-[(1R,6S)-6-Amino-2,2-difluorocyclohexyl]-5-ethyl-4-pyrazolo[1,5-a]pyridin-3-yl-1,3-thiazole-2-carboxamide | 174 | 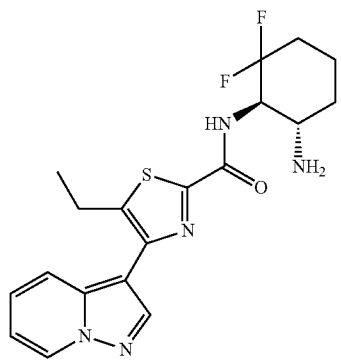 [SMILES: CCc1sc(C(=O)N[C@@H]2[C@@H](N)CCCC2(F)F)nc1-c1cnn2ccccc12] | 406 |

-continued

| Name | Example # | Structure | LCMS M + H = |
|---|---|---|---|
| N-[(1R,6R)-6-Amino-2,2-difluorocyclohexyl]-4-(6-chloropyrazolo[1,5-a]pyridin-3-yl)-5-methyl-1,3-thiazole-2-carboxamide | 175 | 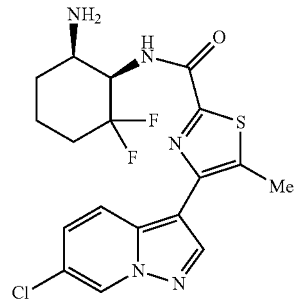 [SMILES: Cc1sc(C(=O)N[C@@H]2[C@H](N)CCCC2(F)F)nc1-c1cnn2cc(Cl)ccc12] | 427 |
| N-[(1R,6R)-6-Amino-2,2-difluorocyclohexyl]-4-(6-bromopyrazolo[3,5-a]pyridin-3-yl)-5-methyl-1,3-thiazole-2-carboxamide | 176 | 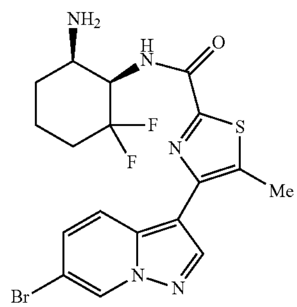 | 471 |
| N-[(1R,6S)-6-Amino-2,2-difluorocyclohexyl]-5-methyl-4-pyrazolo[1,5-a]pyridin-3-yl-1,3-thiazole-2-carboxamide | 177 | 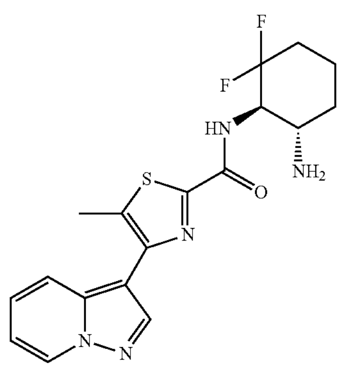 [SMILES: Cc1sc(C(=O)N[C@@H]2[C@@H](N)CCCC2(F)F)nc1-c1cnn2ccccc12] | 392 |
| N-[(1R,6S)-6-Amino-2,2-difluorocyclohexyl]-4-(6-fluoropyrazolo[1,5-a]pyridin-3-yl)-5-methyl-1,3-thiazole-2-carboxamide | 178 | 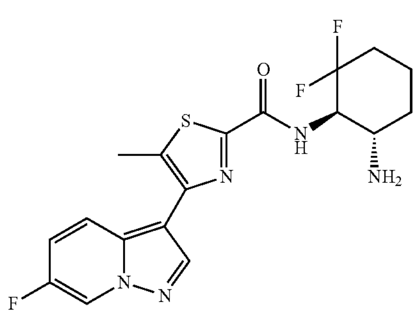 [SMILES: Cc1sc(C(=O)N[C@@H]2[C@@H](N)CCCC2(F)F)nc1-c1cnn2cc(F)ccc12] | 410 |

Example 179

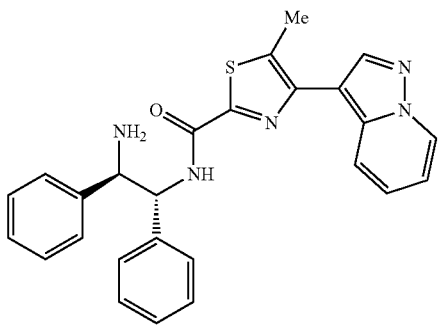 [SMILES: Cc1sc(C(=O)N[C@H](c2ccccc2)[C@H](N)c2ccccc2)nc1-c1cnn2ccccc12]

N-[(1R,2R)-2-Amino-1,2-diphenylethyl]-5-methyl-4-pyrazolo[1,5-a]pyridin-3-yl]-1,3-thiazole-2-carboxamide (Scheme 1)

Synthesis began using commercially available pyrazolo[1,5-a]pyridine-3-carboxylic acid or material obtained via example 1, step A then following the procedure outlined in example 1, part C, steps 1 and 2 to obtain the corresponding acid chloride. Introduction of the 5-methyl thiazole moiety was accomplished via the procedure in example 1, part C, step 3 but substituting diethylzinc (1M in hexanes) as the reagent in the reaction (in place of dimethylzinc). All subsequent steps were analogous to that of example 1 with the use of known or commercial diamines in step E, part 3. MS APCI: [M+H]+ m/z 454.6. ¹H NMR (500 MHz, DMSO-d₆): δ 8.97 (1H, d, J=8.0 Hz), 8.80 (1H, s, J=6.5 Hz), 8.43 (1H, s), 8.31 (2H, d, J=9.0 Hz), 7.48-7.45 (1H, m), 7.41 (2H, apparent d, J=7.3 Hz), 7.33 (2H, apparent d, J=7.3 Hz), 7.29-7.23 (4H, m), 7.21-7.15 (2H, m), 7.05 (1H, dt, J=0.98, 6.9 Hz), 5.03 (1H, m), 4.42 (1H, d, J=5.5 Hz), 2.62 (3H, s).

The following examples were prepared in an analogous manner of that described in example 179 with the use of known or commercial amines in step E, part 3.

| Name | Example # | Structure | LCMS M + H = |
|---|---|---|---|
| N-[(cis)-2-aminocyclohexyl]-5-methyl-4-pyrazolo[1,5-a]pyridin-3-yl]-1,3-thiazole-2-carboxamide | 180 | 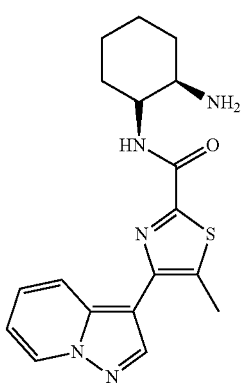 | 356 |

Example 181

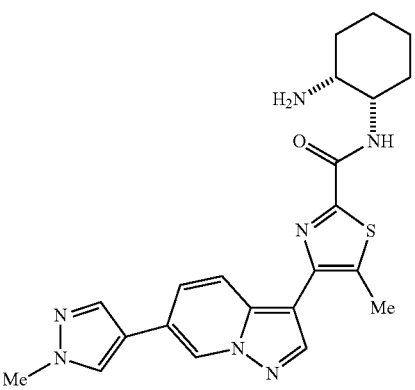

N-[(cis)-2-Aminocyclohexyl]-5-methyl-4-[6-(1-methyl-1H-pyrazol-4-yl)pyrazolo[1,5-a]pyridin-3-yl]-1,3-thiazole-2-carboxamide (Scheme 1)

Synthesis began in an analogous fashion to example 1, steps A and B (using the appropriate commercial boronic acid or ester in the Suzuki reaction). Introduction of the 5-methyl thiazole moiety was accomplished via the procedure in example 1, part C, however step 3 was modified by the use of diethylzinc (1M in hexanes) as the reagent in the reaction (versus the use of dimethylzinc). All subsequent steps were analogous to that of example 1 with the use of known or commercial diamines in step E, part 3. MS APCI: [M+H]+ m/z 436.6. ¹H NMR (500 MHz, DMSO-d₆): δ 9.08 (1H, s), 8.38 (1H, s), 8.29 (1H, s), 8.19 (1H, d, J=9.3 Hz), 8.04 (1H, s), 7.62 (1H, dd, J=1.5, 9.3 Hz), 4.14 (1H, bs), 3.87 (3H, s), 3.35 (1H, bs), 2.64 (3H, s), 1.84-1.75 (1H, m), 1.72-1.55 (3H, m) 1.48-1.34 (2H, m), 0.87-0.74 (2H, m).

The following examples were prepared in an analogous manner of that described in example 181 with the use of known or commercial amines in step E, part 3,

| Name | Example # | Structure | LCMS M + H = |
|---|---|---|---|
| N-(2-Amino-1-phenylethyl)-5-methyl-4-[6-(1-methyl-1H-pyrazol-4-yl)pyrazolo[1,5-a]pyridin-3-yl]-1,3-thiazole-2-carboxamide | 182 | 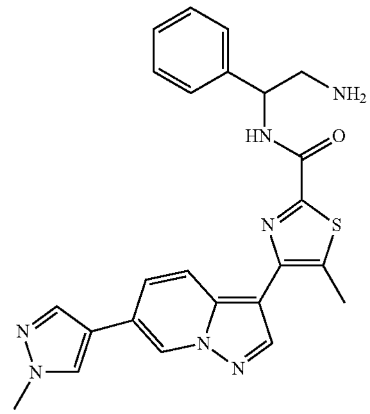 | 458 |
| N-[(1S,2S)-2-Amino-1,2-diphenyl]-5-methyl-4-[6-(1-methyl-1H-pyrazol-4-yl)pyrazolo[1,5-a]pyridin-3-yl]-1,3-thiazole-2-carboxamide | 183 | 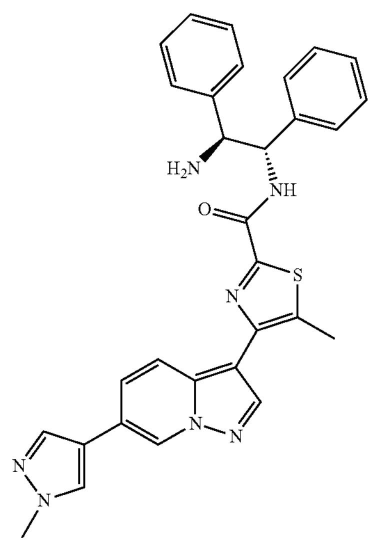 [SMILES: Cc1sc(C(=O)N[C@@H](c2ccccc2)[C@@H](N)c2ccccc2)nc1-c1cnn2cc(-c3cnn(C)c3)ccc12] | 534 |
| N-[(1R,6R)-6-Amino-2,2-difluorocyclohexyl]-5-methyl-4-[6-(1-methyl-1H-pyrazol-4-yl)pyrazolo[1,5-a]pyridin-3-yl]-1,3-thiazole-2-carboxamide | 184 | 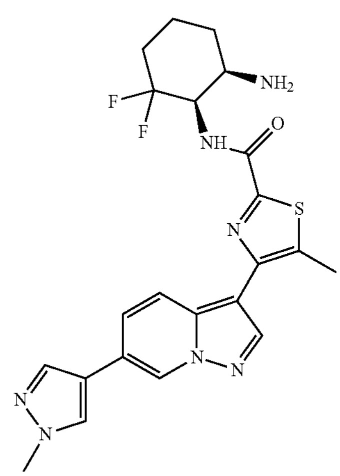 [SMILES: Cc1sc(C(=O)N[C@@H]2[C@H](N)CCCC2(F)F)nc1-c1cnn2cc(-c3cnn(C)c3)ccc12] | 472 |

| Name | Example # | Structure | LCMS M + H = |
|---|---|---|---|
| N-[(1S)-2-Hydroxy-1-phenylethyl]-5-methyl-4-[6-(1-methyl-1H-pyrazol-4-yl)pyrazolo[1,5-a]pyridin-3-yl]-1,3-thiazole-2-carboxamide | 185 | 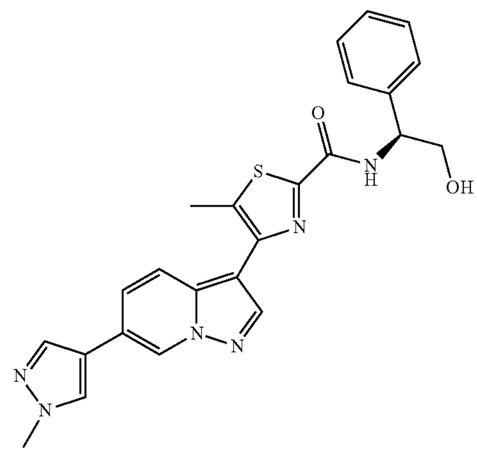 [SMILES: Cc1sc(C(=O)N[C@H](CO)c2ccccc2)nc1-c1cnn2cc(-c3cnn(C)c3)ccc12] | 459 |
| N-[(1S)-1-(2-Chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 186 | 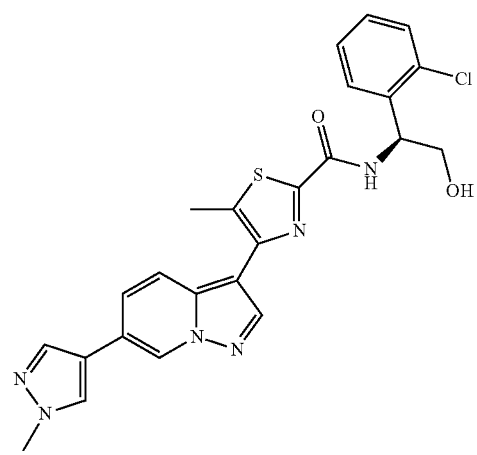 [SMILES: Cc1sc(C(=O)N[C@H](CO)c2ccccc2Cl)nc1-c1cnn2cc(-c3cnn(C)c3)ccc12] | 494 |
| N-[(1S)-1-(3-Chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 187 | 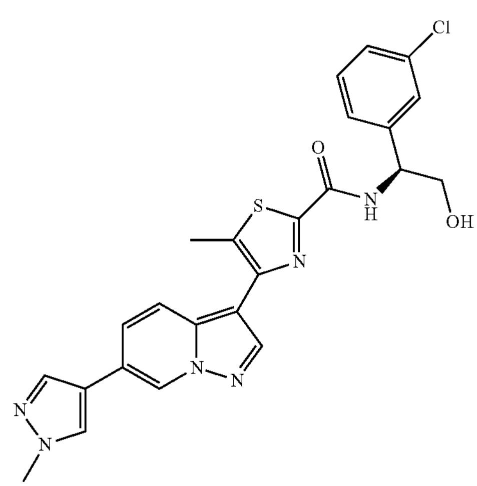 [SMILES: Cc1sc(C(=O)N[C@H](CO)c2cccc(Cl)c2)nc1-c1cnn2cc(-c3cnn(C)c3)ccc12] | 494 |

-continued

| Name | Example # | Structure | LCMS M + H = |
|---|---|---|---|
| N-[(1S)-(3-Chloro-5-fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 188 | 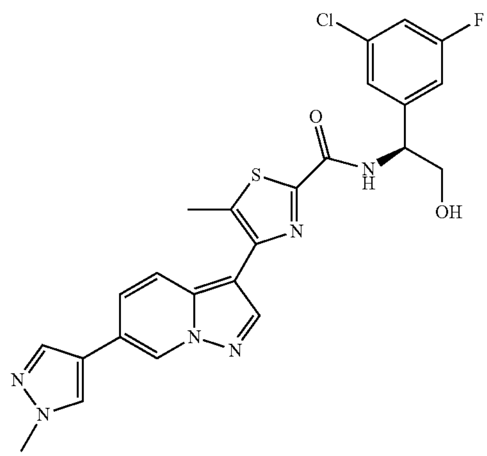 [SMILES: Cc1sc(C(=O)N[C@H](CO)c2cc(F)cc(Cl)c2)nc1-c1cnn2cc(-c3cnn(C)c3)ccc12] | 512 |
| N-[(1S)-1-(4-Chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 189 | 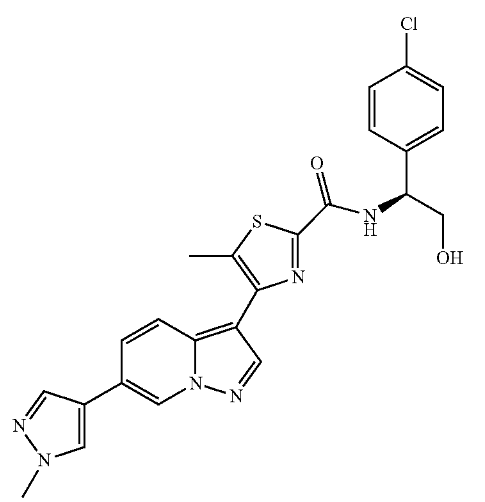 | 494 |
| N-(1S)-1-(3-Fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 190 | 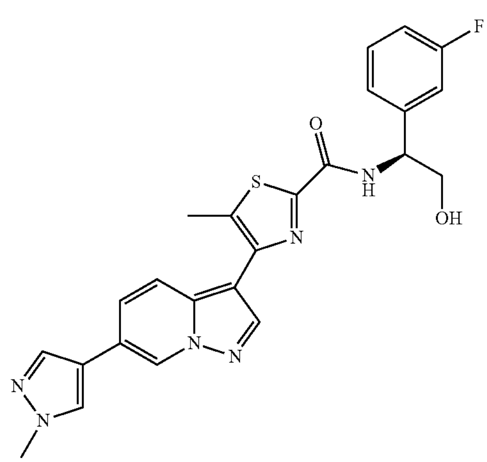 [SMILES: Cc1sc(C(=O)N[C@H](CO)c2cccc(F)c2)nc1-c1cnn2cc(-c3cnn(C)c3)ccc12] | 478 |

-continued

| Name | Example # | Structure | LCMS M + H = |
|---|---|---|---|
| N-[(1S)-1-(4-Chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide | 191 | 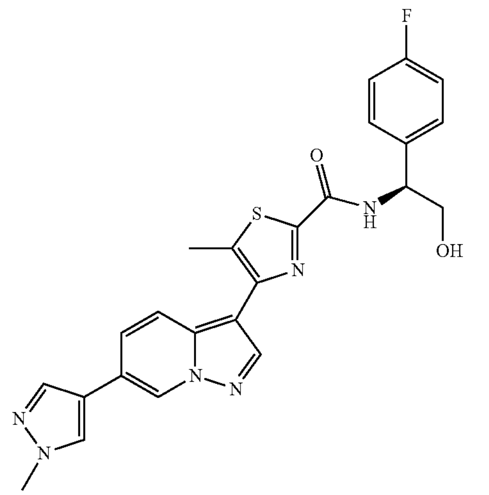 [SMILES: Cc1sc(C(=O)N[C@H](CO)c2ccc(F)cc2)nc1-c1cnn2cc(-c3cnn(C)c3)ccc12] | 478 |

Example 192

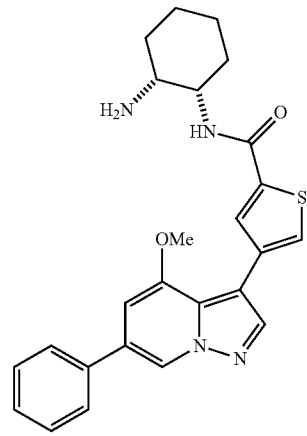

N-[(cis)-2-Aminocyclohexyl]-4-(4-methoxy-6-[phenylpyrazolo{1,5-a]pyridine-3-yl)-2-thiophenecarboxamide (Scheme 2)

Step A: Cyclization

Synthesis began in an analogous manner to example 1, step 1, part A employing O-mesitylenesulfonylhydroxylamine (1) and 3-bromo-5-methoxypyridine to access cyclized product, ethyl 6-bromo-4-methoxylpyrazolo[1,5-a]pyridine-3-carboxylate (15). MS APCI: $[M+H]^+$ m/z 300.1.

Step B: Decarboxylation

A solution of ethyl 6-bromo-4-methoxylpyrazolo[1,5-a]pyridine-3-carboxylate (15, 5.2 g, 18.24 mmol) in HBr (100 ml, 884 mmol) was heated to 100° C. for 1 hour. After cooling to 0° C., 1M NaOH (182 ml, 912 mmol) was used to neutralize the solution. The reaction mixture was diluted in ethyl acetate, washed with saturated aqueous sodium hydroxide (1N) and brine then dried over $Na_2SO_4$. After filtration and concentration, the residue was purified by column chromatography (0-35% EtOAc in hexanes, linear gradient) to give 6-bromo-4-methoxypyrazolo[1,5-a]pyridine (16, 2.475 g, 10.90 mmol, 60% yield). MS APCI: $[M+H]^+$ m/z 228.1.

Step C: Suzuki Coupling

A Suzuki coupling reaction analogous to example 1, part B was carried out using phenyl boronic acid (or the appropriate commercially available boronic ester or acid) to yield coupled product 4-methoxy-6-phenylpyrazolo[1,5-a]pyridine (17). MS APCI: $[M+H]^+$ m/z 225.3.

Step D: Halogenation 4-methoxy-6-phenylpyrazolo[1,5-a]pyridine (17, 200 mg, 0.892 mmol) and NIS (241 mg, 1.070 mmol) were dissolved in acetonitrile (20 mL) and stirred at room temperature for 1 hour. The reaction was then poured into ethyl acetate and water, extracted organics, washed 1N NaOH and brine, dried with magnesium sulfate, filtered, and concentrated to give a white solid. This was purified by column chromatography (0-30% ethyl acetate in hexanes, linear gradient) and to yield 3-iodo-4-methoxypyrazolo[1,5-a]pyridine (18, 310 mg, 0.885 mmol, 99% yield). MS APCI: $[M+H]^+$ m/z 351.2.

Step E: Suzuki Coupling

A Suzuki coupling reaction analogous to step C was carried out using known boronic ester, ethyl 4-(4,4,5,5-tetramethyl-1,3,2-dioxaborolan-2-yl)-2-thiophenecarboxylate (see WO 2004052286 A2 and WO 2007085873 A1) to yield coupled product, 4-(4-methoxy-6-phenylpyrazolo[1,5-a]pyridine-3-yl)-2-thiophenecarboxylate (19). MS APCI: $[M+H]^+$ m/z 389.4.

Step F: Coupling

Part 1: Ester Saponification 4-(4-Methoxy-6-phenylpyrazolo[1,5-a]pyridine-3-yl)-2-thiophenecarboxylate (19, 58 mg, 0.159 mmol) and 1N sodium hydroxide (0.5 mL, 0.5 mmol) were added to methanol (6 mL) and water (0.2 mL). The reaction was heated to 70° C. and stirred for 2 hours. Upon cooling the reaction to room temperature, 1N HCl (0.5 mL) was added to the reaction. Concentration and purification by HPLC (20-100% acetonitrile in water, 0.05% TFA modifier, linear gradient) provided 4-(4-methoxy-6-phenylpyrazolo[1,5-d]pyridine-3-yl)-2-thiophenecarboxylic acid (20, 40 mg, 0.114 mmol, 72% yield). MS APCI: $[M+H]^+$ m/z 351.4.

Part 2: Amide Synthesis 4-(4-Methoxy-6-phenylpyrazolo[1,5-a]pyridine-3-yl)-2-thiophenecarboxylic acid (20, 10 mg, 0.029 mmol) and CDI (9.26 mg, 0.057 mmol) were added to DMF (2 ml). The reaction was stirred at ambient temperature for 15 minutes before quenching with cis-1,2-diaminocyclohexane (0.034 ml, 0.285 mmol). After 30 minutes, DMSO/acetonitrile/water were added to the reaction and the crude reaction mixture was purified by HPLC (10-100% acetonitrile in water, 0.05% TFA modifier, linear gradient). N-[(cis)-2-aminocyclohexyl]-4-(4-methoxy-6-[phenylpyrazolo{1,5-a]pyridine-3-yl)-2-thiophenecarboxamide (21) was isolated in quantitative yield (13 mg, 0.029 mmol), MS APCI: [M+H]$^+$ m/z 447.2. $^1$H NMR (500 MHz, DMSO-d$_6$): δ 8.66 (1H, s), 8.23 (1H, s), 8.22 (1H, s), 7.86-7.82 (4H, m), 7.49 (2H, t, J=7.50 Hz), 7.40 (2H, t, J=7.50 Hz), 4.03 (3H, s), 3.96-3.89 (1H, m), 3.09-3.04 (1H, m), 1.77-1.67 (1H, m), 1.67-1.46 (3H, m), 1.37-1.20 (2H, m), 0.89-0.82 (2H, m).

The following examples were prepared in an analogous manner to that of example 192 with the use of commercial amines in step F, part 2, and/or the use of intermediate 2 in step E, and/or the use of varying pyridines in step A.

| Name | Example # | Structure | LCMS M + H = |
|---|---|---|---|
| N-[(1R,6R)-6-Amino-2,2-difluorocyclohexyl]-4-methoxy-6-phenylpyrazolo[1,5-a]pyridin-3-yl]-2-thiophenecarboxamide | 193 | 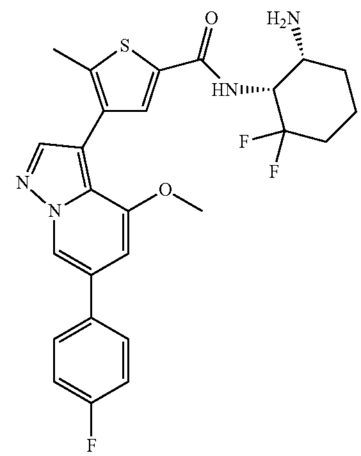 [SMILES: COc1cc(-c2ccc(F)cc2)cn2ncc(-c3cc(C(=O)N[C@@H]4[C@H](N)CCCC4(F)F)sc3C)c12] | 515 |
| 4-(4-Methoxy-6-(1-methyl-1 H-pyrazol-4-yl)pyrazolo[1,5-a]pyridin-3-yl]-2-thiophenecarboxamide | 194 | 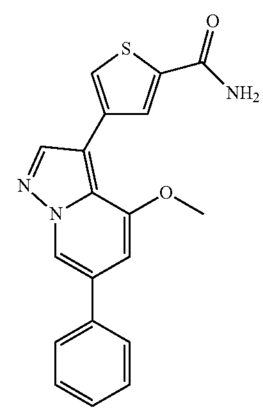 [SMILES: COc1cc(-c2ccccc2)cn2ncc(-c3csc(C(N)=O)c3)c12] | 350 |
| N-[(1S)-2-Hydroxy-1-phenylethyl]-4-methoxy-6-phenylpyrazolo[1,5-a]pyridin-3-yl]-2-thiophenecarboxamide | 195 | 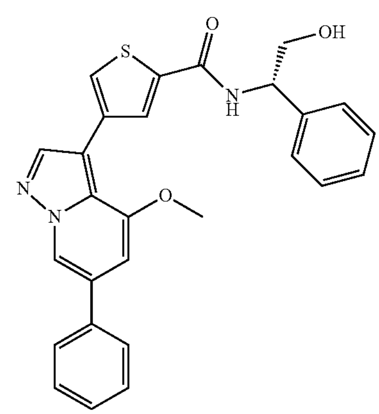 [SMILES: COc1cc(-c2ccccc2)cn2ncc(-c3csc(C(=O)N[C@H](CO)c4ccccc4)c3)c12] | 471 |

| Name | Example # | Structure | LCMS M + H = |
|---|---|---|---|
| N-[(1S)-2-Hydroxy-1-phenylethyl]-4-methoxy-6-(1-methyl-1 H-pyrazol-4-yl)pyrazolo[1,5-a]pyridin-3-yl]-2-thiophenecarboxamide | 196 | 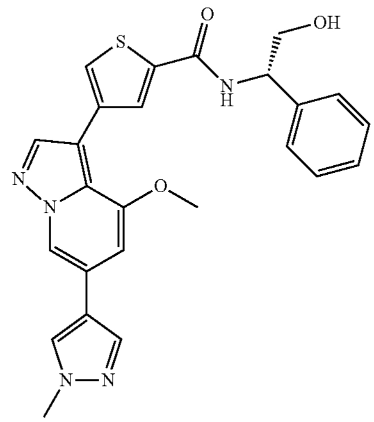 [SMILES: COc1cc(-c2cnn(C)c2)cn2ncc(-c3csc(C(=O)N[C@H](CO)c4ccccc4)c3)c12] | 474 |
| N-[(1R,6R)-6-Amino-2,2-difluorocyclohexyl]-4-[6-fluorophenyl)pyrazolo[1,5-a]pyridin-3-yl]-5-methyl-2-thiophenecarboxamide | 197 | 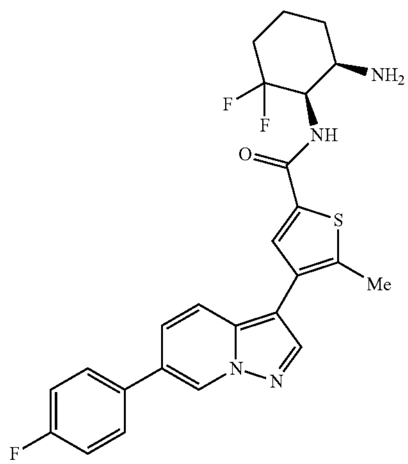 [SMILES: Cc1sc(C(=O)N[C@@H]2[C@H](N)CCCC2(F)F)cc1-c1cnn2cc(-c3ccc(F)cc3)ccc12] | 485 |
| N-(3-Amino-4,4,4-trifluorobutyl)-4-(4-methoxy-6-phenylpyrazolo[1,5-a]pyridin-3-yl]-2-thiophenecarboxamide | 198 | 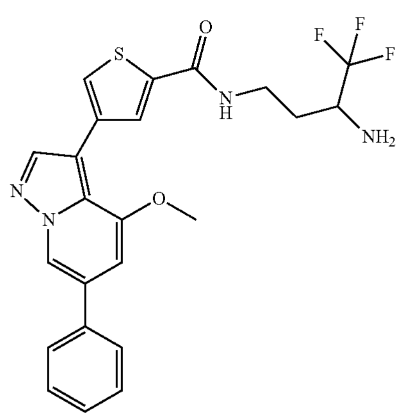 [SMILES: COc1cc(-c2ccccc2)cn2ncc(-c3csc(C(=O)NCCC(N)C(F)(F)F)c3)c12] | 475 |

Example 199

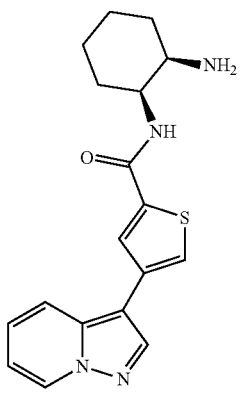 [SMILES: N[C@@H]1CCCC[C@@H]1NC(=O)c1cc(-c2cnn3ccccc23)cs1]

N-[(cis)-2-Aminocyclohexyl]-4-pyrazolo[1,5-a]pyridin-3-yl]-2-thiophenecarboxamide (Scheme 2)

Synthesis began with the use of commercial 3-bromopyrazolo[1,5-a]pyridine and employing the procedure in example 28, step E and step F, part 1 to obtain the corresponding carboxylic acid product. Alternatively, following protocol outlined in example 186, step A and B with the appropriately functionalized pyridine provides corresponding product. Final amide coupling conditions were modified from that of example 28 (step F, part 2). To 4-pyrazolo[1,5-a]pyridin-3-yl]-2-thiophenecarboxylic acid (50 mg, 0.205 mmol) and BOP (136 mg, 0.307 mmol) in DMF (2.5 mL) was added commercially available (cis)-1,2-cyclohexyldiamine (0.241 mL, 2.047 mmol) followed by DIPEA (0.107 mL, 0.614 mmol). The reaction mixture was allowed to stir at room temperature overnight. The reaction mixture was then filtered and the filtrate purified by column chromatography (1-15% MeOH in dicholoromethane, linear gradient) to yield N-[(cis)-2-aminocyclohexyl]-4-pyrazolo[1,5-a]pyridin-3-yl]-2-thiophenecarboxamide (65 mg, 0.191 mmol, 93% yield). MS APCI: [M+H]$^+$ m/z 338.1. $^1$H NMR (600 MHz, DMSO-d$_6$): δ 8.69 (1H, d, J=6.60 Hz), 8.61 (1H, d, J=1.20 Hz), 8.40 (1H, d, J=1.20 Hz), 8.36 (1H, s), 8.15-8.14 (3H, m), 7.95 (2H, d, J=1.20 Hz), 7.32 (1H, ddd, J=1.20, 2.40, 6.60 Hz), 6.93 (1H, dt, J=1.20, 6.60 Hz), 4.23 (1H, broad s), 2.47-1.88 (1H, m), 1.84-1.79 (1H, m), 1.72-1.59 (4H, m), 1.38 (2H, m).

The following examples were prepared in an analogous manner to that of example 199 with the use of commercial amines in step F, part 2, and/or the use of intermediate 2 in step E, and/or the use of varying pyridines in step A.

| Name | Example # | Structure | LCMS M + H = |
|---|---|---|---|
| N-[(1R,6S)-6-Amino-2,2-difluorocyclohexyl]-4-(4,6-difluoropyrazolo[1,5-a]pyridin-3-yl)-5-methylthiophene-2-carboxamide | 200 | 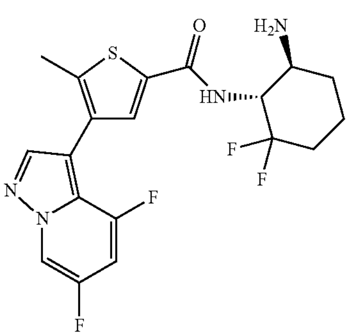 [SMILES: Cc1sc(C(=O)N[C@@H]2[C@@H](N)CCCC2(F)F)cc1-c1cnn2cc(F)cc(F)c12] | 426 |
| N-[(trans)-4-Amino-1,1-dioxidotetrahydro-2H-thiopyran-3-yl]-5-methyl-4-(pyrazolo[1,5-a]pyridin-3-yl) thiophene-2-carboxamide | 201 | 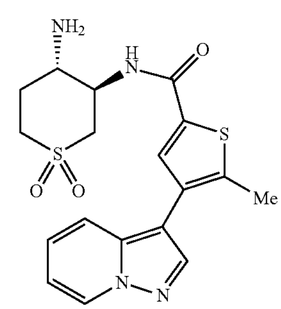 [SMILES: Cc1sc(C(=O)N[C@H]2CS(=O)(=O)CC[C@@H]2N)cc1-c1cnn2ccccc12] | 405 |

-continued

| Name | Example # | Structure | LCMS M + H = |
|---|---|---|---|
| N-[(cis)-4-Amino-1,1-dioxidotetrahydro-2H-thiopyran-3-yl]-5-methyl-4-(pyrazolo[1,5-a]pyridin-3-yl) thiophene-2-carboxamide | 202 | 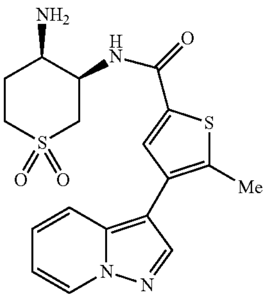 [SMILES: Cc1sc(C(=O)N[C@H]2CS(=O)(=O)CC[C@H]2N)cc1-c1cnn2ccccc12] | 405 |
| N-[(1R,6S)-6-Amino-2,2-difluorocyclohexyl]-5-ethyl-4-[6-(tri-fluoromethyl)pyrazolo-[1,5-a]pyridin-3-yl]thiophene-2-carboxamide | 203 | 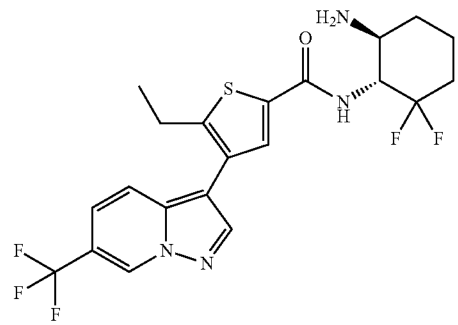 [SMILES: CCc1sc(C(=O)N[C@@H]2[C@@H](N)CCCC2(F)F)cc1-c1cnn2cc(C(F)(F)F)ccc12] | 473 |
| N-[(1R,6S)-6-Amino-2,2-difluorocyclohexyl]-5-ethyl-4-(6-fluoropyrazolo[1,5-a]pyridin-3-yl)thiophene-2-carboxamide | 204 | 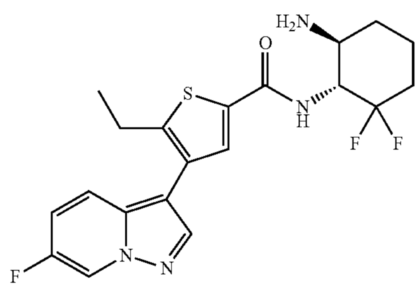 [SMILES: CCc1sc(C(=O)N[C@@H]2[C@@H](N)CCCC2(F)F)cc1-c1cnn2cc(F)ccc12] | 423 |
| N-[(1R,6S)-6-Amino-2,2-difluorocyclohexyl]-4-(4,6-difluoropyrazolo[1,5-a]pyridin-3-yl)-5-methylthiophene-2-carboxamide | 205 | 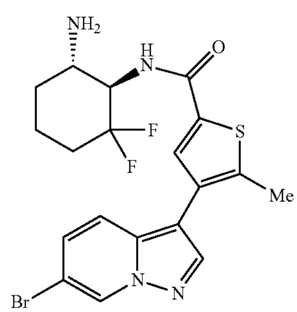 [SMILES: Cc1sc(C(=O)N[C@@H]2[C@@H](N)CCCC2(F)F)cc1-c1cnn2cc(Br)ccc12] | 426 |

Example 206

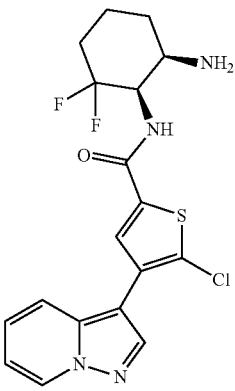 [SMILES: N[C@@H]1CCCC(F)(F)[C@@H]1NC(=O)c1cc(-c2cnn3ccccc23)c(Cl)s1]

N-[(1R,6R)-6-amino-2,2-difluorocyclohexyl]-5-chloro-4-pyrazolo[1,5-a]pyridin-3-yl-2-thiophenecarboxamide (Scheme 6)

Synthesis began with the use of commercial 3-bromopyrazolo[1,5-a]pyridine and then employing the procedure in example 191, step E (scheme 2) using intermediate 2 as the Suzuki coupling partner. The protocol in subsequent step F, part 1 provides carboxylic acid product 36. To 4-pyrazolo[1,5-a]pyridin-3-yl]-2-thiophenecarboxylic acid (50 mg, 0.205 mmol) is added thionyl chloride (1 mL). The reaction mixture was allowed to stir at 70° C. overnight. The excess thionyl chloride is removed under reduced pressure. The yellow solid 37 is solubilized in dichloromethane (3 mL) and exposed to amine 28. After 1 hr, TFA (0.5 mL) is added to the reaction and the material was purified by reverse phase chromatography (10-90% water in acetonitrile, linear gradient) to yield N-[(1R,6R)-6-amino-2,2-difluorocyclohexyl]-5-chloro-4-pyrazolo[1,5-a]pyridin-3-yl-2-thiophenecarboxamide (16.1 mg, 22% yield). MS APCI: [M+H]$^+$ m/z 411. $^1$H NMR (600 MHz, DMSO-d$_6$): δ 8.78 (1H, d, J=7.34 Hz), 8.33 (1H, s), 8.27 (1H, s), 7.79 (1H, d, J=8.8 Hz), 7.40 (1H, t, J=6.8 Hz), 7.01 (1H, t, J=6.8 Hz), 4.50 (1H, br s), 3.04 (1H, br s), 2.16-2.01 (1H, m), 1.92-1.80 (1H, m), 1.76-1.67 (1H, m), 1.64-1.51 (2H, m), 1.49-1.39 (1H, m).

The following examples were prepared in an analogous manner to that of example 206 with the use of commercial amines in step F, part 2.

| Name | Example # | Structure | LCMS M + H = |
|---|---|---|---|
| A-[(trans)-4-amino-1,1-dioxidotetrahydro-2H-thiopyran-3-yl]-5-chloro-4-(pyrazolo[1,5-a]pyridin-3-yl) thiophene-2-carboxamide | 207 | 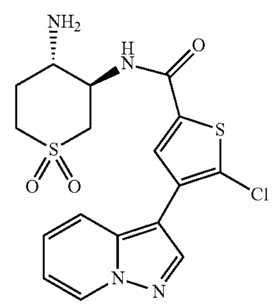 [SMILES: N[C@H]1CCS(=O)(=O)C[C@@H]1NC(=O)c1cc(-c2cnn3ccccc23)c(Cl)s1] | 425 |
| N-[(cis)-4-amino-1,1-dioxidotetrahydro-2H-thiopyran-3-yl]-5-chloro-4-(pyrazolo[1,5-a]pyridin-3-yl) thiophene-2-carboxamide | 208 | 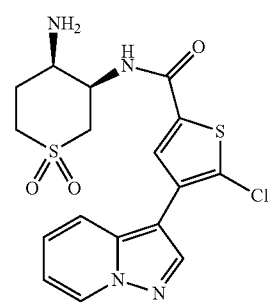 [SMILES: N[C@@H]1CCS(=O)(=O)C[C@@H]1NC(=O)c1cc(-c2cnn3ccccc23)c(Cl)s1] | 425 |
| N-[(trans)-3-amino-1,1-dioxidotetrahydro-2H-thiopyran-4-yl]-5-chloro-4-(pyrazolo[1,5-a]pyridin-3-yl) thiophene-2-carboxamide | 209 | 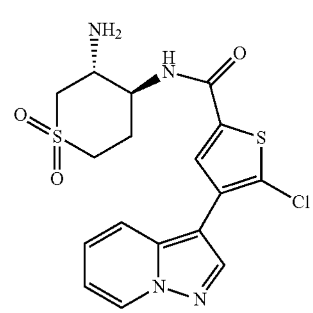 [SMILES: N[C@H]1CS(=O)(=O)CC[C@@H]1NC(=O)c1cc(-c2cnn3ccccc23)c(Cl)s1] | 425 |

-continued

| Name | Example # | Structure | LCMS M + H = |
|---|---|---|---|
| N-[(cis)-3-amino-1,1-dioxidotetrahydro-2H-thiopyran-4-yl]-5-chloro-4-(pyrazolo[1,5-a]pyridin-3-yl) thiophene-2-carboxamide | 210 | 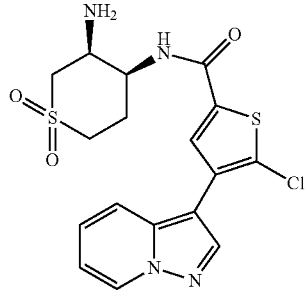 [SMILES: N[C@@H]1CS(=O)(=O)CC[C@@H]1NC(=O)c1cc(-c2cnn3ccccc23)c(Cl)s1] | 425 |

Example 211

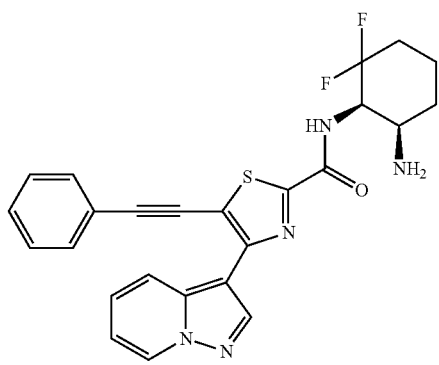 [SMILES: N[C@@H]1CCCC(F)(F)[C@@H]1NC(=O)c1nc(-c2cnn3ccccc23)c(C#Cc2ccccc2)s1]

N-[(1R,6R)-6-Amino-2,2-difluorocyclohexyl]-5-(phenylethynyl)-4-pyrazolo[1,5-a]pyridin-3-yl-1,3-thiazole-2-carboxamide (Scheme 7)

Synthesis began with an intermediate prepared from example 2 via the use of NBS to obtain compound 39 (Scheme 7). Compound 39 (40 mg, 0.072 mmol) was dissolved in dichloromethane (144 µL) and degassed and flushed with argon. Trans-bis(triphenylphosphine)palladium(II) chloride (10.09 mg, 0.014 mmol) and copper(I) iodide (2.74 mg, 0.014 mmol) were added, followed by triethyl amine (80 µL, 0.575 mmol) and phenyl acetylene (14.68 mg, 0.144 mmol). The reaction mixture was stirred at 50° C. Upon reaction completion, the reaction was diluted with water (10 mL) and dichloromethane (5 mL). The organic was dried over sodium sulfate and filtered through celite. After concentration, the residue was purified by column chromatography (10-30% acetone: hexanes, linear gradient). The isolated product was subject to deprotection (1:1 DCM: TFA-1 mL) at RT for 1 hr. Excess solvent was removed under reduced pressure purification was carried out via reverse phase chromatography (10-100% acetonitrile in water with 0.05% trifluoroacetic acid) to yield the desired product, compound 40 (20 mg, 47% yield) MS APCI: [M+H]$^+$ m/z 478. $^1$H NMR (600 MHz, DMSO-d$_6$): δ 8.84 (d, J=11.3, 1H), 7.66 (s, 1H), 7.50 (s, 2H), 4.10 (d, J=4.9, 3H), 3.32 (s, 1H), 2.48 (s, 16H), 2.19-1.36 (m, 5H), 1.21 (s, 2H).

The following examples were prepared in an analogous manner of that described in example 211 with the use of known or commercial functionalized terminal acetylenes.

| Name | Example # | Structure | LCMS M + H = |
|---|---|---|---|
| N-[(1R,6R)-6-Amino-2,2-difluorocyclohexyl]-5-(3-hydroxy-3-methylbut-1-yn-1-yl)-4-pyrazolo[1,5-a]pyridin-3-yl-1,3-thiazole-2-carboxamide | 212 | 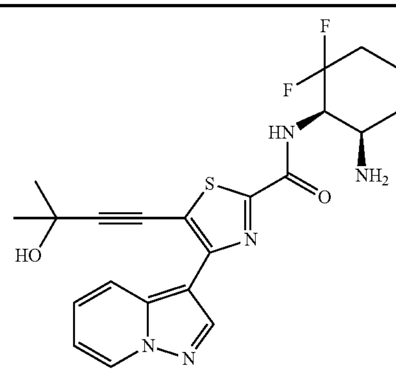 | 460 |

-continued

| Name | Example # | Structure | LCMS M + H = |
|------|-----------|-----------|--------------|
| N-[(1R,6R)-6-Amino-2,2-difluorocyclohexyl]-5-ethynyl-4-pyrazolo[1,5-a]pyridin-3-yl-1,3-thiazole-2-carboxamide | 213 | 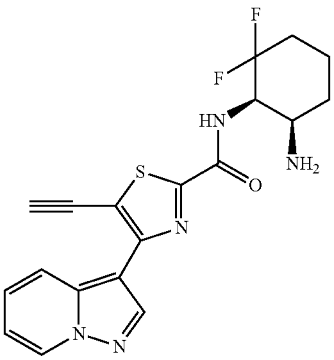 [SMILES: C#Cc1sc(C(=O)N[C@@H]2[C@H](N)CCCC2(F)F)nc1-c1cnn2ccccc12] | 401 |
| N-[(1R,6R)-6-Amino-2,2-difluorocyclohexyl]-5-(cyclopropylethynyl)-4-pyrazolo[1,5-a]pyridin-3-yl-1,3-thiazole-2-carboxamide | 214 | 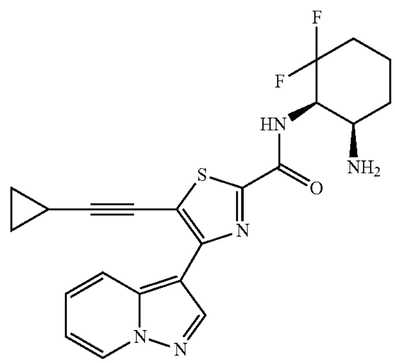 [SMILES: N[C@@H]1CCCC(F)(F)[C@@H]1NC(=O)c1nc(-c2cnn3ccccc23)c(C#CC2CC2)s1] | 442 |
| N-[(1R,6R)-6-Amino-2,2-difluorocyclohexyl]-5-(3-methoxyprop-1-yn-1-yl)-4-pyrazolo[1,5-a]pyridin-3-yl-1,3-thiazole-2-carboxamide | 215 | 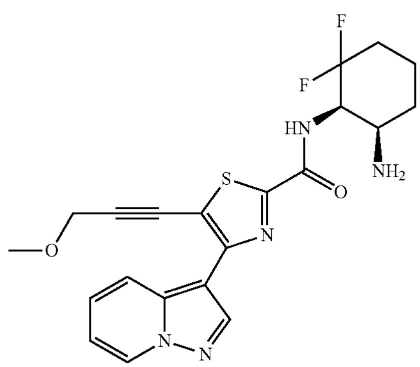 [SMILES: COCC#Cc1sc(C(=O)N[C@@H]2[C@H](N)CCCC2(F)F)nc1-c1cnn2ccccc12] | 446 |

Example 216

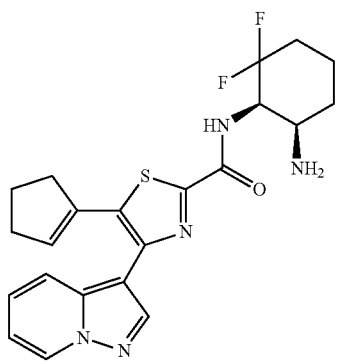 [SMILES: N[C@@H]1CCCC(F)(F)[C@@H]1NC(=O)c1nc(-c2cnn3ccccc23)c(C2=CCCC2)s1]

N-[(1R,6R)-6-amino-2,2-difluorocyclohexyl]-5-cyclopent-1-en-1-yl-4-pyrazolo[1,5-a]pyridin-3-yl-1,3-thiazole-2-carboxamide (Scheme 8)

Synthesis began with an intermediate prepared from example 2 via the use of NBS to obtain compound 39 (Scheme 8). Compound 39 (30 mg, 0.054 mmol) was dissolved in a solution of dioxane (245 µL) and water (24.51 pt) 280447-0082, to which cyclopent-1-en-1-ylboronic acid (9.05 mg, 0.081 mmol), tribasic potassium phosphate (19.46 mg, 0.092 mmol). The system degassed and flushed with argon three times before the addition of Pd₂dba₃ (4.94 mg, 5.39 mop and tricyclohexylphosphine (3.63 mg, 0.013 mmol), Again, the system was purged and flushed with argon three times before sealing and heating to 120° C. Upon completion, the reaction was diluted with water (5 mL) and dichloromethane (5 mL). The organic was dried over sodium sulfate and was concentrated before subjecting to purification by column chromatography (10-30% acetone in hexanes, linear gradient). The isolated product was subjected to deprotection by adding 1:1 dichloromethane:trifluoroacetic acid (1 mL) for 1 hr at ambient temperature. The reaction was concentrated under reduced pressure and subsequently purified by reverse phase chromatography (10-100% acetonitrile in water with 0.05% trifluoroacetic acid) to yield the desired product, compound 41 (15 mg, 50% yield). MS APCI: [M H]+ m/z 444. ¹H NMR (500 MHz, DMSO-d₆): δ 8.76 (d, J=7.0, 1H), 8.23 (s, 1H), 7.72 (d, J=8.9, 1H), 7.38-7.22 (m, 2H), 6.98 (t, J=6.7, 2H), 6.06 (s, 1H), 4.33 (d, J=20.3, 1H), 3.22 (d, J=102.5, 2H), 2.63-2.21 (m, 5H), 1.81 (tdd, J=85.6, 67.1, 28.5, 15H), 1.26-0.95 (m, 4H).

The following examples were prepared in an analogous manner of that described in example 216 with the use of known or commercial boronic acids and esters.

| Name | Example # | Structure | LCMS M + H = |
|---|---|---|---|
| N-[(1R,6S)-6-Amino-2,2-difluorocyclohexyl]-5-isopropenyl-4-pyrazolo[1,5-a]pyridin-3-yl-1,3-thiazole-2-carboxamide | 217 | 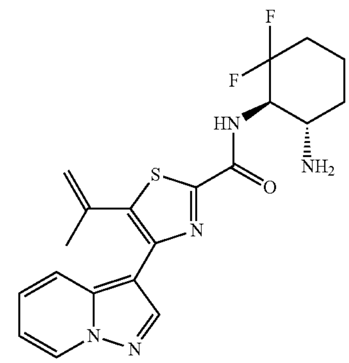 [SMILES: C=C(C)c1sc(C(=O)N[C@@H]2[C@@H](N)CCCC2(F)F)nc1-c1cnn2ccccc12] | 418 |
| N-[(1R,6S)-6-Amino-2,2-difluorocyclohexyl]-5-isopropenyl-4-[6-(trifluoromethyl)pyrazolo[1,5-a]pyridin-3-yl]-1,3-thiazole-2-carboxamide | 218 | | 486 |
| N-[(1R,6S)-6-Amino-2,2-difluorocyclohexyl]-4-pyrazolo[1,5-a]pyridin-3-yl-5-vinyl-1,3-thiazole-2-carboxamide | 219 | 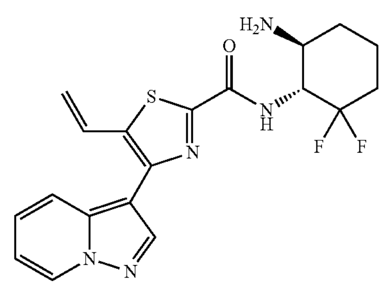 [SMILES: C=Cc1sc(C(=O)N[C@@H]2[C@@H](N)CCCC2(F)F)nc1-c1cnn2ccccc12] | 404 |
| N-[(1R,6S)-6-Amino-2,2-difluorocyclohexyl]-4-(6-fluoropyrazolo[1,5-a]pyridin-3-yl)-5-isopropenyl-1,3-thiazole-2-carboxamide | 220 | 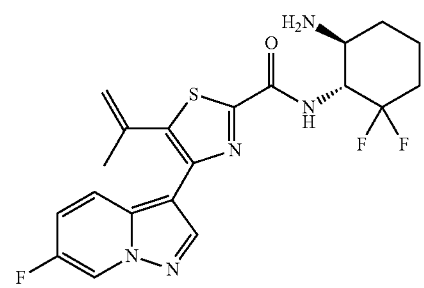 [SMILES: C=C(C)c1sc(C(=O)N[C@@H]2[C@@H](N)CCCC2(F)F)nc1-c1cnn2cc(F)ccc12] | 436 |

| Name | Example # | Structure | LCMS M + H = |
|---|---|---|---|
| N-[(1R,6R)-6-amino-2,2-difluorocyclohexyl]-5-[(1E)-but-1-en-1-yl]-4-pyrazolo[1,5-a]pyridin-3-yl-1,3-thiazole-2-carboxamide | 221 | 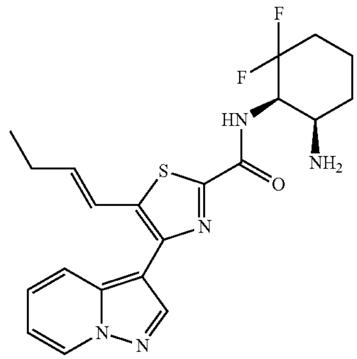 [SMILES: CC/C=C/c1sc(C(=O)N[C@@H]2[C@H](N)CCCC2(F)F)nc1-c1cnn2ccccc12] | 432 |
| N-[(1R,6R)-6-Amino-2,2-difluorocyclohexyl]-4-pyrazolo[1,5-a]pyridin-3-yl-5-vinyl-1,3-thiazole-2-carboxamide | 222 | 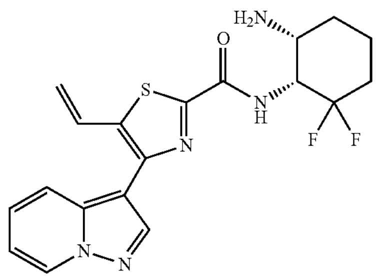 [SMILES: C=Cc1sc(C(=O)N[C@@H]2[C@H](N)CCCC2(F)F)nc1-c1cnn2ccccc12] | 403 |
| N-[(1R,6R)-6-amino-2,2-difluorocyclohexyl]-5-(2-methylprop-1-en-1-yl)-4-pyrazolo[1,5-a]pyridin-3-yl-1,3-thiazole-2-carboxamide | 223 | 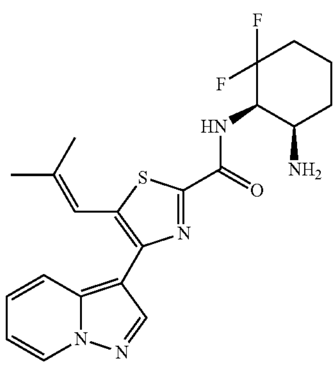 [SMILES: CC(C)=Cc1sc(C(=O)N[C@@H]2[C@H](N)CCCC2(F)F)nc1-c1cnn2ccccc12] | 432 |
| N-[(1R,6R)-6-amino-2,2-difluorocyclohexyl]-5-[(E)-2-cyclohexylvinyl]-4-pyrazolo[1,5-a]pyridin-3-yl-1,3-thiazole-2-carboxamide | 224 | 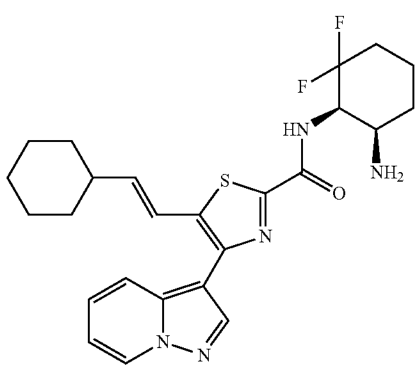 [SMILES: N[C@@H]1CCCC(F)(F)[C@@H]1NC(=O)c1nc(-c2cnn3ccccc23)c(/C=C/C2CCCCC2)s1] | 486 |

| Name | Example # | Structure | LCMS M + H = |
|---|---|---|---|
| N-[(1R,6R)-6-amino-2,2-difluorocyclohexyl]-5-[(E)-2-cyclopropylvinyl]-4-pyrazolo[1,5-a]pyridin-3-yl-1,3-thiazolo-2-carboxamide | 225 | 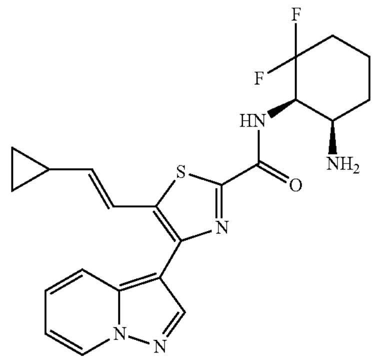 [SMILES: N[C@@H]1CCCC(F)(F)[C@@H]1NC(=O)c1nc(-c2cnn3ccccc23)c(/C=C/C2CC2)s1] | 444 |
| N-[(1R,6S)-6-amino-2,2-difluorocyclohexyl]-5-cyclopropyl-4-pyrazolo[1,5-a]pyridin-3-yl-1,3-thiazole-2-carboxamide | 226 | 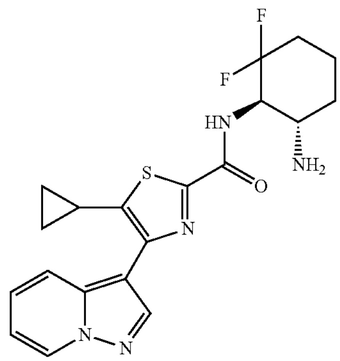 [SMILES: N[C@H]1CCCC(F)(F)[C@@H]1NC(=O)c1nc(-c2cnn3ccccc23)c(C2CC2)s1] | 418 |

Example 227

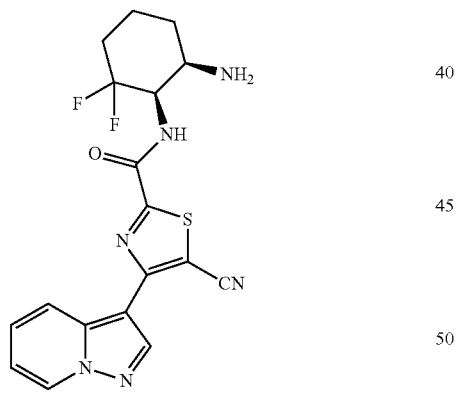

N-[(1R,6R)-6-amino-2,2-difluorocyclohexyl]-5-cyano-4-pyrazolo[1,5-a]pyridin-3-yl-1,3-thiazole-2-carboxamide (Scheme 9)

Synthesis began with intermediate prepared from example 2 via the use of NIS to obtain compound 42 (Scheme 9). Compound 42 (25.3 mg, 0.042 mmol) was added Cu(I) CN (11.3 mg, 0.13 mmol) and DMA (419 µL) in a microwave vial. The reaction was heated to 160° C. for 30 min by microwave irradiation. The reaction mixture was diluted with a saturated solution of ammonium chloride (5 mL) and dichloromethane (5 mL). The organic was washed with water (10 mL), then dried over sodium sulfate and concentrated under reduced pressure. The residue was subjected to deprotection by exposure to 1:1 trifluoroacetic acid:dichloromethane (1 mL). The reaction mixture was concentrated under reduced pressure and was purified by reverse phase chromatography (10-100% MeCN in water (0.05% trifluoroacetic acid), linear gradient) to yield the desired product (43, 14 mg, 0.035 mmol, 83% yield). MS APCI: [M+H]$^+$ m/z 402. $^1$H NMR (600 MHz, DMSO-d$_6$): δ 8.84 (d, J=11.3, 1H), 7.66 (s, 1H), 7.50 (s, 2H), 4.10 (d, J=4.9, 3H), 3.32 (s, 1H), 2.48 (s, 16H), 2.19-1.36 (m, 5H), 1.21 (s, 2H).

Example 228

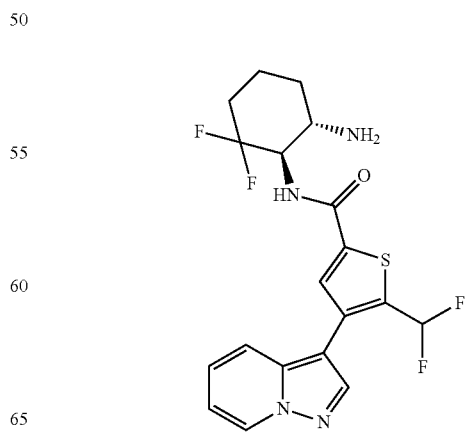

N-[(1R,6S)-6-amino-2,2-difluorocyclohexyl]-5-(difluoromethyl)-4-pyrazolo[1,5-a]pyridin-3-ylthiophene-2-carboxamide (Scheme 10)

The synthesis of compound 50 is carried out in three parts; A, B, and C (see scheme 10).

Part A, begins with a solution of compound 44 (4.8 g, 16.00 mmol) in THF (50 mL) at −40° C. (acetonitrile/dry ice bath) to which is added isopropylmagnesium chloride (8.80 ml, 17.60 mmol) dropwise. After 3 hrs at −40° C., N,N-dimethylformamide (3.72 ml, 48.0 mmol) was added to the reaction and the solution was warmed to room temperature. The reaction was diluted with water (100 mL) and partioned with ethyl acetate (50 mL). The organic was washed water (100 mL), then dried over sodium sulfate and concentrated to yield ~90% pure product (3.95 g, compound 45). The crude material (compound 45) (915 mg, 3.67 mmol) was dissolved in dichloromethane (1 mL) to this solution was added deoxofluor (1693 µL, 9.18 mmol). The reaction was stirred at ambient temperature for 8 hours and was diluted with water (5 mL). The solution was partioned with ethyl acetate and the organic was dried over sodium sulfate and was concentrated to dryness. The resulting residue was purified by column chromatography (0-10% ethyl acetate in hexanes, linear gradient) to yield compound 46 (84% yield, 838 mg). $^1$H NMR (500 MHz, CDCl$_3$) δ 8.54-8.44 (m, 0H), 8.03 (s, 1H), 7.65 (s, 1H), 7.62 (d, J=8.8, 1H), 6.89 (d, J=7.2, 1H), 6.72 (t, J=54.4, 1H), 6.20 (d, J=9.3, 1H), 4.37-4.06 (m, 1H), 2.80 (t, J=9.7, 1H), 2.31-2.20 (m, 1H), 2.10 (d, J=13.7, 1H), 1.92-1.73 (m, J=26.0, 13.5, 2H), 1.44-1.16 (m, 2H).

Part B begins with commercially available bromo-pyrazolopyrimidine 47 (755 mg, 3.83 mmol) and 4,4,5,5-tetramethyl-2-(propan-2-yloxy)-1,3,2-dioxaborolane (2.3 mL, 11.50 mmol) in THF (1.5 mL) at −78° C. To this solution was added n-butyllithium (4.8 mL, 7.66 mmol) dropwise over 10 minutes. The reaction was slowly warmed to room temperature and was poured into water (10 mL) and partitioned with dichloromethane (10 mL). The organic was dried over sodium sulfate and concentrated before purification by column chromatography (0-20% ethyl acetate in hexanes) to yield the boronic ester 48 (18% yield, 170 mg). $^1$H NMR (500 MHz, cdcl3) δ 8.54-8.44 (m, 0H), 8.03 (s, 1H), 7.65 (s, 1H), 7.62 (d, J=8.8, 1H), 6.89 (d, J=7.2, 1H), 6.72 (t, J=54.4, 1H), 6.20 (d, J=9.3, 1H), 4.37-4.06 (m, 1H), 2.80 (t, J=9.7, 1H), 2.31-2.20 (m, 1H), 2.10 (d, J=13.7, 1H), 1.92-1.73 (m, J=26.0, 13.5, 2H), 1.44-1.16 (m, 2H).

Step C combines the products from parts A and B. To a clean dry 1.5 ml microwave tube was added bromide 46 (142 mg, 0.522 mmol), boronic ester 48 (85 mg, 0.35 mmol), K$_3$PO$_4$ (126 mg, 0.59 mmol), Pd$_2$ dba$_3$ (31.9 mg, 0.035 mmol) and P(Cy)$_3$ (23.4 mg, 0.084 mmol). The system was degassed and charged with dioxane (1.5 mL) and water (0.15 mL) before heating 85° C. (8 hrs). The reaction was partitioned with water (5 mL) and dichloromethane (5 mL). The organic was dried over sodium sulfate and concentrated before purification by column chromatography (0-30% ethyl acetate in hexanes+10% dichloromethane) to yield the Suzuki adduct in 56% yield (60 mg). The isolated product (60 mg, 0.195 mmol) was dissolved in MeOH (2 mL) and KOH (0.389 ml, 0.389 mmol) was added. The reaction was heated to 60° C. and was stirred for 1 hr. The reaction was acidified with 2N HCl (5 mL) and was cooled to 0° C. The product was collected by filtration and was dried under reduced pressure to yield carboxylic acid 49 in 96% yield (55 mg). Compound 49 (25 mg, 0.085 mmol) was dissolved in DMF and DIPEA (14.84 µL, 0.085 mmol). To this solution was added added BOP (56.4 mg, 0.127 mmol) and intermediate 11 (21.26 mg, 0.085 mmol). The reaction was heated to 50° C. (8 hr). The crude reaction was purified on RP-gilson (10-100% acetonitrile in water+0.01% TFA). The isolated material was subjected to deprotection by treating with a 1:1 solution of dichloromethane:TFA (1 hr at RT). The reaction was concentrated under reduced pressure and was desalted by PS-bicarb plug to yield compound 50 (28% yield, 10 mg). MS APCI: [M+H]$^+$ m/z 427. $^1$H NMR (500 MHz, CDCl$_3$) δ 8.54-8.44 (m, 0H), 8.03 (s, 1H), 7.65 (s, 1H), 7.62 (d, J=8.8, 1H), 6.89 (d, J=7.2, 1H), 6.72 (t, J=54.4, 1H), 6.20 (d, J=9.3, 1H), 4.37-4.06 (m, 1H), 2.80 (t, J=9.7, 1H), 2.31-2.20 (m, 1H), 2.10 (d, J=13.7, 1H), 1.92-1.73 (m, J=26.0, 13.5, 2H), 1.44-1.16 (m, 2H).

Example 229

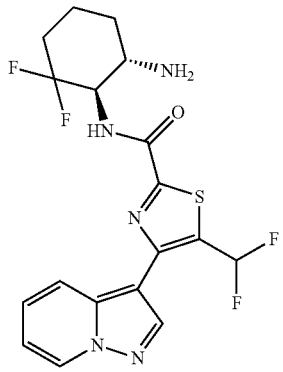 [SMILES: N[C@H]1CCCC(F)(F)[C@@H]1NC(=O)c1nc(-c2cnn3ccccc23)c(C(F)F)s1]

N-[(1R,6S)-6-Amino-2,2-difluorocyclohexyl]-5-(difluoromethyl)-4-(6-fluoropyrazolo[1,5-a]pyridin-3-yl)-1,3-thiazole-2-carboxamide (Scheme 11)

Synthesis began with material from the procedure outlined in example 221 (Compound 51). To compound 51 (65 mg, 0.101 mmol) was added tetrahydrofuran (673 µL), water (337 µL), N-methylmorpholine-N-oxide (17.74 mg, 0.151 mmol) and osmium tetraoxide in water (4%, 158 µL, 0.020 mmol). The reaction was stirred at ambient temperature for 8 hrs. Upon completion the reaction was quenched with 10% sodium thiosulfate solution (5 mL) and was extracted with dichloromethane (5 mL). The organic was washed with water (5 mL), dried over sodium sulfate and was concentrated to dryness. The crude dihydroxylated material was carried forward as an orange solid. Diol 52 was dissolved in water (210 µL) and THF (419 µL) and to this solution was added sodium periodate (16.13 mg, 0.075 mmol) at room temperature. After 2 hrs, the reaction was worked with 10% sodium thiosulfate solution (5 mL) and was extracted with dichloromethane (5 mL). The organic was dried over sodium sulfate and was concentrated to dryness. The crude aldehyde was carried forward.

To aldehyde 53 (31.9 mg, 0.049 mmol) in DCM (494 µL) was added deoxofluor (91 µL, 0.494 mmol). The reaction was stirred at room temperature for 8 hrs. Upon completion, the reaction, piperidine (98 µL, 0.988 mmol) was added to the reaction. The reaction was heated to 40° C. for 2 hours, after this time the reaction was diluted with water (10 mL) and dichloromethane (5 mL) and the organic was dried over sodium sulfate and concentrated to dryness. The resultant residue was purified by column chromatography (first, 20% EtOAc in hexanes, isocratic, then 10% MeOH in DCM: Hexanes, 10%-60% linear gradient) to yield the desired product 54. MS APCI: [M+H]$^+$ 446. $^1$H NMR (600 MHz, CDCl$_3$): δ 8.54-8.44 (m, 0H), 8.03 (s, 1H), 7.65 (s, 1H), 7.62 (d, J=8.8, 1H), 6.89 (d, J=7.2, 1H), 6.72 (t, J=54.4, 1H), 6.20 (d, J=9.3, 1H), 4.37-4.06 (m, 1H), 2.80 (t, J=9.7, 1H), 2.31-2.20 (m, 1H), 2.10 (d, J=13.7, 1H), 1.92-1.73 (m, J=26.0, 13.5, 2H), 1.44-1.16 (m, 2H).

The following examples were prepared in an analogous manner of that described in example 229.

| Name | Example # | Structure | LCMS M + H = |
|---|---|---|---|
| N-[(1R,6S)-6-Amino-2,2-difluorocyclohexyl]-5-(difluoromethyl)-4-[6-(trifluoromethyl)pyrazolo[1,5-a]pyridin-3-yl]-1,3-thiazole-2-carboxamide | 230 | | 496 |

Example 231

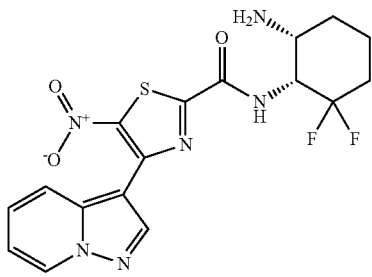

N-[(1R,6R)-6-Amino-2,2-difluorocyclohexyl]-5-nitro-4-pyrazolo[1,5-a]pyridin-3-yl-1,3-thiazole-2-carboxamide (Scheme 12)

Example 231 was prepared according to scheme 12 and commenced with compound 55, which was synthesized using the procedure outlined in example 2 with the exception of the Boc-deprotection step in Step E, part 3. To compound 55 (85 mg, 0.178 mmol) at 0° C. was added nitric acid (400 µL, 6.27 mmol), followed by sulfuric acid (55 µL, 1.03 mmol). The ice bath was removed and the reaction was warmed to room temperature. Upon completion the reaction was cooled to 0° C. and quenched with 5N NaOH and was portioned with dichloromethane. The organic was dried over sodium sulfate and was concentrated to dryness to yield compound 56 (73 mg, 0.17 mmol, 97% yield). MS APCI: [M+H]$^+$ m/z 423.0. $^1$H NMR (500 MHz, CDCl$_3$) δ 9.04 (s, 1H), 8.61 (d, 6.9, 1H), 8.41-8.34 (m, 1H), 8.28 (d, J=9.0, 1H), 7.44-7.37 (m, 1H), 7.04-6.98 (m, 1H), 4.42-4.31 (m, 1H), 3.41-3.34 (m, 1H), 2.29-2.18 (m, 1H). $^{19}$F NMR (470 MHz, CDCl$_3$) δ −95.70 (d, J=248.0, 1F), −108.79--109.75 (m, J=246.3, 1F).

Example 232

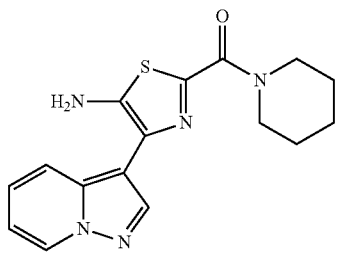 [SMILES: Nc1sc(C(=O)N2CCCCC2)nc1-c1cnn2ccccc12]

2-(Piperidin-1-ylcarbonyl)-4-pyrazolo[1,5-a]pyridin-3-yl-1,3-thiazol-5-amine (Scheme 13)

The synthesis of compound 61 was carried out according to scheme 13 beginning with commercially available pyrazolo[1,5-a]pyridine-3-carboxylic acid and by following the procedure outlined in example 1, part C, step 2 and subsequent steps though step E, part 1. The thiazole 5-position was left unfunctionalized by omitting part D, step 3 to obtain with the carboxylic acid 57. To carboxylic acid 57 (725 mg, 2.96 mmol) in DMF (30 mL) was added BOP (392 mg, 8.87 mmol) and piperidine (2.93 mL, 29.6 mmol). The reaction was stirred at ambient temperature for 48 hrs after which time the reaction was diluted with water and dichloromethane. The organic was washed with water before concentration. The resultant residue was purified by column chromatography (silica gel, 0-60% ethyl acetate in hexanes, linear gradient) to yield the piperidine amide (739 mg, 2.366 mmol, 80% yield). The amide (420 mg, 1.34 mmol) was dissolved in dichloromethane (1.3 mL) was treated with potassium nitrate (136 mg, 1.344 mmol) and sulfuric acid (215 µL, 4.03 mmol). The reaction mixture was stirred at RT until complete, as judged by LCMS analysis. The reaction was quenched with 1N potassium hydroxide in methanol, then diluted with water, before extracting with dichloromethane. The organic layer was evaporated to dryness and taken up in methanol. The product was collected by filtration and was dried under reduced pressure to yield compound 58 (225 mg, 0.630 mmol, 46.8% yield).

Compound 58 (225 mg, 0.630 mmol) was dissolved in ethanol (1.26 mL) was added to bomb charged ammonium formate (690 mg, 10.9 mmol) and Pd/C (670 mg, 0.32 mmol). The bomb was sealed and reaction was heated to 110° C. for ~2 hours behind a blast shield. The reaction was filtered through pad of celite (washed with methanol) and the filtrate was evaporated under reduced pressure. The resultant residue purified by column chromatography (silica gel, 0-15% methanol in dichloromethane, linear gradient) to yield compound 59 (163 mg, 0.498 mmol, 79% yield). MS APCI: [M+H]$^+$ m/z 328. $^1$H NMR (500 MHz, CD$_2$Cl$_2$) δ 8.50 (d, J=7.0, 1H), 8.23 (s, 1H), 7.94 (d, J=8.9, 1H), 7.24-7.16 (m, 1H), 6.86 (t, J=6.3, 1H), 4.40 (s, 2H), 3.68 (s, 2H), 1.70 (d, J=13.0, 6H).

Example 233

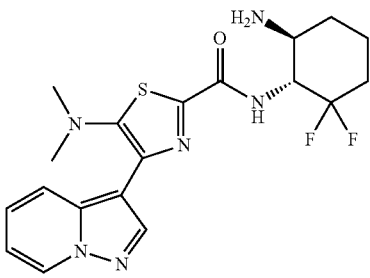 [SMILES: CN(C)c1sc(C(=O)N[C@@H]2[C@@H](N)CCCC2(F)F)nc1-c1cnn2ccccc12]

N-[(1R,6S)-6-Amino-2,2-difluorocyclohexyl]-5-(dimethylamino)-4-pyrazolo[1,5-a]pyridin-3-yl-1,3-thiazole-2-carboxamide (Scheme 13)

Synthesis began with compound 59, which was prepared by using the procedure in example 232, according to scheme 13. Alkylation of the thiazole amine 59 (29 mg, 0.089 mmol) was accomplished by adding tetrahydrofuran (1 mL) and cooling the reaction to 0° C. Sodium hydride (15 mg) was added to the reaction and the reaction was aged for 10 minutes at 0° C. Iodomethane (1 mL) was added dropwise and the reaction was slowly warmed to ambient temperature. Upon completion, as judged by LCMS, the reaction was diluted with water and dichloromethane. The organic was dried over sodium sulfate and was concentrated to dryness. The crude product was purified by column chromatography (0-80% EA/Hexanes) to yield the dimethylamine product (16 mg, 0.045 mmol). The material was subsequently saponified heating with 5N sodium hydroxide (200 µL) at 100° C. Upon completion, the reaction was cooled to 0° C. and the carboxylic acid 60 was collected by filtration (7.3 mg, 0.022 mmol, 49.7% yield).

Amide formation was accomplished by subjecting a solution of compound 60 (7.3 mg, 0.02 mmol) in DMF (290 µL) and DIPEA (5.86 µL, 0.034 mmol) to BOP (29.7 mg, 0.067 mmol), Fmoc-protected intermediate II (9.16 mg, 0.025 mmol). The reaction mixture was stirred at RT until complete by LC/MS analysis. The reaction was diluted with water (2 mL) and dichloromethane (500 µl). The organic layer was washed with water (2 mL), was dried over sodium sulfate and was concentrated under reduced pressure. The resulting residue was purified by column chromatography (silica gel, 20-50% ethyl acetate in hexanes, linear gradient) to yield the amide (14 mg, 0.022 mmol, 97% yield). The amide was subjected to deprotection by dissolving in DMF (218 µL) and adding piperidine (15 µL, 0.152 mmol). The reaction was stirred for ~3 hrs at room temperature before diluting with dichloromethane (1 mL) and water (2 mL). The organic was dried over sodium sulfate and was evaporated under reduced pressure. The crude product purified by column chromatography (silica gel, 0-30% ethyl acetate in hexanes, then 0-8% methanol:dichloromethane (1:9) in hexanes) to yield compound 61 (7.3 mg, 0.017 mmol, 80% yield). MS APCI: [M+H]+ m/z 421. $^1$H NMR (500 MHz, $CD_2Cl_2$) δ 8.50 (d, J=7.0, 1H), 8.46 (s, 1H), 8.09 (d, J=9.0, 1H), 7.34-7.27 (m, 1H), 7.27-7.22 (m, J=6.8, 1H), 6.88-6.83 (m, 1H), 4.19-4.12 (m, 0H), 2.93-2.84 (m, 0H), 2.80 (s, 5H), 2.29-2.19 (m, 1H), 2.09-2.02 (m, 1H), 1.88-1.77 (m, 2H). $^{19}$F NMR (470 MHz, $CD_2Cl_2$) δ −99.30 (d, J=241.5, 1F), −114.29−−115.29 (m, 1F).

What is claimed is:
1. A compound of formula I:

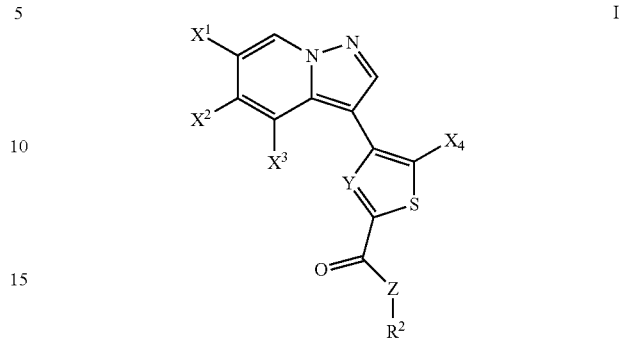

or a pharmaceutically acceptable salt or hydrate thereof; wherein:

Z is —N($R^1$)— or —O—;

$X^1$ is selected from the group consisting of: H, halogen, $C_{1-6}$alkyl, $C_{2-6}$alkenyl, $C_{3-6}$cycloalkyl, $CF_3$, methoxy, CN, CON($R^3$)$_2$, (trimethylsilyl)ethynyl, phenyl and a monocyclic or bicyclic ring system comprising up to 10 ring atoms, of which 1-3 are selected from N, O and S and the remainder are C, said phenyl and ring system bearing 0-3 substituents independently selected from halogen and $C_{1-4}$alkyl, optionally substituted with up to 3 halogen atoms;

$X^2$ is selected from the group consisting of: H, halogen, $C_{1-6}$alkyl, $C_{2-6}$alkenyl, $C_{3-6}$cycloalkyl, $CF_3$, methoxy, CN, CON($R^3$)$_2$, (trimethylsilyl)ethynyl, and phenyl bearing 0 to 5 halogen substituents;

$X^3$ is selected from the group consisting of: H, $OR^3$, N($R^3$)$_2$, $C_{1-6}$alkyl, $C_{2-6}$alkenyl, $C_{3-6}$cycloalkyl, $CF_3$, methoxy, CN, CON($R^3$)$_2$, (trimethylsilyl)ethynyl, and halogen;

$X^4$ is selected from the group consisting of: H, halogen, $C_{3-6}$cycloalkyl, $C_{1-6}$alkyl, $C_{2-6}$alkenyl, $C_{2-6}$alkynyl, $C_{3-6}$cycloalkenyl, —CN, nitro and N($R^3$)$_2$; said $C_{1-6}$alkyl optionally substituted with up to 3 halogen atoms and said $C_{2-6}$alkenyl and $C_{2-6}$alkynyl optionally substituted with up to 3 $R^5$ groups Y is selected from the group consisting of: N and CH;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:
(i) H;
(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and
(iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 4 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and —P(O)—($OR^3$)$_2$; where "aryl" refers to phenyl or 5- or 6-membered heteroaryl, either of which phenyl or heteroaryl is optionally fused to a 5- or 6-membered carbocycle or heterocycle, "Het" refers to a nonaromatic or partially aromatic mono- or bicyclic heterocyclic system of up to 10 ring atoms and $C_{3-10}$cycloalkyl and the cyclic portion of $C_{3-10}$cycloalkyl$C_{1-4}$alkyl may be fused with phenyl or a 5- or 6-membered heteroaryl;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each R3 independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino, or $R^3$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^3$ groups attached to the same atom may complete a heterocycle of up to 6 ring atoms which optionally bears up to 3 substituents independently selected from halogen, OH, oxo, CN, $CF_3$, $C_{1-4}$alkoxy, amino, $C_{1-4}$alkylamino and di($C_{1-4}$alkyl)amino;

$R^4$ has the same definition as $R^3$ except that $R^4$ is not H; and $R^5$ is selected from the group consisting of: phenyl, hydroxy, $C_{3-6}$cycloalkyl, and methoxy.

2. A compound according to claim 1 or a pharmaceutically acceptable salt or hydrate thereof, wherein:

Z is —N($R^1$)—;

$X^1$ is selected from the group consisting of: H, halogen, phenyl, and a monocyclic or bicyclic ring system comprising up to 10 ring atoms, of which 1-3 are selected from N, O and S and the remainder are C, said phenyl and ring system bearing 0-3 substituents independently selected from halogen and $C_{1-4}$alkyl, optionally substituted with up to 3 halogen atoms;

$X^2$ is selected from the group consisting of: H, halogen and phenyl bearing 0 to 5 halogen substituents;

$X^3$ is selected from the group consisting of: H, $OR^3$, N($R^3$)$_2$, $C_{1-6}$alkyl and halogen;

$X^4$ is selected from the group consisting of: H, halogen, $C_{3-6}$cycloalkyl and $C_{1-6}$alkyl, optionally substituted with up to 3 halogen atoms;

$R^2$ is selected from:

(i) H;

(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and (iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$; where "aryl" refers to phenyl or 5- or 6-membered heteroaryl, either of which phenyl or heteroaryl is optionally fused to a 5- or 6-membered carbocycle or heterocycle, and "Het" refers to a nonaromatic mono- or bicyclic heterocyclic system of up to 10 ring atoms;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each $R^3$ independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$-alkyl)amino, or $R^3$ represents phenyl, benzyl or 5- or 6-membered heteroaryl, any of which optionally bears up to 3 substituents independently selected from halogen, OH, CN, $CF_3$, $C_{1-4}$alkyl, $C_{1-4}$alkoxy, amino, $C_{1-4}$alkylamino and di($C_{1-4}$alkyl)amino;

or two $R^3$ groups attached to the same nitrogen atom may complete a heterocycle of up to 6 ring atoms which optionally bears up to 3 substituents independently selected from halogen, OH, oxo, CN, $CF_3$, $C_{1-4}$alkyl, $C_{1-4}$alkoxy, amino, $C_{1-4}$alkylamino and di($C_{1-4}$alkyl)amino; and $R^4$ has the same definition as $R^3$ except that $R^4$ is not H.

3. A compound according to claim 2 or a pharmaceutically acceptable salt or hydrate thereof, wherein Y is CH.

4. A compound according to claim 2 or a pharmaceutically acceptable salt or hydrate thereof, wherein Y is N.

5. A compound according to claim 2 or a pharmaceutically acceptable salt or hydrate thereof, wherein $X^1$ is phenyl bearing 0 to 3 halogen substituents.

6. A compound according to claim 2 or a pharmaceutically acceptable salt or hydrate thereof, wherein $X^1$ is H.

7. A compound according to claim 2 or a pharmaceutically acceptable salt or hydrate thereof, wherein $X^1$ is halogen.

8. A compound according to claim 2 or a pharmaceutically acceptable salt or hydrate thereof, wherein $X^1$ is 1-methyl-1H-pyrazol-4-yl.

9. A compound according to claim 2 or a pharmaceutically acceptable salt or hydrate thereof, wherein $X^3$ is H or methoxy.

10. A compound according to claim 2 or a pharmaceutically acceptable salt or hydrate thereof, wherein $X^4$ is H, halogen or methyl.

11. A compound according to claim 2 or a pharmaceutically acceptable salt or hydrate thereof, wherein $R^1$ is H.

12. A compound according to claim 2 or a pharmaceutically acceptable salt or hydrate thereof, wherein $R^2$ is $C_{3-10}$cycloalkyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

13. A compound according to claim 2 or a pharmaceutically acceptable salt or hydrate thereof, wherein $R^2$ is cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

14. A compound according to claim 2 or a pharmaceutically acceptable salt or hydrate thereof, wherein $R^2$ is $C_{1-8}$alkyl, which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents.

15. A compound according to claim 2 or a pharmaceutically acceptable salt or hydrate thereof, wherein:

$X^1$ is selected from the group consisting of H, halogen, phenyl bearing 0 to 3 halogen substituents and 1-methyl-1H-pyrazol-4-yl;

$X^3$ is H or methoxy;

$X^4$ is H, halogen or methyl;

$R^1$ is H; and $R^2$ is selected from the group consisting of:
(i) $C_{1-8}$alkyl, which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and
(ii) cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

16. A compound selected from the group consisting of:
N-[(1R,6R)-6-amino-2,2-difluorocyclohexyl]-5-chloro-4-[6-fluorophenyl)pyrazolo[1,5-a]pyridin-3-yl]-1,3-thiazole-2-carboxamide;
N-[(1R,6R)-6-amino-2,2-difluorocyclohexyl]-5-chloropyrazolo{1,5-a]pyridine-3-yl-1,3-thiazole-2-carboxamide;
N-(2-amino-3,3,3-trifluoro-1-phenylpropyl)-5-chloro-4-pyrazolo[1,5-a]pyridin-3-yl-1,3-thiazole-2-carboxamide;
N-[(1R,2R)-2-amino-1,2-diphenylethyl]-5-chloro-4-pyrazolo[1,5-a]pyridin-3-yl-1,3-thiazole-2-carboxamide;
5-chloro-4-pyrazolo[1,5-a]pyridin-3-yl-1,3-N-(2,2,2-trifluoroethyl)-1,3-thiazole-2-carboxamide;
N-[2-amino-1-phenylethyl]-5-chloro-4-pyrazolo[1,5-a]pyridin-3-yl-1,3-thiazole-2-carboxamide;
N-[(1R,6S)-6-amino-2,2-difluorocyclohexyl]-5-chloro-4-pyrazolo[1,5-a]pyridin-3-yl-1,3-thiazole-2-carboxamide;
N-[(1R,6R)-6-amino-2,2-difluorocyclohexyl]-5-bromo-4-pyrazolo[1,5-a]pyridin-3-yl-1,3-thiazole-2-carboxamide;
N-[(1R,6R)-6-amino-2,2-difluorocyclohexyl]-5-chloro-4-fluoropyrazolo{1,5-a]pyridine-3-yl-1,3-thiazole-2-carboxamide;
N-[(1R,6S)-6-amino-2,2-difluorocyclohexyl]-5-chloro-4-fluoropyrazolo{1,5-a]pyridine-3-yl-1,3-thiazole-2-carboxamide;
N-[(1R,6R)-6-amino-2,2-difluorocyclohexyl]-5-methyl-pyrazolo{1,5-a]pyridine-3-yl-1,3-thiazole-2-carboxamide;
N-[(1R,6R)-6-amino-2,2-difluorocyclohexyl]-4-(4-fluoropyrazolo[1,5-a]pyridin-3-yl)-5-methyl-1,3-thiazole-2-carboxamide;
N-[(1R,6R)-6-amino-2,2-difluorocyclohexyl]-4-(6-chloropyrazolo[1,5-a]pyridin-3-yl)-5-methyl-1,3-thiazole-2-carboxamide;
N-[(1R,6R)-6-amino-2,2-difluorocyclohexyl]-4-(6-bromopyrazolo[1,5-a]pyridin-3-yl)-5-methyl-1,3-thiazole-2-carboxamide;
N-[(1R,2R)-2-amino-1,2-diphenylethyl]-5-methyl-4-pyrazolo[1,5-a]pyridin-3-yl]-1,3-thiazole-2-carboxamide;
N-[(cis)-2-aminocyclohexyl]-5-methyl-4-pyrazolo[1,5-a]pyridin-3-yl]-1,3-thiazole-2-carboxamide;
N-[(cis)-2-aminocyclohexyl]-5-methyl-4-[6-(1-methyl-1H-pyrazol-4-yl)pyrazolo[1,5-a]pyridin-3-yl]-1,3-thiazole-2-carboxamide;
N-(2-amino-1-phenylethyl)-5-methyl-4-[6-(1-methyl-1H-pyrazol-4-yl)pyrazolo[1,5-a]pyridin-3-yl]-1,3-thiazole-2-carboxamide;
N-[(1S,2S)-2-amino-1,2-diphenyl]-5-methyl-4-[6-(1-methyl-1H-pyrazol-4-yl)pyrazolo[1,5-a]pyridin-3-yl]-1,3-thiazole-2-carboxamide;
N-[(1R,6R)-6-amino-2,2-difluorocyclohexyl]-5-methyl-4-[6-(1-methyl-1H-pyrazol-4-yl)pyrazolo[1,5-a]pyridin-3-yl]-1,3-thiazole-2-carboxamide;
N-[(1S)-2-hydroxy-1-phenylethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(2-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(3-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(3-chloro-5-fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(4-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(3-fluorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(1S)-1-(4-chlorophenyl)-2-hydroxyethyl]-5-methyl-4-[6-(1-methyl-1H-pyrazol-4-yl)pyrazolo[1,5-a]pyridin-3-yl]-1,3-thiazole-2-carboxamide;
N-[(cis)-2-aminocyclohexyl]-4-(4-methoxy-6-[phenylpyrazolo{1,5-a]pyridine-3-yl)-2-thiophenecarboxamide;
N-[(1R,6R)-6-amino-2,2-difluorocyclohexyl]-4-methoxy-6-phenylpyrazolo[1,5-a]pyridin-3-yl]-2-thiophenecarboxamide;
4-(4-methoxy-6-(1-methyl-1H-pyrazol-4-yl)pyrazolo[1,5-a]pyridin-3-yl]-2-thiophenecarboxamide;
N-[(1S)-2-hydroxy-1-phenylethyl]-4-methoxy-6-phenylpyrazolo[1,5-a]pyridin-3-yl]-2-thiophenecarboxamide;
N-[(1S)-2-hydroxy-1-phenylethyl]-4-methoxy-6-(1-methyl-1H-pyrazol-4-yl)pyrazolo[1,5-a]pyridin-3-yl]-2-thiophenecarboxamide;
N-[(1R,6R)-6-amino-2,2-difluorocyclohexyl]-4-[6-fluorophenyl)pyrazolo[1,5-a]pyridin-3-yl]-5-methyl-2-thiophenecarboxamide;
N-(3-amino-4,4,4-trifluorobutyl)-4-(4-methoxy-6-phenylpyrazolo[1,5-a]pyridin-3-yl]-2-thiophenecarboxamide;
N-[(cis)-2-aminocyclohexyl]-4-pyrazolo[1,5-a]pyridin-3-yl]-2-thiophenecarboxamide; and
N-[(1R,6R)-6-amino-2,2-difluorocyclohexyl]-5-chloro-4-pyrazolo[1,5-a]pyridin-3-yl-2-thiophenecarboxamide;
or a pharmaceutically acceptable salt of any of the foregoing compounds.

17. A compound selected from the group consisting of:
{4-[(5-Chloro-4-pyrazolo[1,5-a]pyridin-3-yl-1,3-thiazol-2-yl)carbonyl]piperazin-2-yl}methanol;
3-(5-Chloro-2-{[2-(difluoromethyl)piperazin-1-yl]carbonyl}-1,3-thiazol-4-yl)pyrazolo[1,5-a]pyridine;
{4-[(5-Chloro-4-pyrazolo[1,5-a]pyridin-3-yl-1,3-thiazol-2-yl)carbonyl]morpholin-3-yl}methanol;
5-Chloro-N-(4-hydroxy-1,1-dioxidotetrahydro-3-thienyl)-4-pyrazolo[1,5-a]pyridin-3-yl-1,3-thiazole-2-carboxamide;
3-(5-Chloro-2-{[2-(trifluoromethyl)piperazin-1-yl]carbonyl}-1,3-thiazol-4-yl)pyrazolo[1,5-a]pyridine;
(3R,4R)-1-[(5-Chloro-4-pyrazolo[1,5-a]pyridin-3-yl-1,3-thiazol-2-yl)carbonyl]-3-fluoropiperidin-4-amine;
(3S,4R)-1-[(5-Chloro-4-pyrazolo[1,5-a]pyridin-3-yl-1,3-thiazol-2-yl)carbonyl]-3-fluoropiperidin-4-amine;

N-[(3R,4R)-4-amino-1-benzylpyrrolidin-3-yl]-5-chloro-4-pyrazolo[1,5-a]pyridin-3-yl-1,3-thiazole-2-carboxamide;
2-[(5-Chloro-4-pyrazolo[1,5-a]pyridin-3-yl-1,3-thiazol-2-yl)carbonyl]-2,3-dihydro-1H-spiro[isoquinoline-4,4'-piperidine];
5-Chloro-N-[(4-phenylpiperidin-4-yl)methyl]-4-pyrazolo[1,5-a]pyridin-3-yl-1,3-thiazole-2-carboxamide;
5-Chloro-N-(2,3-dihydrospiro[indene-1,4'-piperidin]-3-yl)-4-pyrazolo[1,5-a]pyridin-3-yl-1,3-thiazole-2-carboxamide;
5-Chloro-N-[(3S)-1-methylpyrrolidin-3-yl]-4-pyrazolo[1,5-a]pyridin-3-yl-1,3-thiazole-2-carboxamide;
5-Chloro-4-pyrazolo[1,5-a]pyridin-3-yl-N-(1,2,3,4-tetrahydroisoquinolin-1-ylmethyl)-1,3-thiazole-2-carboxamide;
{3-Amino-1-[(5-chloro-4-pyrazolo[1,5-a]pyridin-3-yl-1,3-thiazol-2-yl)carbonyl]pyrrolidin-3-yl}methanol;
5-Chloro-N-piperidin-3-yl-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]pyrrolidin-3-amine;
3-[5-Chloro-2-(piperazin-1-ylcarbonyl)-1,3-thiazol-4-yl]pyrazolo[1,5-a]pyridine;
N-(2-Aminoethyl)-5-chloro-N-methyl-4-pyrazolo[1,5-a]pyridin-3-yl-1,3-thiazole-2-carboxamide;
N-(2-Aminoethyl)-5-chloro-N-ethyl-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]-N-methylpyrrolidin-3-amine;
3-{5-Chloro-2-[(2-methylpiperazin-1-yl)carbonyl]-1,3-thiazol-4-yl}pyrazolo[1,5-a]pyridine;
N-[(1-Aminocyclopentyl)methyl]-5-chloro-4-pyrazolo[1,5-a]pyridin-3-yl-1,3-thiazole-2-carboxamide;
N-[(1-Aminocyclohexyl)methyl]-5-chloro-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]-1,2,3,4-tetrahydroquinolin-3-amine;
N-(2-Amino-2-phenylethyl)-5-chloro-4-pyrazolo[1,5-a]pyridin-3-yl-1,3-thiazole-2-carboxamide;
N-(2-Aminoethyl)-5-chloro-4-pyrazolo[1,5-a]pyridin-3-yl-1,3-thiazole-2-carboxamide;
5-Chloro-4-pyrazolo[1,5-a]pyridin-3-yl-N-pyrrolidin-3-yl-1,3-thiazole-2-carboxamide;
3-{5-Chloro-2-[(3-methylpiperazin-1-yl)carbonyl]-1,3-thiazol-4-yl}pyrazolo[1,5-a]pyridine;
N-(3-Aminocyclohexyl)-5-chloro-4-pyrazolo[1,5-a]pyridin-3-yl-1,3-thiazole-2-carboxamide;
3-{5-Chloro-2-[(3-methylpiperazin-1-yl)carbonyl]-1,3-thiazol-4-yl}pyrazolo[1,5-a]pyridine;
N-(3-Aminocyclohexyl)-5-chloro-4-pyrazolo[1,5-a]pyridin-3-yl-1,3-thiazole-2-carboxamide;
1-{1-[(5-Chloro-4-pyrazolo[1,5-a]pyridin-3-yl-1,3-thiazol-2-yl)carbonyl]-4-phenylpiperidin-4-yl}methanamine;
N-(4-Amino-1,1-dioxidotetrahydro-3-thienyl)-5-chloro-4-pyrazolo[1,5-a]pyridin-3-yl-1,3-thiazole-2-carboxamide;
N-(2-Amino-2-methylpropyl)-5-chloro-4-pyrazolo[1,5-a]pyridin-3-yl-1,3-thiazole-2-carboxamide;
5-Chloro-N-(2-oxopiperidin-3-yl)-4-pyrazolo[1,5-a]pyridin-3-yl-1,3-thiazole-2-carboxamide;
N-[(1S,2R)-2-aminocyclopentyl]-5-chloro-4-pyrazolo[1,5-a]pyridin-3-yl-1,3-thiazole-2-carboxamide;
N-[(1-aminocycloheptyl)methyl]-5-chloro-4-pyrazolo[1,5-a]pyridin-3-yl-1,3-thiazole-2-carboxamide;
N-[(1R,6S)-6-Amino-2,2-difluorocyclohexyl]-5-chloro-4-pyrazolo[1,5-a]pyridin-3-yl-1,3-thiazole-2-carboxamide;
5-Chloro-N-(1-methyl-2-oxopyrrolidin-3-yl)-4-pyrazolo[1,5-a]pyridin-3-yl-1,3-thiazole-2-carboxamide;
5-Chloro-N-(3,3-difluorocyclopentyl)-4-pyrazolo[1,5-a]pyridin-3-yl-1,3-thiazole-2-carboxamide;
N-(2-Azetidin-1-yl-3,3,3-trifluoropropyl)-5-chloro-4-pyrazolo[1,5-a]pyridin-3-yl-1,3-thiazole-2-carboxamide;
3-[5-Chloro-2-(morpholin-4-ylcarbonyl)-1,3-thiazol-4-yl]pyrazolo[1,5-a]pyridine;
3-{5-Chloro-2-[(2,6-dimethylmorpholin-4-yl)carbonyl]-1,3-thiazol-4-yl}pyrazolo[1,5-a]pyridine;
3-{5-Chloro-2-[(4-methylpiperazin-1-yl)carbonyl]-1,3-thiazol-4-yl}pyrazolo[1,5-a]pyridine;
5-Chloro-N-(2-morpholin-4-ylethyl)-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]piperidin-4-ol;
1-[(5-Chloro-4-pyrazolo[1,5-a]pyridin-3-yl-1,3-thiazole-2-yl)carbonyl]-N,N-dimethylpiperidin-4-amine;
5-Chloro-N-[1-(hydroxymethyl)-2-methylpropyl]-4-pyrazolo[1,5-a]pyridin-3-yl-1,3-thiazole-2-carboxamide;
Diethyl {1-[(5-chloro-4-pyrazolo[1,5-a]pyridin-3-yl-1,3-thiazole-2-yl)carbonyl]piperidin-4-yl}phosphonate;
5-Chloro-N-(2-hydroxycyclopentyl)-4-pyrazolo[1,5-a]pyridin-3-yl-1,3-thiazole-2-carboxamide;
5-Chloro-N-(2,3-dihydroxypropyl)-N-methyl-4-pyrazolo[1,5-a]pyridin-3-yl-1,3-thiazole-2-carboxamide;
5-Chloro-N-(2-hydroxy-2-methylpropyl)-4-pyrazolo[1,5-a]pyridin-3-yl-1,3-thiazole-2-carboxamide;
1-[(5-Chloro-4-pyrazolo[1,5-a]pyridin-3-yl-1,3-thiazol-2-yl)carbonyl]-N,N-dimethylpiperidin-3-amine;
5-Chloro-N-(2-oxopyrrolidin-3-yl)-4-pyrazolo[1,5-a]pyridin-3-yl-1,3-thiazole-2-carboxamide;
5-Chloro-N-[(3R)-1-isopropylpyrrolidin-3-yl]-4-pyrazolo[1,5-a]pyridin-3-yl-1,3-thiazole-2-carboxamide;
5-Chloro-N-[(3S)-1-isopropylpyrrolidin-3-yl]-4-pyrazolo[1,5-a]pyridin-3-yl-1,3-thiazole-2-carboxamide;
5-Chloro-N-[2-(dimethylamino)-3,3,3-trifluoropropyl]-4-pyrazolo[1,5-a]pyridin-3-yl-1,3-thiazole-2-carboxamide;
5-Chloro-4-pyrazolo[1,5-a]pyridin-3-yl-N-[3,3,3-trifluoro-2-(3-fluoroazetidin-1-yl)propyl]-1,3-thiazole-2-carboxamide;
5-Chloro-N-(4-hydroxy-1,1-dioxidotetrahydro-3-thienyl)-4-pyrazolo[1,5-a]pyridin-3-yl-1,3-thiazole-2-carboxamide;
(2S)-2-Anilino-2-phenylethyl 5-chloro-4-pyrazolo[1,5-a]pyridin-3-yl-1,3-thiazole-2-carboxylate;
(2S)-2-Anilinopropyl 5-chloro-4-pyrazolo[1,5-a]pyridin-3-yl-1,3-thiazole-2-carboxylate;
5-Chloro-N-[(1S)-2-hydroxy-1-methylethyl]-N-phenyl-4-pyrazolo[1,5-a]pyridin-3-yl-1,3-thiazole-2-carboxamide;
5-Chloro-N-phenyl-4-pyrazolo[1,5-a]pyridin-3-yl-N-(2,2,2-trifluoroethyl)-1,3-thiazole-2-carboxamide;
5-Chloro-N-isopropyl-4-pyrazolo[1,5-a]pyridin-3-yl-1,3-thiazole-2-carboxamide;
5-Chloro-N-ethyl-N-methyl-4-pyrazolo[1,5-a]pyridin-3-yl-1,3-thiazole-2-carboxamide;
5-Chloro-N-(2-hydroxyethyl)-4-pyrazolo[1,5-a]pyridin-3-yl-1,3-thiazole-2-carboxamide;
5-Chloro-N-ethyl-4-pyrazolo[1,5-a]pyridin-3-yl-1,3-thiazole-2-carboxamide;

5-Chloro-N-(2-methoxyethyl)-4-pyrazolo[1,5-a]pyridin-3-yl-1,3-thiazole-2-carboxamide;
3-[5-Chloro-2-(piperidin-1-ylcarbonyl)-1,3-thiazol-4-yl]pyrazolo[1,5-a]pyridine;
5-Chloro-4-pyrazolo[1,5-a]pyridin-3-yl-N-pyridin-3-yl-1,3-thiazole-2-carboxamide;
5-Chloro-N-cyclohexyl-4-pyrazolo[1,5-a]pyridin-3-yl-1,3-thiazole-2-carboxamide;
N-Benzyl-5-chloro-4-pyrazolo[1,5-a]pyridin-3-yl-1,3-thiazole-2-carboxamide;
5-Chloro-4-pyrazolo[1,5-a]pyridin-3-yl-N-(pyridin-3-ylmethyl)-1,3-thiazole-2-carboxamide;
5-Chloro-4-pyrazolo[1,5-a]pyridin-3-yl-N-(2-thienylmethyl)-1,3-thiazole-2-carboxamide;
5-Chloro-4-pyrazolo[1,5-a]pyridin-3-yl-N-(2-pyrrolidin-1-ylethyl)-1,3-thiazole-2-carboxamide;
5-Chloro-1-(2,6-dimethylphenyl)-4-pyrazolo[1,5-a]pyridin-3-yl-1,3-thiazole-2-carboxamide;
3-{2-[(4-Acetylpiperazin-1-yl)carbonyl]-5-chloro-1,3-thiazol-4-yl}pyrazolo[1,5-a]pyridine;
5-Chloro-N-(3-phenylpropyl)-4-pyrazolo[1,5-a]pyridin-3-yl-1,3-thiazole-2-carboxamide;
5-Chloro-N-(3-chlorobenzyl)-4-pyrazolo[1,5-a]pyridin-3-yl-1,3-thiazole-2-carboxamide;
5-Chloro-4-pyrazolo[1,5-a]pyridin-3-yl-N-quinolin-7-yl-1,3-thiazole-2-carboxamide;
5-Chloro-4-pyrazolo[1,5-a]pyridin-3-yl-N-[4-(trifluoromethyl)benzyl]-1,3-thiazole-2-carboxamide;
3-{2-[(4-Benzylpiperidin-1-yl)carbonyl]-5-chloro-1,3-thiazol-4-yl}pyrazolo[1,5-a]pyridine;
3-(5-Chloro-2-{[4-(3-methoxyphenyl)piperazin-1-yl]carbonyl}-1,3-thiazol-4-yl)pyrazolo[1,5-a]pyridine;
5-Chloro-N-ethyl-N-phenyl-4-pyrazolo[1,5-a]pyridin-3-yl-1,3-thiazole-2-carboxamide;
5-Chloro-N-isopropyl-N-phenyl-4-pyrazolo[1,5-a]pyridin-3-yl-1,3-thiazole-2-carboxamide;
N-(2-Anilinocyclohexyl)-5-chloro-4-pyrazolo[1,5-a]pyridin-3-yl-1,3-thiazole-2-carboxamide;
5-Chloro-N-methyl-N-(3-methylphenyl)-4-pyrazolo[1,5-a]pyridin-3-yl-1,3-thiazole-2-carboxamide;
3-(5-Chloro-2-{[3-(methylsulfonyl)pyrrolidin-1-yl]carbonyl}-1,3-thiazol-4-yl)pyrazolo[1,5-a]pyridine;
N-[(1R)-1-(Aminomethyl)-2,2,2-trifluoroethyl]-5-chloro-4-pyrazolo[1,5-a]pyridin-3-yl-1,3-thiazole-2-carboxamide;
N-(2-Aminoethoxy)-5-chloro-4-pyrazolo[1,5-a]pyridin-3-yl-1,3-thiazole-2-carboxamide;
N-[(1S)-1-(Aminomethyl)-2,2,2-trifluoroethyl]-5-chloro-4-pyrazolo[1,5-a]pyridin-3-yl-1,3-thiazole-2-carboxamide;
5-Chloro-N-(2-hydroxyethoxy)-4-pyrazolo[1,5-a]pyridin-3-yl-1,3-thiazole-2-carboxamide;
N-(2-Anilinocyclohexyl)-5-chloro-4-pyrazolo[1,5-a]pyridin-3-yl-1,3-thiazole-2-carboxamide;
5-Chloro-N-(2,4-difluorophenyl)-N-methyl-4-pyrazolo[1,5-a]pyridin-3-yl-1,3-thiazole-2-carboxamide;
5-Chloro-N-(2,5-difluorophenyl)-N-methyl-4-pyrazolo[1,5-a]pyridin-3-yl-1,3-thiazole-2-carboxamide;
5-Chloro-N-(2,3-difluorophenyl)-N-methyl-4-pyrazolo[1,5-a]pyridin-3-yl-1,3-thiazole-2-carboxamide;
5-Chloro-N-(4-chlorophenyl)-N-methyl-4-pyrazolo[1,5-a]pyridin-3-yl-1,3-thiazole-2-carboxamide;
N-(3-Aminophenyl)-5-chloro-N-methyl-4-pyrazolo[1,5-a]pyridin-3-yl-1,3-thiazole-2-carboxamide;
5-Chloro-N-methyl-N-(4-methylphenyl)-4-pyrazolo[1,5-a]pyridin-3-yl-1,3-thiazole-2-carboxamide;
5-Chloro-N-methyl-4-pyrazolo[1,5-a]pyridin-3-yl-N-pyridin-2-yl-1,3-thiazole-2-carboxamide;
5-Chloro-N-(2,6-difluorophenyl)-N-methyl-4-pyrazolo[1,5-a]pyridin-3-yl-1,3-thiazole-2-carboxamide;
5-Chloro-N-methyl-N-(3-methylphenyl)-4-pyrazolo[1,5-a]pyridin-3-yl-1,3-thiazole-2-carboxamide;
5-Chloro-4-pyrazolo[1,5-a]pyridin-3-yl-N-(2,2,2-trifluoroethyl)-1,3-thiazole-2-carboxamide;
5-Chloro-N-(3-hydroxyphenyl)-N-methyl-4-pyrazolo[1,5-a]pyridin-3-yl-1,3-thiazole-2-carboxamide;
N-[(1R,6R)-2-Aminocyclohexyl]-5-chloro-4-[(6-trifluoromethyl)pyrazolo[1,5-a]pyridin-3-yl]-1,3-thiazole-2-carboxamide;
5-Chloro-N-(2-chlorophenyl)-N-methyl-4-pyrazolo[1,5-a]pyridin-3-yl-1,3-thiazole-2-carboxamide;
5-Chloro-N-methyl-N-(2-methylphenyl)-4-pyrazolo[1,5-a]pyridin-3-yl-1,3-thiazole-2-carboxamide;
5-Chloro-N-(4-fluorophenyl)-N-methyl-4-pyrazolo[1,5-a]pyridin-3-yl-1,3-thiazole-2-carboxamide;
5-Chloro-N-(3-chlorophenyl)-N-methyl-4-pyrazolo[1,5-a]pyridin-3-yl-1,3-thiazole-2-carboxamide;
5-Chloro-N-(3-fluorophenyl)-N-methyl-4-pyrazolo[1,5-a]pyridin-3-yl-1,3-thiazole-2-carboxamide;
N-[(1S,6S)-2-Aminocyclohexyl]-5-chloro-4-[(6-trifluoromethyl)pyrazolo[1,5-a]pyridin-3-yl]-1,3-thiazole-2-carboxamide;
5-Chloro-N-(2-chlorophenyl)-N-methyl-4-pyrazolo pyridin-3-yl-1,3-thiazole-2-carboxamide;
{4-[(5-Chloro-4-pyrazolo[1,5-a]pyridin-3-yl-1,3-thiazol-2-yl)carbonyl]morpholin-2-yl}methanol;
1-[(5-Chloro-4-pyrazolo[1,5-a]pyridin-3-yl-1,3-thiazol-2-yl)carbonyl]-2,3,4,5-tetrahydro-1H-1,4-benzodiazepine;
5-Chloro-N-(3-fluorophenyl)-N-methyl-4-pyrazolo[1,5-a]pyridin-3-yl-1,3-thiazole-2-carboxamide;
N-[1-(Aminomethyl)-6-fluoro-2,3-dihydro-1H-inden-1-yl]-5-chloro-4-pyrazolo[1,5-a]pyridin-3-yl-1,3-thiazole-2-carboxamide;
5-Chloro-N-methyl-N-phenyl-4-pyrazolo[1,5-a]pyridin-3-yl-1,3-thiazole-2-carboxamide;
N-[(1R,6S)-6-amino-2,2-difluorocyclohexyl]-4-pyrazolo[1,5-a]pyridin-3-yl-1,3-thiazole-2-carboxamide;
3-[2-(Piperidin-1-ylcarbonyl)-1,3-thiazol-4-yl]pyrazolo[1,5-a]pyridine;
N-[1-(Aminomethyl)-5-fluoro-2,3-dihydro-1H-inden-1-yl]-5-chloro-4-pyrazolo[1,5-a]pyridin-3-yl-1,3-thiazole-2-carboxamide;
N-[1-(Aminomethyl)-4-fluoro-2,3-dihydro-1H-inden-1-yl]-5-chloro-4-pyrazolo[1,5-a]pyridin-3-yl-1,3-thiazole-2-carboxamide;
N-[1-(Aminomethyl)-2,3-dihydro-1H-inden-1-yl]-5-chloro-4-pyrazolo[1,5-a]pyridin-3-yl-1,3-thiazole-2-carboxamide;
N-(2-Amino-3,3,3-trifluoro-1-phenylpropyl)-5-chloro-4-pyrazolo[1,5-a]pyridin-3-yl-1,3-thiazole-2-carboxamide;
N-(2-Amino-3,3,3-trifluoro-1-phenylpropyl)-5-chloro-4-pyrazolo[1,5-a]pyridin-3-yl-1,3-thiazole-2-carboxamide;
N-[(1S)-1-(Aminomethyl)-2,2,2-trifluoro-1-methylethyl]-5-chloro-4-pyrazolo[1,5-a]pyridin-3-yl-1,3-thiazole-2-carboxamide;
5-Chloro-N-(2-fluorophenyl)-N-methyl-4-pyrazolo[1,5-a]pyridin-3-yl-1,3-thiazole-2-carboxamide;
N-[(1R,2S)-2-amino-6,6-difluoro-2-methylcyclohexyl]-5-chloro-4-(pyrazolo[1,5-a]pyridin-3-yl)-1,3-thiazole-2-carboxamide;

5-Chloro-N-[(1R,6S)-2,2-difluoro-6-hydroxycyclohexyl]-4-(pyrazolo[1,5-a]pyridin-3-yl-1,3-thiazole-2-carboxamide;

N-[(1R,6S)-6-Amino-2,2-difluorocyclohexyl]-5-chloro-4-(6-iodopyrazolo[1,5-a]pyridin-3-yl)-1,3-thiazole-2-carboxamide;

N-[(1R,6S)-6-Amino-2,2-difluorocyclohexyl]-4-(6-bromopyrazolo[1,5-a]pyridin-3-yl)-5-chloro-1,3-thiazole-2-carboxamide;

N-[(1R,6S)-6-Amino-2,2-difluorocyclohexyl]-5-chloro-4-[5-(trifluoromethyl)pyrazolo[1,5-a]pyridin-3-yl]-1,3-thiazole-2-carboxamide;

N-[(1R,6S)-6-Amino-2,2-difluorocyclohexyl]-5-chloro-4-[(6-trifluoromethyl)pyrazolo[1,5-a]pyridin-3-yl]-1,3-thiazole-2-carboxamide;

N-[(1R,6S)-6-Amino-2,2-difluorocyclohexyl]-5-chloro-4-(6-methoxypyrazolo[1,5-a]pyridin-3-yl)-1,3-thiazole-2-carboxamide;

N-[(1R,6S)-6-Amino-2,2-difluorocyclohexyl]-5-chloro-4-(6-ethylpyrazolo[1,5-a]pyridin-3-yl)-1,3-thiazole-2-carboxamide;

N-[(1R,6S)-6-Amino-2,2-difluorocyclohexyl]-5-chloro-4-(5-cyanopyrazolo[1,5-a]pyridin-3-yl)-1,3-thiazole-2-carboxamide;

3-[2-({[(1R,6S)-6-Amino-2,2-difluorocyclohexyl]amino}carbonyl)-5-chloro-1,3-thiazol-4-yl]pyrazolo[1,5-a]pyridine-5-carboxamide;

N-[(1R,6S)-6-amino-2,2-difluorocyclohexyl]-5-chloro-4-(6-fluoropyrazolo[1,5-a]pyridin-3-yl)-1,3-thiazole-2-carboxamide;

N-[(1R,6S)-6-amino-2,2-difluorocyclohexyl]-5-chloro-4-(5-chloropyrazolo[1,5-a]pyridin-3-yl)-1,3-thiazole-2-carboxamide;

N-[(1R,6S)-6-Amino-2,2-difluorocyclohexyl]-5-chloro-4-(5-methylpyrazolo[1,5-a]pyridin-3-yl)-1,3-thiazole-2-carboxamide;

N-[(1R,6S)-6-Amino-2,2-difluorocyclohexyl]-5-chloro-4-(5-chloro-6-fluoropyrazolo[1,5-a]pyridin-3-yl)-1,3-thiazole-2-carboxamide;

N-[(1R,6S)-6-Amino-2,2-difluorocyclohexyl]-4-(6-ethylpyrazolo[1,5-a]pyridin-3-yl)-1,3-thiazole-2-carboxamide;

N-[(1R,6S)-6-Amino-2,2-difluorocyclohexyl]-4-(5-chloro-6-fluoropyrazolo[1,5-a]pyridin-3-yl)-1,3-thiazole-2-carboxamide;

N-[(1R,6S)-6-Amino-2,2-difluorocyclohexyl]-4-(6-methoxypyrazolo[1,5-a]pyridin-3-yl)-1,3-thiazole-2-carboxamide;

N-[(1R,6S)-6-Amino-2,2-difluorocyclohexyl]-4-(5-cyanopyrazolo[1,5-a]pyridin-3-yl)-1,3-thiazole-2-carboxamide;

N-[(1R,6S)-6-Amino-2,2-difluorocyclohexyl]-4-(6-iodopyrazolo[1,5-a]pyridin-3-yl)-1,3-thiazole-2-carboxamide;

N-[(1R,6S)-6-Amino-2,2-difluorocyclohexyl]-4-(6-isopropenylpyrazolo[1,5-a]pyridin-3-yl)-1,3-thiazole-2-carboxamide;

N-[(1R,6S)-6-Amino-2,2-difluorocyclohexyl]-4-(5-chloropyrazolo[1,5-a]pyridin-3-yl)-1,3-thiazole-2-carboxamide;

N-[(1R,6S)-6-Amino-2,2-difluorocyclohexyl]-4-(6-cyanopyrazolo[1,5-a]pyridin-3-yl)-1,3-thiazole-2-carboxamide;

N-[(1R,6S)-6-Amino-2,2-difluorocyclohexyl]-4-[6-methoxy-5-(trifluoromethyl)pyrazolo[1,5-a]pyridin-3-yl]-1,3-thiazole-2-carboxamide;

N-[(1R,6S)-6-Amino-2,2-difluorocyclohexyl]-4-{6-[(trimethyl Silyl)ethynyl]pyrazolo[1,5-a]pyridin-3-yl}-1,3-thiazole-2-carboxamide;

N-[(1R,6R)-6-Amino-2,2-difluorocyclohexyl]-5-chloro-4-(4,6-difluoropyrazolo[1,5-a]pyridin-3-yl)-1,3-thiazole-2-carboxamide;

N-[(1R,6S)-6-Amino-2,2-difluorocyclohexyl]-4-(4-chloro-6-methoxypyrazolo[1,5-a]pyridin-3-yl)-1,3-thiazole-2-carboxamide;

N-[(1R,6S)-6-Amino-2,2-difluorocyclohexyl]-4-(6-ethylpyrazolo[1,5-a]pyridin-3-yl)-1,3-thiazole-2-carboxamide;

N-[(1R,6S)-6-Amino-2,2-difluorocyclohexyl]-4-(5-chloro-6-fluoropyrazolo[1,5-a]pyridin-3-yl)-1,3-thiazole-2-carboxamide;

N-[(1R,6S)-6-Amino-2,2-difluorocyclohexyl]-4-(6-methoxypyrazolo[1,5-a]pyridin-3-yl)-1,3-thiazole-2-carboxamide;

N-[(1R,6S)-6-Amino-2,2-difluorocyclohexyl]-5-chloro-4-(6-cyclopropylpyrazolo[1,5-a]pyridin-3-yl)-1,3-thiazole-2-carboxamide;

N-[(1R,6S)-6-Amino-2,2-difluorocyclohexyl]-5-ethyl-4-(6-fluoropyrazolo[1,5-a]pyridin-3-yl)thiophene-2-carboxamide;

N-[(1R,6S)-6-Amino-2,2-difluorocyclohexyl]-5-isopropyl-4-pyrazolo[1,5-a]pyridin-3-yl-1,3-thiazole-2-carboxamide;

N-[(1R,6R)-6-Amino-2,2-difluorocyclohexyl]-5-isopropyl-4-pyrazolo[1,5-a]pyridin-3-yl-1,3-thiazole-2-carboxamide;

N-[(1R,6S)-6-amino-2,2-difluorocyclohexyl]-5-ethyl-4-[6-(trifluoromethyl)pyrazolo[1,5-a]pyridin-3-yl]thiophene-2-carboxamide;

N-[(1R,6S)-6-Amino-2,2-difluorocyclohexyl]-5-ethyl-4-pyrazolo[1,5-a]pyridin-3-yl-1,3-thiazole-2-carboxamide;

N-[(1R,6S)-6-Amino-2,2-difluorocyclohexyl]-5-methyl-4-pyrazolo[1,5-a]pyridin-3-yl-1,3-thiazole-2-carboxamide;

N-[(1R,6S)-6-Amino-2,2-difluorocyclohexyl]-4-(6-fluoropyrazolo[1,5-a]pyridin-3-yl)-5-methyl-1,3-thiazole-2-carboxamide;

N-[(1R,6S)-6-Amino-2,2-difluorocyclohexyl]-4-(4,6-difluoropyrazolo[1,5-a]pyridin-3-yl)-5-methylthiophene-2-carboxamide;

N-[(trans)-4-Amino-1,1-dioxidotetrahydro-2H-thiopyran-3-yl]-5-methyl-4-(pyrazolo[1,5-a]pyridin-3-yl)thiophene-2-carboxamide;

N-[(cis)-4-Amino-1,1-dioxidotetrahydro-2H-thiopyran-3-yl]-5-methyl-4-(pyrazolo[1,5-a]pyridin-3-yl)thiophene-2-carboxamide;

N-[(1R,6S)-6-Amino-2,2-difluorocyclohexyl]-5-ethyl-4-[6-(trifluoromethyl)pyrazolo[1,5-a]pyridin-3-yl]thiophene-2-carboxamide;

N-[(1R,6S)-6-Amino-2,2-difluorocyclohexyl]-5-ethyl-4-(6-fluoropyrazolo[1,5-a]pyridin-3-yl)thiophene-2-carboxamide;

N-[(1R,6S)-6-Amino-2,2-difluorocyclohexyl]-4-(4,6-difluoropyrazolo[1,5-a]pyridin-3-yl)-5-methylthiophene-2-carboxamide;

N-[(trans)-4-amino-1,1-dioxidotetrahydro-2H-thiopyran-3-yl]-5-chloro-4-(pyrazolo[1,5-a]pyridin-3-yl)thiophene-2-carboxamide;

N-[(cis)-4-amino-1,1-dioxidotetrahydro-2H-thiopyran-3-yl]-5-chloro-4-(pyrazolo[1,5-a]pyridin-3-yl)thiophene-2-carboxamide;

N-[(trans)-3-amino-1,1-dioxidotetrahydro-2H-thiopyran-4-yl]-5-chloro-4-(pyrazolo[1,5-a]pyridin-3-yl)thiophene-2-carboxamide;

N-[(cis)-3-amino-1,1-dioxidotetrahydro-2H-thiopyran-4-yl]-5-chloro-4-(pyrazolo[1,5-a]pyridin-3-yl)thiophene-2-carboxamide;

N-[(1R,6R)-6-Amino-2,2-difluorocyclohexyl]-5-(phenylethynyl)-4-pyrazolo[1,5-a]pyridin-3-yl-1,3-thiazole-2-carboxamide;

N-[(1R,6R)-6-Amino-2,2-difluorocyclohexyl]-5-(3-hydroxy-3-methylbut-1-yn-1-yl)-4-pyrazolo[1,5-a]pyridin-3-yl-1,3-thiazole-2-carboxamide;

N-[(1R,6R)-6-Amino-2,2-difluorocyclohexyl]-5-ethynyl-4-pyrazolo[1,5-a]pyridin-3-yl-1,3-thiazole-2-carboxamide;

N-[(1R,6R)-6-Amino-2,2-difluorocyclohexyl]-5-(cyclopropylethynyl)-4-pyrazolo[1,5-a]pyridin-3-yl-1,3-thiazole-2-carboxamide;

N-[(1R,6R)-6-Amino-2,2-difluorocyclohexyl]-5-(3-methoxyprop-1-yn-1-yl)-4-pyrazolo[1,5-a]pyridin-3-yl-1,3-thiazole-2-carboxamide;

N-[(1R,6R)-6-amino-2,2-difluorocyclohexyl]-5-cyclopent-1-en-1-yl-4-pyrazolo[1,5-a]pyridin-3-yl-1,3-thiazole-2-carboxamide;

N-[(1R,6S)-6-Amino-2,2-difluorocyclohexyl]-5-isopropenyl-4-pyrazolo[1,5-a]pyridin-3-yl-1,3-thiazole-2-carboxamide;

N-[(1R,6S)-6-Amino-2,2-difluorocyclohexyl]-5-isopropenyl-4-[6-(trifluoromethyl)pyrazolo[1,5-a]pyridin-3-yl]-1,3-thiazole-2-carboxamide;

N-[(1R,6S)-6-Amino-2,2-difluorocyclohexyl]-4-pyrazolo[1,5-a]pyridin-3-yl-5-vinyl-1,3-thiazole-2-carboxamide;

N-[(1R,6S)-6-Amino-2,2-difluorocyclohexyl]-4-(6-fluoropyrazolo[1,5-a]pyridin-3-yl)-5-isopropenyl-1,3-thiazole-2-carboxamide;

N-[(1R,6R)-6-amino-2,2-difluorocyclohexyl]-5-[(1E)-but-1-en-1-yl]-4-pyrazolo[1,5-a]pyridin-3-yl-1,3-thiazole-2-carboxamide;

N-[(1R,6R)-6-Amino-2,2-difluorocyclohexyl]-4-pyrazolo[1,5-a]pyridin-3-yl-5-vinyl-1,3-thiazole-2-carboxamide;

N-[(1R,6R)-6-amino-2,2-difluorocyclohexyl]-5-(2-methylprop-1-en-1-yl)-4-pyrazolo[1,5-a]pyridin-3-yl-1,3-thiazole-2-carboxamide;

N-[(1R,6R)-6-amino-2,2-difluorocyclohexyl]-5-[(E)-2-cyclohexylvinyl]-4-pyrazolo[1,5-a]pyridin-3-yl-1,3-thiazole-2-carboxamide;

N-[(1R,6R)-6-amino-2,2-difluorocyclohexyl]-5-[(E)-2-cyclopropylvinyl]-4-pyrazolo[1,5-a]pyridin-3-yl-1,3-thiazole-2-carboxamide;

N-[(1R,6S)-6-amino-2,2-difluorocyclohexyl]-5-cyclopropyl-4-pyrazolo[1,5-a]pyridin-3-yl-1,3-thiazole-2-carboxamide;

N-[(1R,6R)-6-amino-2,2-difluorocyclohexyl]-5-cyano-4-pyrazolo[1,5-a]pyridin-3-yl-1,3-thiazole-2-carboxamide;

N-[(1R,6S)-6-amino-2,2-difluorocyclohexyl]-5-(difluoromethyl)-4-pyrazolo[1,5-a]pyridin-3-ylthiophene-2-carboxamide;

N-[(1R,6S)-6-Amino-2,2-difluorocyclohexyl]-5-(difluoromethyl)-4-(6-fluoropyrazolo[1,5-a]pyridin-3-yl)-1,3-thiazole-2-carboxamide;

N-[(1R,6S)-6-Amino-2,2-difluorocyclohexyl]-5-(difluoromethyl)-4-[6-(trifluoromethyl)pyrazolo[1,5-a]pyridin-3-yl]-1,3-thiazole-2-carboxamide;

N-[(1R,6R)-6-Amino-2,2-difluorocyclohexyl]-5-nitro-4-pyrazolo[1,5-a]pyridin-3-yl-1,3-thiazole-2-carboxamide;

2-(Piperidin-1-ylcarbonyl)-4-pyrazolo[1,5-a]pyridin-3-yl-1,3-thiazol-5-amine; and N-[(1R,6S)-6-Amino-2,2-difluorocyclohexyl]-5-(dimethylamino)-4-pyrazolo[1,5-a]pyridin-3-yl-1,3-thiazole-2-carboxamide;

or a pharmaceutically acceptable salt of any of the foregoing compounds.

18. A compound according to claim 1 according to Formula Ia

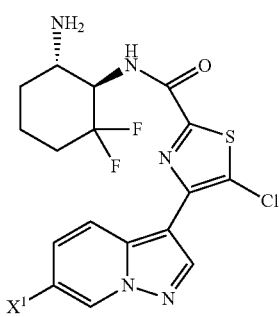

Ia or a pharmaceutically acceptable salt or hydrate thereof.

19. A pharmaceutical composition comprising a compound of formula I as defined in claim 1 or a pharmaceutically acceptable salt or hydrate thereof, and a pharmaceutically acceptable carrier.

* * * * *

UNITED STATES PATENT AND TRADEMARK OFFICE
CERTIFICATE OF CORRECTION

Page 1 of 1

PATENT NO. : 8,518,911 B2
APPLICATION NO. : 13/057510
DATED : August 27, 2013
INVENTOR(S) : Jason D. Katz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this
Third Day of March, 2015

Michelle K. Lee
*Deputy Director of the United States Patent and Trademark Office*